(12) United States Patent
Boger et al.

(10) Patent No.: US 6,251,931 B1
(45) Date of Patent: Jun. 26, 2001

(54) INHIBITORS OF GAP JUNCTION COMMUNICATION

(75) Inventors: Dale L. Boger; Norton B. Gilula; Richard A. Lerner; Benjamin F. Cravatt, all of La Jolla, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 09/529,909

(22) PCT Filed: Nov. 24, 1998

(86) PCT No.: PCT/US98/24913

§ 371 Date: Apr. 19, 2000

§ 102(e) Date: Apr. 19, 2000

(87) PCT Pub. No.: WO99/26584

PCT Pub. Date: Jun. 3, 1999

(51) Int. Cl.[7] ..................................... A61K 31/40
(52) U.S. Cl. ................... 514/408; 514/422; 514/423; 514/613; 514/702; 514/703; 514/705; 554/51; 554/55; 554/56; 554/59; 554/213; 554/214; 554/223; 548/400; 548/514; 548/530
(58) Field of Search .................... 514/408, 422, 514/423, 613, 702, 703, 705; 554/51, 55, 56, 59, 213, 214, 223; 548/400, 517, 530

(56) References Cited

PUBLICATIONS

Bachur, et al., "Fatty Acid Amides of Ethanolamine in Mammalian Tissues", *J. Biol. Chem.* 240: 1019–1024 (1965).

Aylsworth, et al., "Influence of Lipids on Gap–Junction–mediated Intercellular Communication between Chinese Hamster Cells in Vitro", *Cancer Res.* 46: 4527–4533 (1996).

Arafat, et al., "Identification of Fatty Acid Amides in Human Plasma", *Life Sci.* 45: 1679–1687 (1987).

Schmid, et al., "N–Acylated Glycerophospholipids and Their Derivatives", *Prog. Lipid Res.* 29: 1–43 (1990).

Wakamatsu, et al., "Isolation of Fatty Acid Amide as an Angiogenic Principle from Bovine Mesentery", *Biochem. Biophys. Res. Commun.* 168: 423–429 (1990).

Spray, et al., "Structure–Activity Relations of the Cardiac Gap Junction Channel", *Am. J. Physiol.* 258: C195–C205 (1990).

Burt, et al., "Uncoupling of Cardiac Cells by Fatty Acids: Structure–Activity Relationships", *Am. J. Physiol.* 260: C439–C448 (1991).

(List continued on next page.)

*Primary Examiner*—Deborah D. Carr
(74) *Attorney, Agent, or Firm*—Thomas E. Northrup

(57) ABSTRACT

Oleamide is an endogenous fatty acid primary amide that possesses sleep-inducing properties in animals and has been shown to effect seratonergic systems and block gap junction communication in a structurally specific manner. Certain agents can serve both as an oleamide agonist and as an inhibitor of fatty acid amide hydrolase. Fatty acid amide hydrolase is responsible for the rapid inactivation of oleamide in vivo. The structural features of oleamide required for inhibition of gap junction-mediated chemical and electrical transmission in rat glial cells are defined. Effective inhibitors fall into two classes of fatty acid primary amides of which oleamide and arachidonamide are the prototypical members. Of these two, oleamide constitutes the most effective and its structural requirements for inhibition of the gap junction are well defined. It requires a chain length of 16–24 carbons of which 16–18 carbons appears optimal, a polarized terminal carbonyl group capable of accepting but not necessarily donating a hydrogen bond, a Δ9 cis double bond, and a hydrophobic methyl terminus. Within these constraints, a range of modifications are possible, many of which may with enhanced in vivo properties.

2 Claims, 22 Drawing Sheets

OTHER PUBLICATIONS

Hasler, et al., "Inhibition of Gap Junction–Mediated Intercellular Communication by α–Linolenate", *Am. J. Physiol. 261*: C161–C168 (1991).

Ramachandran, et al., "Enzymatic Hydrolysis of Sphingomyelin in 3T3–Li Cells: Modulation by Dexamethasone", *Biochem. Arch. 8*: 369–377 (1992).

Massey, et al., "Arachidonic Acid and Lipoxygenase Metabolites Uncouple Neonatal Rat Cardiac Myocyte Pairs", *Am. J. Physiol. 263*: C494–C501 (1992).

Jain, et al., "Fatty Acid Amides: Scooting Mode–Based Discovery of Tight–Binding Competitive Inhibitors of Secreted Phospholipases $A_2$",*J. Med. Chem. 35*: 3584–3586 (1992).

Felder, et al., "Anandamide, an Endogenous Cannabimimetic Eicosanoid, Binds to the Cloned Human Cannabinoid Receptor and Stimulates Receptor–Mediated Signal Transduction", *Proc. Natl. Acad. Sci. USA 90*: 7656–7660 (1993).

Hirschi, et al., "Oleic Acid Differentially Affects Gap Junction–Mediated Communication in Heart and Vascular Smooth Muscle Cells", *Am. J. Physiol. 265*: C1517–C1526 (1993).

Hanuš, et al., "Two New Unsaturated Fatty Acid Ethanolamides in Brain That Bind to the Cannabinoid Receptor", *J. Med. Chem. 36*: 3032–3034 (1993).

Abadji, et al., "(R)–Methanandamide: A Chiral Novel Anandamide Possessing Higher Potency and Metabolic Stability", *J. Med. Chem. 37*: 1889–1893 (1994).

Pinto, et al., "Cannabinoid Receptor Binding and Agonist Activity of Amides and Esters of Arachidonic Acid", *Mol. Pharmacol. 46*: 516–522 (1994).

Adams, et al., "Pharmacological and Behavioral Evaluation of Aklylated Anandamide Analogs", *Life Sci. 56*: 2041–2048 (1995).

Mechoulam, et al., "Identification of an Endogenous 2–Monoglyceride, Present in Canine Gut, that Binds to Cannabinoid Receptors", *Biochem. Pharmacol. 50*: 83–90 (1995).

Priller, et al., "Mead Ethanolamide, a Novel Eicosanoid, Is an Agonist for the Central (CB1) and Peripheral (CB2) Cannabinoid Receptors", *Mol. Pharmacol. 48*: 288–292 (1995).

Adams, et al., "Evaluation of Cannabinoid Receptor Binding and in Vivo Activities for Anandamide Amalogs", *J. Pharmacol. Exp. Ther. 273*: 1172–1181 (1995).

Venance, et al., "Inhibition by Anandamide of Gap Junctions and Intercellular Calcium Signalling in Striatal Astrocytes", *Nature 376*: 590–594 (1995).

Huidobro–Toro, et al., "Brain Lipids that Induce Sleep are Novel Modulators of 5–Hydroxytryptamine Receptors", *Proc. Natl. Acad. Sci. USA 93*: 8078–8082 (1996).

Khanolkar, et al., "Head Group Analogs of Arachidonylethanolamide, the Endogenous Cannabinoid Ligand", *J. Med. Chem. 39*: 4515–4519 (1996).

| structure | notation[a] | % inhibition[b] | | |
|---|---|---|---|---|
| | | 100 µM | 50 µM | 20 µM |
| *no double bond* | | | | |
| stearamide | 18:0 | nd[c] | 0% | nd[d] |
| *one double bond* | | | | |
| myristoleamide | 14:1[9] | 0% | 0% | nd |
| palmitoleamide | 16:1[9] | 100% | 100% | 100% |
| | 17:1[8] | nd | 100% | 100% |
| petroselinamide | 18:1[6] | nd | 100% | 100% |
| | 18:1[7] | nd | 100% | 100% |
| | 18:1[8] | 100% | 100% | 30% |
| oleamide | 18:1[9] | 100% | 100% | 100% |
| elaidamide | 18:1[9-trans] | 0% | 0% | 0% |
| vaccenamide | 18:1[11] | 100% | 25% | 0% |
| | 18:1[12] | nd | 90-100% | nd |
| | 18:1[13] | nd | 75-90% | nd |
| | 18:1[15] | nd | 0% | nd |
| | 19:1[10] | nd | 100% | nd |
| | 20:1[5] | nd | 0% | nd |
| | 20:1[8] | nd | 95-100% | nd |
| | 20:1[9] | 100% | 100% | 0% |
| | 20:1[11] | 100% | 100% | nd |

FIG. 2A

| structure | notation[a] | % inhibition[b] | | |
|---|---|---|---|---|
| | | 100 μM | 50 μM | 20 μM |
| (H₂N-C(=O)- ...) | 20:1[13] | 0% | 0% | nd |
| (H₂N-C(=O)- ...) | 22:1[9] | 100% | 100% | 0% |
| erucamide | 22:1[13] | 0% | 0% | nd |
| (H₂N-C(=O)- ...) | 24:1[9] | 100% | 100% | 0% |
| nervonamide | 24:1[15] | 0% | 0% | nd |
| *two double bonds* | | | | |
| linoleamide | 18:2[9,12] | nd | 100% | 10% |
| linoelaidamide | 18:2[9,12-trans] | 75% | 25% | nd |
| (H₂N-C(=O)- ...) | 20:2[11,14] | nd | 90% | 20% |
| *three double bonds* | | | | |
| γ-linolenamide | 18:3[6,9,12] | nd | 100% | 15% |
| α-linolenamide | 18:3[9,12,15] | 0% | 0% | nd |
| (H₂N-C(=O)- ...) | 20:3[8,11,14] | nd | 0% | nd |
| (H₂N-C(=O)- ...) | 20:3[11,14,17] | nd | 0% | nd |
| *four double bonds* | | | | |
| arachidonamide | 20:4[5,8,11,14] | 100% | 100% | 90-100% |
| *five double bonds* | | | | |
| eicosapentaenamide | 20:5[5,8,11,14,17] | nd | 100% | nd |
| *six double bonds* | | | | |
| docosahexaenamide | 22:6[4,7,10,13,16,19] | 0% | 0% | nd |

FIG. 2B

| agent (R) | % inhibition[a] | | |
|---|---|---|---|
| | 100 μM | 50 μM | 20 μM |
| NH₂ (oleamide) | 100% | 100% | 100% |
| OH (oleic acid) | 0% | 0% | 0% |
| MeNH | nd[b] | 100% | 70-80% |
| Me₂N | nd | 100% | 70-85% |
| EtNH | nd | 100% | 50-60% |
| Et₂N | nd | 100% | 15-25% |
| CH₂=CHCH₂NH | nd | 100% | nd |
| PrNH | nd | 90-100% | 50-70% |
| i-PrNH | nd | 100% | nd |
| ▷—NH | nd | 100% | nd |
| i-PrNMe | nd | 100% | nd |
| BuNH | nd | 100% | nd |
| ⌬N (pyrrolidine) | nd | 100%[c] | 0%[d] |
| PhNH | nd | 0% | nd |
| Ph(CH₂)₃NH | nd | 0% | nd |
| HONH | nd | 100%[c] | 0%[d] |
| MeONMe | nd | 100%[c] | 100%[c,d] |
| NH₂NH | nd | 0%[e] | nd |
| CH₃O (methyl oleate) | 0% | 0% | nd |
| EtO (ethyl oleate) | nd | 0% | nd |
| Me₂CHCH₂O | nd | 0% | nd |
| H (oleyl aldehyde) | nd | 100% | 70-90% |
| CF₃ | nd | 100%[c] | 100%[c,d,f] |
| BrCH₂ | nd | 15% | nd |
| ClCH₂ | nd | 0% | nd |
| N₂CH | nd | 100% | nd |
| CH₂OH (oleyl alcohol) | 80-100% | 15% | nd |
| CH₂OAc (oleyl acetate) | nd | 0% | nd |
| CH₂NH₂ (oleyl amine) | 100% | 100% | 90-100% |
| CH₂NHCONH₂ | nd | 10% | nd |
| CH(OMe)₂ (oleyl aldehyde dimethyl acetal) | nd | 0% | nd |
| CoA-SCO | nd | 0% | nd |

FIG. 3

| agent (R) | % inhibition[a] | | |
|---|---|---|---|
| | 100 μM | 50 μM | 20 μM |
| NH₂ (oleamide) | 100% | 100% | 100% |
| HOCH₂CH₂NH | 100% | 100% | 0% |
| (HOCH₂CH₂)₂N | nd[b] | 8% | nd |
| HOCH₂CH₂CH₂NH | nd | 100% | nd |
| HOCH₂CH(OAc)CH₂O[c] | 50% | 0% | 0% |

| agent (R) | % inhibition[a] | | |
|---|---|---|---|
| | 100 μM | 50 μM | 20 μM |
| NH₂ | 100% | 100% | 90-100% |
| HOCH₂CH₂NH | 100% | 100% | 35% |
| (HOCH₂CH₂)₂N | nd | 0% | nd |

FIG. 4

| agent (R) | % inhibition[a] | | |
|---|---|---|---|
| | 100 μM | 50 μM | 20 μM |
| CH₃ (oleamide) | 100% | 100% | 100% |
| (CH₂)₂CH₃ | 100% | 100% | 0% |
| (CH₂)₄CH₃ | 100% | 100% | 0% |
| (CH₂)₆CH₃ | 100% | 100% | 0% |
| CH₂OCH₃ | nd[b] | 100% | nd |
| CH₂OH | nd | 8% | nd |
| CONH₂ | nd | 0% | nd |
| CO₂H | nd | 0% | nd |

FIG. 5

| agent | | % inhibition[a] | | |
|---|---|---|---|---|
| R | R¹ | 100 μM | 50 μM | 20 μM |
| OH | H | nd | 0% | nd[b] |
| NH₂ | H | nd | 0%[c] | nd |
| OEt | H | nd | 90-100% | nd |
| OH | Me | 100% | 100% | 70-80% |
| OEt | Me | nd | 90-100% | nd |

FIG. 6

| Treatment | Number of cells participating in wave (in one direction) | | | | Junction dye-coupling (%) |
|---|---|---|---|---|---|
| | 2 sec | 4 sec | 8 sec | 16 sec | |
| Control | 1.16±0.37 | 2.48±0.63 | 6.74±0.93 | 11.26±1.34 | 97.5±1.72 |
| Oleamide (50 μM) | 1.13±0.34 | 2.39±0.56 | 6.55±0.99 | 10.77±2.25 | 0.12±0.08 |
| Anandamide (50 μM) | 1.09±0.30 | 2.39±0.67 | 6.58±1.09 | 11.06±1.31 | 0.09±0.05 |
| 18β-GA (40 μM) | 0.06±0.03 | 0.06±0.03 | 0.06±0.03 | 0.06±0.03 | 0.09±0.04 |
| Heptanol (3 mM) | 0.03±0.02 | 0.03±0.02 | 0.03±0.02 | 0.03±0.02 | 0.14±0.12 |
| Suramin (200 μM) | 0.90±0.30 | 0.94±0.33 | 0.94±0.33 | 0.94±0.33 | 98.2±1.20 |
| Oleamide+Suramin | 0.83±0.38 | 0.86±0.35 | 0.86±0.35 | 0.86±0.35 | 0.08±0.03 |

The number of cells participating in calcium wave propagation was quantified by counting the number of responding cells in one direction from the stimulated cell. The time points indicated above were analyzed after the initiation of calcium signaling; the responding cell numbers are expressed as Mean ± SD. Gap junction dye transfer was expressed as dye coupling percentage (Mean ± SD) which is described in Experimental Procedures. Each treatment was performed in 3 dishes, and 10 individual fields were examined in each dish, N=30.

FIG. 9

INHIBITORS OF GAP JUNCTION COMMUNICATION

This application is a 371 of PCT/US98/24913 filed Nov. 24, 1998.

This invention was made with government support under Contract No. CA42056 by the National Institutes of Health. The government has certain rights in the invention.

TECHNICAL FIELD

The present invention relates to compounds that serve both as oleamide agonists and as inhibitors of fatty acid amide hydrolase. More particularly, the present invention relates to oleamide agonists for inhibition of gap junction-mediated chemical and electrical transmission in glial cells.

BACKGROUND

Oleamide (1) is an endogenous fatty acid primary amide shown to accumulate in the cerebrospinal fluid under conditions of sleep deprivation and disappear upon sleep recovery (Cravatt et al. (1995) *Science* 268, 1506–1509; Lerner et al. (1994) *Proc. Natl. Acad. Sci. USA* 91, 9505–9508; Cravatt et al. (1996) *J. Am. Chem. Soc.* 118, 580–590). In a structurally specific manner, it has been shown to induce physiological sleep in animals when administered by ip or iv injection. Consistent with its role as a prototypical member of a new class of biological signaling molecules, enzymatic regulation of the endogenous concentrations of oleamide has been described or proposed.

Fatty acid amide hydrolase (FAAH, oleamide hydrolase) is an integral membrane protein that degrades 1 to oleic acid and potent inhibitors (Ki=13 $\mu M^{-1}$ nM) of the enzyme with sleep-inducing properties have been detailed. The purification, characterization, cloning, expression and neuronal distribution of FAAH have been disclosed and it was found to possess the capabilities of hydrolyzing a range of fatty acid amides including anandamide which serves as an endogenous ligand for cannabinoid receptors.

In contrast to anandamide, an appealing feature of the members of this new class of biological signaling agents is the primary amide suggesting that their storage and release may be controlled in a manner analogous to that of short peptide hormones and messengers terminating in a primary amide (Patterson et al. (1996) *J. Am. Chem. Soc.* 118, 5938–5945; Cravatt et al. (1996) *Nature* 384, 83–87; Giang et al. (1997) *Proc. Natl. Acad. Sci. USA* 94, 2238–2242; Merkler et al. (1996) *Arch. Biochem. Biophys.* 330, 430–434; Devane et al. (1992) *Science* 258, 1946–1949; Johnson et al. (1993) *Protaglandins, Leukot. Essent. Fatty Acids* 48, 429–437; Di Marzo et al. (1995) *Prostaglandins, Leukot. Essent. Fatty Acids* 53, 1–11).

SUMMARY OF THE INVENTION

The invention is directed to inhibitors of gap junction communication. More particularly, one aspect of the invention is directed to compounds having oleamide agonist activity for inhibiting gap junction-mediated chemical and electrical transmission in glial cells. Preferred compounds are represented by the structure:

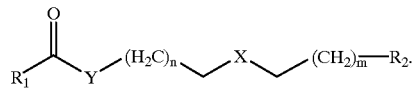

In the above structure, X is one of the diradicals represented by the following structures:

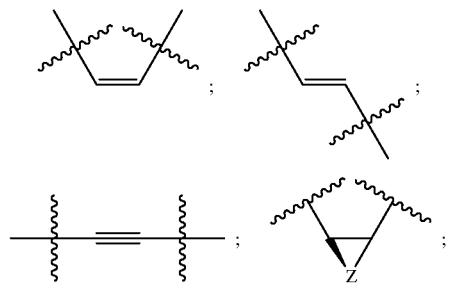

wherein Z is either —CH or O. Y is a diradical selected from the the following: —CH$_2$—, —CH(CH$_3$)—, —C(CH$_3$)$_2$—, —O—, —NH—, —CH(SH)—, —CHSAc)—, —CH(OH)—, —CHCl—, —C(=O)—, —C(=O)CH$_2$—, —CH$_2$NHC(=O)—, or —CH$_2$N(CH$_3$)C(=O)—. R$_1$ is a radical selected from the following: hydrogen, —NH$_2$, OH, MeNH—, Me$_2$N—, EtNH—, Et$_2$N—, CH$_2$=CHCH$_2$NH—, n-propyl-NH—, i-propyl-NH—, cyclopropyl-NH—, i-propyl-NMe—, butyl-NH—, pyrrolidine-, phenyl-NH—, phenyl(CH$_2$)$_3$NH—, HONH—, MeONMe—, NH$_2$NH—, CH$_3$O—, CH$_3$CH$_2$O—, CH$_3$(CH$_2$)$_2$O—, Me$_2$CHCH$_2$O—, H—, CF$_3$—, BrCH$_2$—, ClCH$_2$—, N$_2$CH—, HOCH$_2$CH$_2$NH—, (HOCH$_2$CH$_2$)$_2$N—, HOCH$_2$CH$_2$CH$_2$NH—, or HOCH$_2$CH(OAc)CH$_2$O—. R$_2$ is a radical selected from the following:
—CH$_3$, —(CH$_2$)$_2$CH$_3$, —(CH$_2$)$_4$CH$_3$, —(CH$_2$)$_6$CH$_3$, —CH$_2$OCH$_3$, —CH$_2$OH, —CONH$_2$ or —CO$_2$H. n is an integer from 0 to 15; m is an integer from 0 to 15 with the requirement that the sum of n+m is an integer from 11 to 15. However, if Y is CH$_2$, n is 4, m is 7, and R$_2$ is CH$_3$, then R$_1$ cannot be a radical selected from the group consisting of —CF$_3$ and hydrogen. Furthermore, if Y is CH$_2$, n is 5, m is 7, and R$_2$ is CH$_3$, then R$_1$ cannot be a radical selected from the group consisting of —CF$_3$, —CH$_2$Cl, —NHOH, —C(O)NH$_2$, —CN$_2$, and —C(O)OEt. If Y is CHCl, n is 4, m is 7, and R$_2$ is CH$_3$, then R$_1$ cannot be NH$_2$. If Y is CH(OH), n is 4, m is 7, and R$_2$ is CH$_3$, then R$_1$ cannot be NH$_2$. If Y is C(=O), n is 4, m is 7, and R$_2$ is CH$_3$, then R$_1$ cannot be NH$_2$ and CH$_3$CH$_2$O—. And finally, if Y is CH$_2$, 4≦n≦9, 4≦n≦7, and R$_2$ is CH$_3$, then R$_1$ cannot be NH$_2$ and OH.

Another aspect of the invention is directed to a method for inhibiting gap junction mediated chemical and electrical transmission in glial cells by contacting such cells with the oleamide agonists represented above.

DESCRIPTION OF FIGURES

FIG. 2 illustrates fatty acid primary amide analogs with % inhibition of gap junction-mediated dye transfer wherein the indicated footnotes are represented as follows: (a) Chain length:number of double bonds position of double bond, the double bond stereochemistry is cis unless indicated otherwise. (b) % Inhibition of lucifer yellow dye transfer by rat glial cell gap junction at the indicated concentration of agent. (c) Low solubility precluded testing at higher concentration. (d) Not done (For 22:1[9], see FIG. 18 for synthesis)

FIG. 3 illustrates carboxamide terminus analogs with % inhibition of gap junction-mediated dye transfer wherein the indicated footnotes are represented as follows: (a) inhibition of GAP junction-mediated dye transfer, see FIG. 2; (b) Not done; (c) Toxic to cells at concentration tested; (d) Tested at 25 mM. (e) Insoluble at concentration tested. (f) Reversible inhibition.

FIG. 4 illustrates ethanolamide substituted analogs with % inhibition of gap junction-mediated dye transfer wherein the indicated footnotes are represented as follows: (a) Inhibition of GAP junction-mediated dye transfer, see FIG. 2; (b) Not done; (c) Racemic and (2S)-1-oleyl-2-acetylglycerol.

FIG. 5 illustrates methyl terminus substituted analogs with % inhibition of gap junction-mediated dye transfer wherein the indicated footnotes are represented as follows: (a) Inhibition of GAP junction-mediated dye transfer, see FIG. 2 and FIG. 19 for further data and synthetic routes for some of these compounds.

FIG. 6 illustrates N-Oleyl Glycine substituted analogs with % inhibition of gap junction-mediated dye transfer wherein the indicated footnotes are represented as follows: (a) Inhibition of GAP junction-mediated dye transfer, see FIG. 2; (b) Not done; (c) Low solubility.

FIG. 9 illustrates the effects of different agents on calcium wave propagation and gap junctional communication. The number of cells participating in calcium wave propagation was quantified by counting the number of responding cells in one direction from the stimulated cell. The time points indicated above were analyzed after the initiation of calcium signaling; the responding cell numbers are expressed as Mean±SD. Gap Junction dye transfer was expressed as dye coupling percentage (Mean±SD) which is described in the assay procedures. Each treatment was performed in 3 dishes, and 10 individual fields were examined in each dish, N=30.

DETAILED DESCRIPTION

Figure 1:
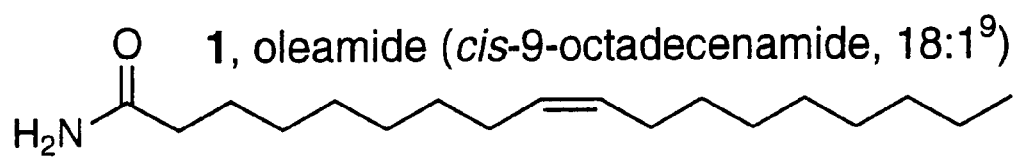
FIG. 1 shows a structure of the sleep inducing lipid, oleamide (cis-9-octadecenamide, 18:1$^9$).

The invention relates to compounds that serve both as oleamide agonists and as inhibitors of fatty acid amide hydrolase. More particularly, the present invention relates to oleamide agonists for inhibition of gap junction-mediated chemical and electrical transmission in glial cells.

Our finding that oleamide inhibits the gap junction-mediated intercellular chemical and electrical transmission without effecting calcium wave propagation in rat glial cells suggests this may constitute an important site of action for this new class of biologically active lipids. The effective inhibitors of the gap junction fall into two classes of fatty acid primary amides of which oleamide and arachidonamide are the prototypical members. Of these, oleamide constitutes the most effective and its structural requirements for inhibition of the gap junction are well defined. The inhibition requires a chain length of 16–24 carbons of which 16–18 appears optimal, a polarized terminal carbonyl capable of accepting but not necessarily donating a hydrogen bond, a Δ9 cis double bond, and a hydrophobic methyl terminus. Within these constraints, a range of modifications are acceptable, many of which may be utilized to enhance in vivo properties. In addition to those which would slow or avoid inactivation by FAAH hydrolysis, a set of especially interesting agents have been identified which serve both as oleamide agonists and as FAAH inhibitors.

The inhibition of the gap junction by oleamide is consistent with a number of mechanisms. Perturbations in the bulk membrane fluidity or the membrane-protein interface that would effect the conformation of the membrane bound proteins as well as direct interaction with the gap junction proteins have been discussed (Lars Bastiaanse et al. (1993) *J. Membrane Biol.* 136, 135–145). Similarly, we are looking at both progressive closure and ultimately collapse of the gap junction as well as gated closure of the gap junction. The compounds disclosed herein and the defined structural features of oleamide responsible for the properties may help distinguish among the mechanisms as well as provide new neuromodulatory agents applicable to sleep or mood disorders, analgesia, and disorders associated with higher neuronal function.

EXAMPLE 1

Chemical Requirements and Design of Analogs For Inhibition of Gap Junction Communication By the Biologically Active Lipid Oleamide In addition to its sleep-inducing properties in animals, oleamide has been shown to effect serotonergic systems (Huidobro-Toro et al. (1996) *Proc. Natl. Acad. Sci. USA* 93, 8078–8082) and block gap junction communication in a structurally specific manner. Moreover, while it was found to inhibit the gap junction-mediated chemical and electrical transmission in rat glial cells, it had no inhibitory effect or mechanically-stimulated or glutamate-induced calcium wave propagation thereby decoupling two previously indistinguishable glial cell communication pathways. Given the central role of intercellular chemical and electrical signaling in the CNS, the oleamide inactivation of glial cell gap junction channels may influence higher order neuronal function including sleep.

Fatty Acid Primary Amide Analogs

The first series of compounds examined were the primary amides of the naturally occurring fatty acids and related synthetic analogs, FIG. 2 (Arafat et al. (1989) *Life Sci.* 45, 1679–1687; Wakamatsu et al. (1990) *Biochem. Biophys. Res. Commnun.* 168, 423–429; Jain et al. (1992) *J. Med. Chem.* 35, 3584–3586). We have examined the number, position, and stereochemistry of the double bond(s), and the length of the agent. From these studies, which were assisted with the inclusion of the primary amides of nonnaturally occurring fatty acids, a clear depiction of the structural requirements of the endogenous agent emerged. The effective inhibitors of the gap junction-mediated dye transfer fall into two classes of which oleamide and arachidonamide are the prototypical members (Pinto et al. (1994) *Mol. Pharmacol.* 46, 516–522; Felder et al. (1993) *Proc. Natl. Acad. Sci. USA* 90, 7656–7660; Abadji et al. (1994) *J. Med. Chem.* 37, 1889–1893; Adams et al. (1995) *J. Pharmacol. Exp. Therapeut.* 273, 1172–1181; Adams et al. (1995) *Life Sci.* 56, 2041–2048; Priller et al. (1995) *Mol. Pharmacol.* 48, 288–292; Khanolkar et al. (1996) *J. Med. Chem.* 39, 4515–4519; Venance et al. (1995) *Nature* 376, 590–594).

For agents related to oleamide that contain one double bond, the presence, position, and stereochemistry of the olefin as well as the chain length were found to have a defined relationship. The monounsaturated fatty acid primary amides of 16–24 carbons containing a $\Delta 9$ cis double bond were all found to be effective inhibitors of the gap junction-mediated dye transfer. Removal of the $\Delta 9$ double bond (18:0) or its replacement with a trans double bond ($18:1^{9\text{-}trans}$) resulted in no observable inhibition at the concentrations examined. Shortening the chain length to 14 carbons (14:19) resulted in t loss of activity while lengthening the chain slightly diminished the inhibitory effectiveness. No further substantial trend in the length was observed with the longer fatty acid primary amides provided they possess a $\Delta 9$ cis double bond: $14:1^9 << 16:1^9 = 18:1^9 > 20:1^9 = 22:1^9 = 24:1^9$ (i.e. chain length:number of double bond$^{position\ of\ double\ bond}$) (FIG. 2).

The position of the cis double bond had a well-defined effect on the potency. A $\Delta 9$ cis olefin exhibited the strongest inhibitory effect and the potency typically declined as its position was moved in either direction. This is apparent in the comparisons made in oleamide series (18:1) and especially clear in the eicosenoamide series (20:1) where the potency declined as the distance from the $\Delta 9$ position increased. Although this location in oleamide is central to its structure and potentially represents a relationship with either the carboxamide or methyl terminus, the potent activity of palmitoleamide ($16:1^9$) suggested that it is the positional relationship with the amide that is important.

This was confirmed in the 20:1, 22:1, and 24:1 series where inhibitory activity was observed preferentially with the synthetic $\Delta 9$ olefins rather than the naturally occurring isomers bearing a cis double bond 9 carbons from the methyl terminus: $20:1^9 = 20:1^{11}$, $22:1^9 > 22:1^{13}$ and $24:1^9 > 24:1^{15}$. In this context it is interesting that erucamide (Hasler et al. (1991) *Am. J. Physiol.* 261 (*Cell Physiol.* 30), C161–C168), which has been detected in human cerebrospinal fluid, is not an inhibitor of the gap junction and does not induce physiological sleep in rat (FIG. 2).

With the polyunsaturated fatty acid primary amides, those containing two double bonds exhibited modest activity. Typically, this was considerably diminished relative to that of oleamide except linoleamide (18:2) which also possesses the cis $\Delta 9$ double bond. Even with linoleamide, the inhibition potency was lower than oleamide indicating that the additional $\Delta 12$ cis double bond was not beneficial (FIG. 2).

The primary amide of fatty acids containing three double bonds were even less active with essentially all members being ineffective at 50 $\mu$M. This includes $\alpha$-linolenamide ($20:3^{9,12,15}$) which incorporates the $\Delta 9$ cis double bond of oleamide and $20:3^{8,11,14}$ which incorporates an alternative $\Delta 8$ or $\Delta 11$ cis double bond. The exception to this generalization is $\gamma$-linolenamide ($18:3^{6,9,12}$) which proved to be an effective but less potent inhibitor. Similarly, arachidonamide containing four cis double bonds was an effective inhibitor of the gap junction-mediated dye transfer although it was not quite as potent as oleamide. This effect was also observed with a fatty acid primary amide containing five cis double bonds but was lost again with that possessing six double bonds (FIG. 2).

These results are consistent with two classes of fatty acid primary amides that inhibit the gap junction-mediated dye transfer. The prototypical member of the first, more potent class is oleamide and the second, slightly less effective class, contains arachidonamide (FIG. 2).

Carboxamide Analogs

An extensive study of the requirements at the carboxylate terminus proved revealing in that it was surprisingly tolerant, FIG. 3. Oleic acid was found to be inactive at the concentrations examined, and oleyl alcohol, methyl or ethyl oleate, and oleyl acetate exhibited progressively reduced effectiveness. Oleic acid (Hirschi et al. (1993) *Am. J. Physiol.* 265 (*Cell Physiol.* 34), C1517–C1526; Burt et al. (1991) *Am. J. Physiol.* 260 (*Cell Physiol.* 29), C439–C448), arachidonic acid (Giaume et al. (1991) *Proc. Natl. Acad. Sci. USA* 88, 5577–5581. Massey et al. (1992) *Am. J. Physiol.* 263 (*Cell Physiol.* 32), C494–C501), and $\alpha$-linolenic acid (Hasler et al. (1991) *Am. J. Physiol.* 261 (*Cell Physiol.* 30), C161–C168) have been reported to inhibit the gap junction in rat cardiac myocytes, striatal astrocytes, and rat liver epithelial cells, respectively. The limited studies of their structural requirements for gap junction inhibition including the chain length, degree and site of unsaturation, and the stereochemistry of the double bond(s) roughly follow those detailed herein although fewer fatty acids have been examined in these efforts (Aylsworth et al. (1986) *Cancer Res.* 46, 4527–4533; Spray et al. (1990) *Am. J. Physiol.* 258 (*Cell Physiol.* 27), C195–205).

The comparisons detailed in FIG. 3 suggest that the most effective derivatives of the fatty acids in rat glial cells are the primary amides. However, a wide range of secondary or teritary amides were also found to also be potent inhibitors of the gap junction-mediated dye transfer. Thus, the hydrogen bond donor capability of the primary amides is not essential to the expression of their properties. Many of these were equipotent with oleamide and the series examined exhibited a clear trend favoring the smaller secondary or tertiary amide substituents. This is evident upon comparing the effects of $R=NH_2 \geq MeNH > Et_2N > c\text{-}(CH_2)_4N > PhNH$. Although the secondary amides typically were more potent than the corresponding tertiary amides, the comparable potency of the N-methyl and N,N-dimethyl amide (MeNH= Me$_2$N) is notable. This is consistent with a requirement for small amide substituents and the most potent of the agents examined was the O-methyl,N-methyl hydroxamide (R=MeONMe). Although the esters of oleic acid were inactive at 50–100 $\mu$M, oleyl aldehyde proved to be surprisingly effective while its corresponding dimethyl acetal was inactive. Oleyl aldehyde was found to be nearly equipotent with oleamide and the related agent $R=CF_3$ possessing a strongly electrophilic and polarized carbonyl was significantly more potent than oleamide. In contrast, related but less electrophilic ketones ($R=BrCH_2 > ClCH_2$) were substantially less effective. Thus, a smooth trend favoring the more polarized or electrophilic carbonyls was observed. The behavior of the former two agents (R=H, CF$_3$) is especially significant-since they are also potent inhibitors (Ki=190 and 1 nM, respectively) of fatty acid amide hydrolase. Such agents possess dual activities serving both as effective agonists of oleamide and as potent inhibitors of the enzyme responsible for its degradation. Both exhibit a reversible effect on the gap junction inhibition and removal of the media containing the agents and replacement with fresh media restored full gap junction function.

Thus, a range of effective although sterically undemanding substitutions can be made for the carboxamide. To date, the effective inhibitors possess a polarized carbonyl at the C-terminus potentially capable of accepting but not necessarily donating a hydrogen bond.

Oleyl Ethanolamide, Anandamide and Related Structures

An important subset of modified carboxamides is the ethanolamide derivatives (Bachur et al. (1965) *J. Biol. Chem.* 240, 1019–1024; Ramachandran et al. (1992) *Biochem. Arch.* 8, 369–377; Schmid et al. (1990) *Prog. Lipid Res.* 29, 1–43; Hanus et al. (1993) *J. Med. Chem.* 36, 3032–3034). As discussed vida supra, anandamide as well as oleamide were shown to selectively inhibit gap junction communication (dye transfer and electrical coupling) without affecting calcium wave transmission although oleamide was more potent. This effect in glial cells is distinct from the report that anandamide and oleyl ethanolamide not only inhibit gap junction-mediated dye transfer but also block the propagation of astrocyte calcium waves generated either by mechanical stimulation or local glutamate application (Venance et al. (1995) *Nature* 376, 590–594). Consequently, the corresponding ethanolamide of oleic acid and the bis-(ethanol)amides of oleic and arachidonic acid were examined as illustrated in FIG. 4.

Oleamide proved more potent than oleyl ethanolamide and discernibly more potent than anandamide at 20 $\mu$M although both were effective inhibitors at 50 $\mu$M. Although the effective properties of the oleyl ethanolamide (R=HOCH$_2$CH$_2$NH) may suggest it represents an important member of another class of active endogenous agents, it is less potent than oleamide, N-ethyl oleamide (R=CH$_3$CH$_2$NH) which lacks the hydroxyl group, as well as N-propyl oleamide (R=CH$_3$CH$_2$CH$_2$NH) which contains a methyl group in place of the hydroxyl group (FIG. 3).

In addition, oleyl propanolamide exhibited comparable properties. Thus, the hydroxyl group of oleyl ethanolamide does not appear to contribute to its gap junction inhibition properties and may actually diminish them. Similar observations were made in the comparison of arachidonyl amide (R=NH$_2$) and anandamide (R=HOCH$_2$CH$_2$NH) where the latter was less potent. Comparable observations have been made in the examination of anandamide analogs (R=CH3CH2CH2NH>HOCH2CH2NH) with their binding to the CNS cannabinoid receptor. In contrast, the bis-(ethanol)amides were ineffective at inhibiting the gap junction at 50 $\mu$M, and is consistent with their behavior as bulky tertiary amides which exhibit lower activity.

Recent studies have detailed the isolation of 2-arachidonyl glycerol as a potential endogenous cannabinoid receptor agonist (Mechoulam et al. (1995) *Biochem. Pharmacol.* 50, 83–90) and gap junction inhibition by diacylglycerols including 1-oleoyl-2-acetylglycerol in Chinese hamster V79 cells has been disclosed (Aylsworth et al. (1986) *Cancer Res.* 46, 4527–4533). Consequently, we evaluated both racemic and (2S)-1-oleoyl-2-acetylglycerol as potential inhibitors. Consistent with the behavior of simple oleic acid esters (FIG. 3), both were not inhibitors of rat glial gap junction-mediated dye transfer.

Methyl Terminus

From the studies of the fatty acid primary amides, the length of the fatty acid chain did not substantially reduce the gap junction inhibition properties provided it incorporated the key $\Delta$9 cis double bond: 18:1$^9$>20:1$^9$=22:1$^9$=24.1$^9$. This indicates that the methyl terminus can accommodate extensions by a alkyl chain without losing the agonist properties. Similarly, capping the methyl terminus wit a methyl ether (R=CH$_2$OCH$_3$) did not effect the gap junction inhibition. In contrast, the introduction of polar functionality at this site eliminated the inhibitory properties. Thus, the symmetrical 18:1$^9$ dicarboxamide as well as the terminal alcohol and carboxylic acid exhibited no gap junction inhibition at 50 $\mu$M, FIG. 5.

Putative Precursors

In view of the possibility that oleamide may be stored as a N-oleoyl glycinamide derivative whose formation from oleoyl-CoA is catalyzed by acyl-CoA:glycine N-acyltransferase and released upon $\alpha$-hydroxylation of glycine by a peptidylglycine $\alpha$-amidating monooxygenase (PAM) or a closely related enzyme, a set of N-oleoyl glycine derivatives were examined even before the potential of such a process was experimentally verified (Merkler et al. (1996) *Arch. Biochem. Biophys.* 330, 430–434). Both N-oleoyl glycine as well as N-oleoyl glycinamide were ineffective as inhibitors of gap junction-mediated dye transfer, FIG. 6. Thus, a putative storage precursor to oleamide as well as N-oleoyl glycinamide, which is representative of a peptide or protein terminating with an oleoyl glycinamide, failed to inhibit the gap junction. Interestingly, N-oleoyl glycine ethyl ester was an effective, albeit slightly less potent, inhibitor and most likely represents simply another allowable N-substitution on the terminal carboxamide (cf. FIG. 3).

In contrast, N-oleoyl sarcosine as well as its ethyl ester were found to be effective inhibitors. Initially surprising, this observation suggests that the intramolecular hydrogen-bonded rotamer of the free acid or the deprotonated carboxylate which would be observed with N-oleoyl glycine but less favored with N-oleoyl sarcosine, ties up the amide carbonyl disrupting its intermolecular hydrogen bond acceptor capabilities that may be required for gap junction inhibition.

Modifications in the Olefin

Figure 7:
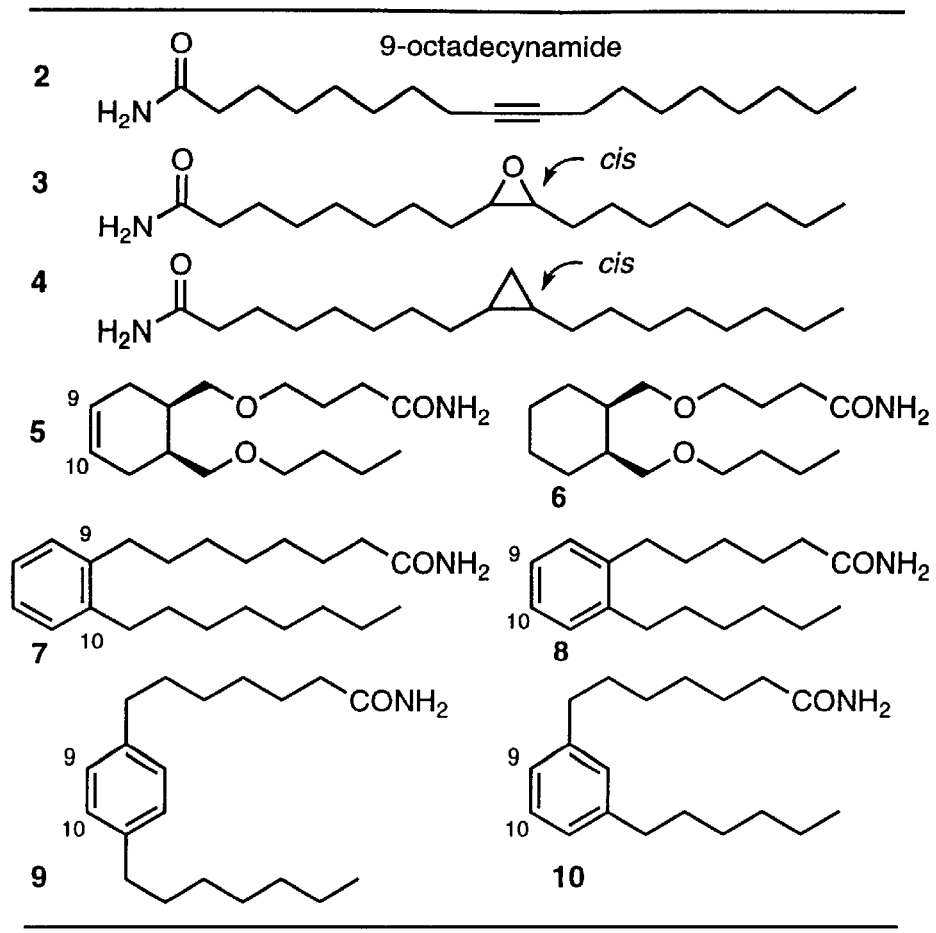
FIG. 7 illustrates olefin modification analogs with W inhibition of gap junction-mediated dye transfer wherein the indicated footnotes are represented as follows: (a) inhibition of GAP junction-mediated dye transfer, see FIG. 2 (b) Not done; (c) Low solubility precluded testing at higher doses; see FIG. 20 for synthetic routes for some of these compounds.

A series of agents 2–8 (FIG. 7) were examined to define the role of the olefin and to provide insights into a conformational dependence on activity (FIG. 7). Thus, while the saturated agent octadecanamide and the trans-9-octadecenamide were ineffective (cf. FIG. 2), 9-octadecynamide (2) was a potent inhibitor being only slightly less active than oleamide. Its conformational characteristics, which more closely resemble those of the inactive 18:0 and 18:19-trans than oleamide, suggest that the appropriate presentation of a n-system in addition to the conformation of the cis olefin may be important. Consistent with this, the epoxide 3 was inactive and the cyclopropane 4 was less active although both may closely mimic the conformational characteristics of oleamide. Although there are a number of plausible explanations for this, 4 may benefit from the partial Π characteristics of the cyclopropane. Alternatively, the incorporation of the epoxide oxygen in 3 may alter the hydrophobic character of the agent and diminish gap junction inhibition. Consistent with either explanation, the agents 5 and 6 proved to be weak inhibitors of the gap junction-mediated dye transfer and 5, which possesses the cis $\Delta$9 double of oleamide was more potent. The removal of the double bond reduced but did not completely eliminate the inhibition properties suggesting an important role for both the Π-character of the double bond as well as its imposed conformational preference for a hairpin conformation. Consistent with this, incorporation of a benzene ring into the structure provided the agents 7–10 that inhibit the gap junction-mediated dye transfer Importantly, 8 was found to be the most potent in the series being nearly equipotent with oleamide and it most closely mimics the hairpin conformation of oleamide. This was followed close by 7 which represents an extended version of 8 and oleamide. contrast, both 9 and 10 were less effective and both mimic alternatives to the hairpin conformation of oleamide.

Modifications in the Linking Chain and Enzyme Inhibitors:

Dual Activities

In the examination of the fatty acid primary amides it was established that increasing or shortening the distance between the carboxamide and cis double bond generally diminished the gap junction inhibition. In addition to these studies, other modifications in the 7 carbon chain linking the olefin and carboxamide were also examined, FIG. 8. The first set of agents contain modifications that should slow the rate of degradation by enzymatic hydrolysis (Maurelli et al. (1995) *FEBS Lett.* 377, 82–86). Both α-methyl oleamide and α,α-dimethyl oleamide were potent inhibitors of the gap junction and both would be expected to be subject to slower FAAH hydrolysis than oleamide. In addition, the agents containing a terminal primary carbamate (X=O) or urethane (X=NH) were also potent inhibitors. The latter is especially interesting since the corresponding urethane of oleyl amine which is two carbons longer in length and whose double bond resides not 9 but 11 carbons from the terminal carbonyl is essentially inactive (FIG. 3). Similarly, α-hydroxy oleamide (X=CHOH), α-chlorooleamide (X=CHCl) and α-acetylthiooleamide (X=CHSAc) were effective inhibitors, although the free thiol (X=CHSH) was ineffective. This latter agent suffers from disulfide formation that may account for its ineffectiveness. The last two agents in FIG. 8 constitute analogs that are effective (Ki=16 and 17 nM, respectively) inhibitors of FAAH. Both serve as oleamide agonists and as inhibitors (Koutek et al. (1994) *J. Biol. Chem.* 269, 22937–22940) of FAAH responsible for its degradation. For both, the gap junction inhibition was reversible and restored to full activity after suspension of the glial cells in fresh media.

EXAMPLE 2

Evidence That Lipid Oleamide Deconvolutes Gap Junction Communication and Calcium Wave Transmission in Glial Cells Oleamide is a sleep-inducing lipid originally isolated from the cerebrospinal fluid of sleep-deprived cats. Oleamide was found to potently and selectively inactivate gap junction mediated communication between rat glial cells. In contrast, oleamide had no effect on mechanically-stimulated calcium wave transmission in this same cell type. Other chemical compounds traditionally employed as inhibitors of gap junctional communication, like heptanol and 18β-glycyrrhetinic acid (18β-GA), blocked not only gap junctional communication, but intercellular calcium signalling as well. Given the central role for intercellular small molecule and electrical signalling in central nervous system function, oleamide-induced inactivation of glial cell gap junction channels may serve to regulate communication between brain cells, and in doing so, may influence higher order neuronal events like sleep induction.

Studies on the molecular mechanisms for cellular interactions have traditionally been hindered by a deficiency of natural products that selectively target specific forms of intercellular communication. One primary mode for direct intercellular contact involves the cell-to-cell transmission of molecules through channels in a specialized cell surface membrane structure, the gap junction (Kumar and Gilula, 1996). Gap junctions allow the passive diffusion of molecules between cells with a selectivity based principally on size, allowing the exclusive movement of molecules smaller than 1000 Da. Such size-selective molecular communication is essential for many forms of multicellular function, including the regulation of events between cells during embryogenesis and the synchronization of cells in the myocardium (Warner et al., 1984 Dewey and Barr, 1962). Previously, we reported the structure determination of a novel, sleep-inducing lipid, 9(Z)-octadecenamide, or oleamide, originally isolated from the cerebrospinal fluid of sleep-deprived cats (Cravatt et al., 1995). In our continued efforts to identify and characterize cellular effects associated with oleamide, we now report that oleamide potently and selectively blocks gap junctional communication in rat glia without altering calcium wave transmission in these cells.

Results: Gap Junction Dye Coupling and Electrical Coupling

Figure 10A:
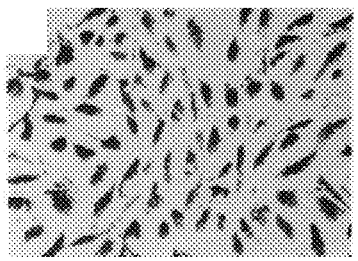
FIG. 10 illustrates oleamide inhibition of gap junction mediated dye coupling between rat glial cells. Cultured rat glial cells (A and D, phase) were microinjected with Lucifer yellow (B and E) and showed efficient dye transfer to adjacent cells under (C) control conditions (0.1% ethanol present in culture media). (F) Treatment of glial cells with 50 µM oleamide for 10 minutes completely blocked dye transfer. Glial cells were also scrape loaded (G, phase) with Lucifer yellow, and under control conditions dye was efficiently transferred from dye loaded cells to adjacent cells (H), with no dye spread to adjacent cells when treated with oleamide (I). Scale bar=50 µm.
Figure 10B:
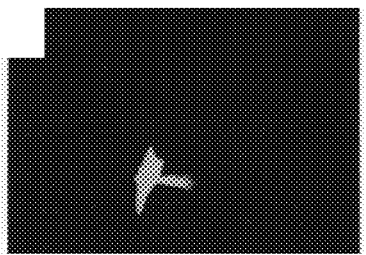
Figure 10C:
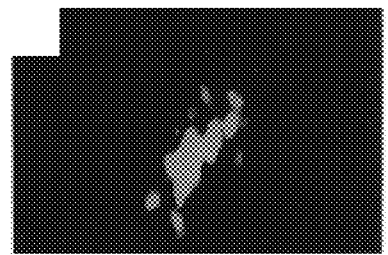
Figure 10D:
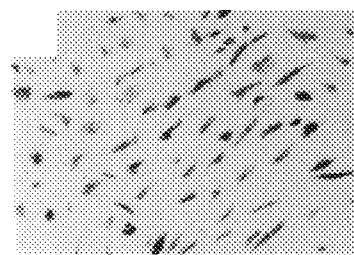
Figure 10E:
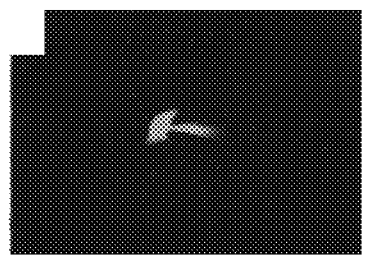
Figure 10F:
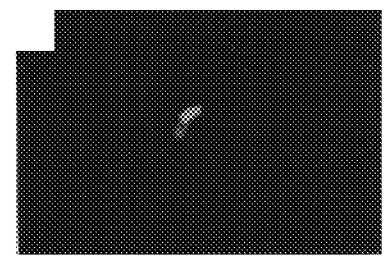
Figure 10G:
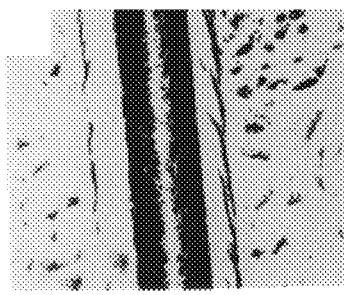
Figure 10H:
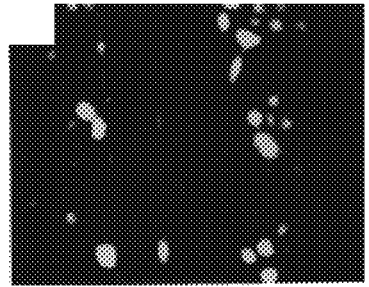
Figure 10I:
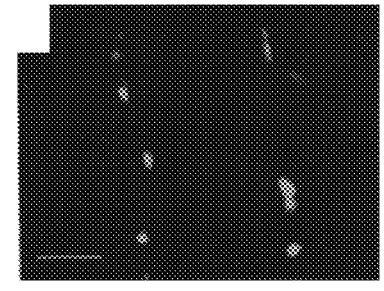
Figures 11J, 11K:
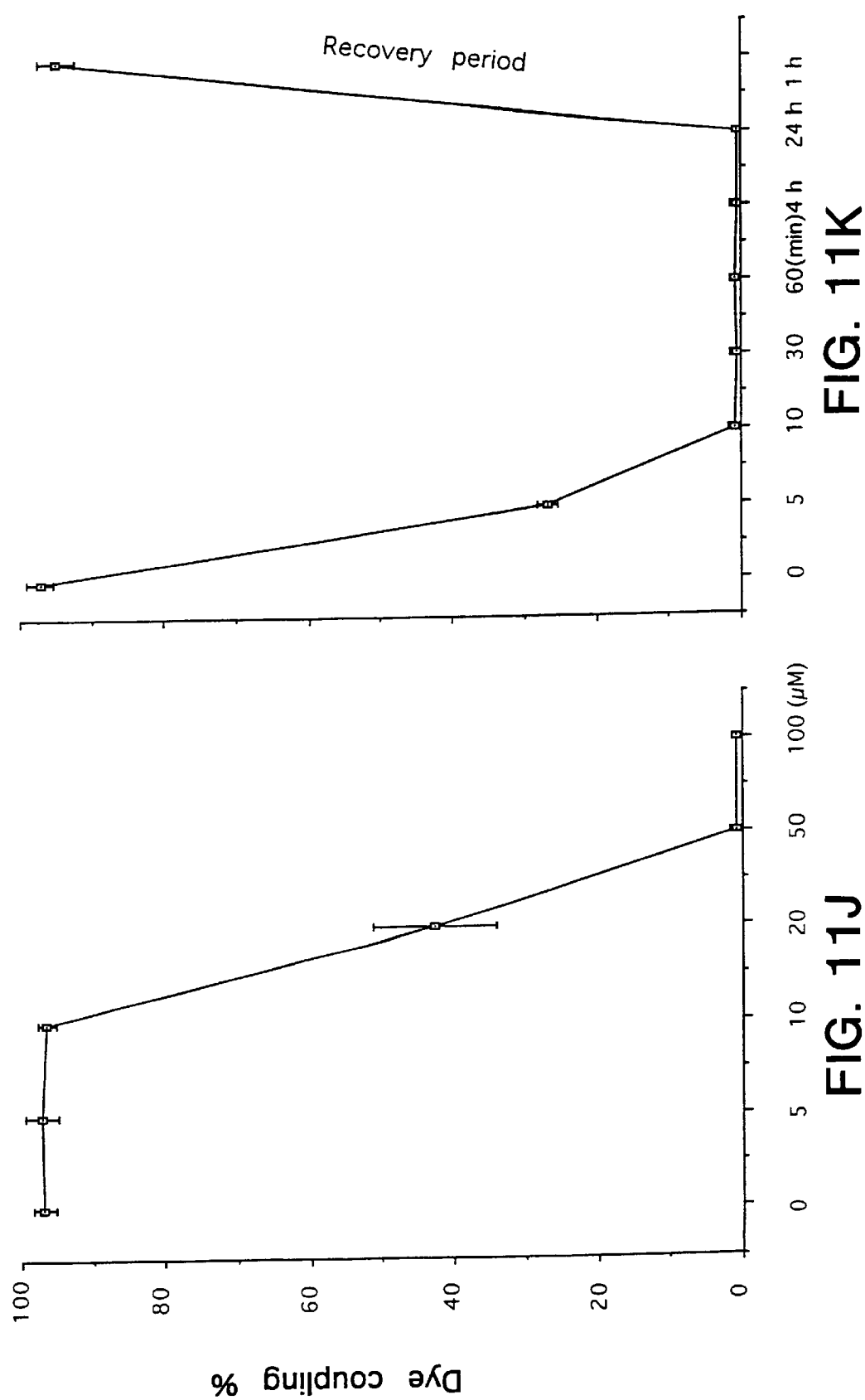
FIG. 11 illustrates: (J) Dose-response studies of oleamide-induced blockage of dye transfer were conducted by treating glial cells with various concentrations of oleamide (5–100 µM) for 4 h prior to injection of Lucifer yellow and monitoring of dye transfer. Approximately 50% inhibition of dye transfer was observed with 20 µM oleamide, and complete inhibition of dye transfer was observed with 50 µM oleamide. (K) Time course of oleamide-induced blockage of gap junction dye transfer was determined by treating glial cells with 50 µM oleamide for indicated times prior to injection of Lucifer yellow. Reversibility of oleamide's effect on gap junctions was established by removing oleamide-containing media from the culture dish, reculturing cells with fresh media without oleamide, and monitoring dye transfer over the subsequent hour. Complete recovery of dye transfer to control levels was observed within one hour after removal of oleamide.
Figure 12A:
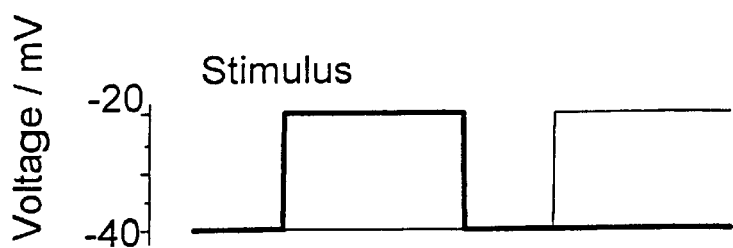
FIG. 12 illustrates double whole cell patch recording combined with observation of dye spread was used to assess gap junctional conductance in cultured rat glial cells. (A) Time course of voltages applied to each cell. Cells were held at −40 mV and first cell 1, then cell 2 was stepped to −20 mV. Thick trace shows voltage applied to cell 1, thin trace the voltage applied to cell 2. (B) and (C), Response of cells to the voltage protocol shown in (A). Thick traces show the currents in cell 1, the thin traces show currents in cell 2. The upward current deflections show the sum of surface membrane and junctional current in the cell whose potential is changed from −40 mV to −20 mV. The upward deflections from 50 msec to 150 msec are currents in cell 1, and the deflections from 200 to 300 msec are currents in cell 2. Downward deflections consist solely of junctional currents recorded in the cell held at −40 mV. In (B), large downward current deflections show a pair of control cells that was well coupled. Note that although the upward deflections elicited by pulsing first one cell, then the other, are different sizes, the downward current deflections, elicited by a 20 mV transjunctional voltage, are of equal size, demonstrating that a driving force of 20 mV produces a constant junctional current regardless of which cell is pulsed. In (C), the lack of downward current deflections in response to a 20 mV pulse shows that a different pair of cells exposed to 50 µM oleamide was completely uncoupled. Panel (D) compares junctional currents of control and experimental cell pairs during the first 150 msec of the measurements shown in (B) and (C). Note that there is no detectable downward deflection in the trace from the cell pair exposed to oleamide. In this case the data set an upper limit on the residual junctional conductance of less than 50 pS. Thus, the junction is completely uncoupled. In measurements carried out on eight cell pairs the mean junctional conductance of control pairs was 13±7 nS (n=3) and the mean junctional conductance of cell pairs exposed to 50 µM oleamide was 0.5±0.7 nS (n=5).
Figure 12B:
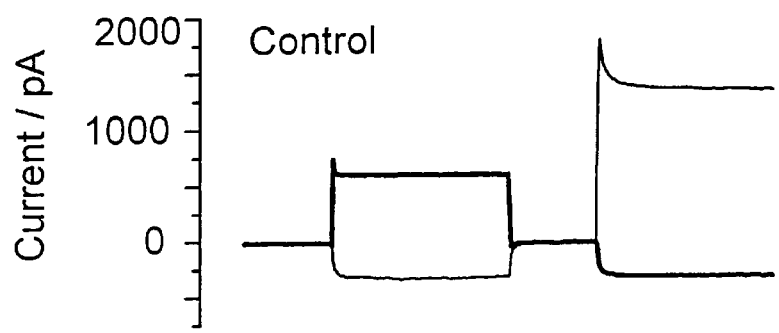
Figure 12C:
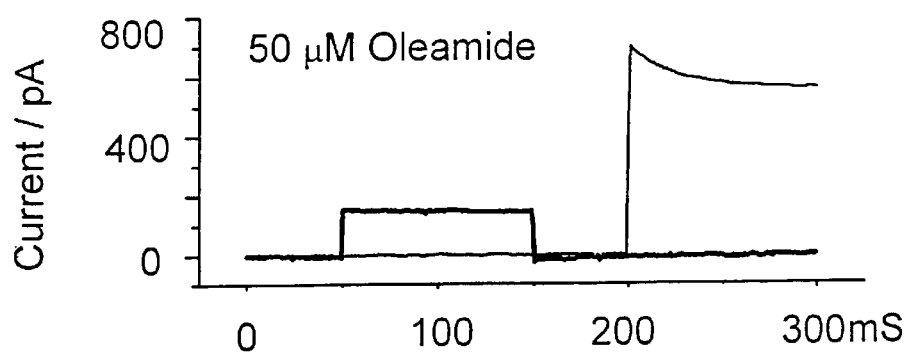
Figure 12D:
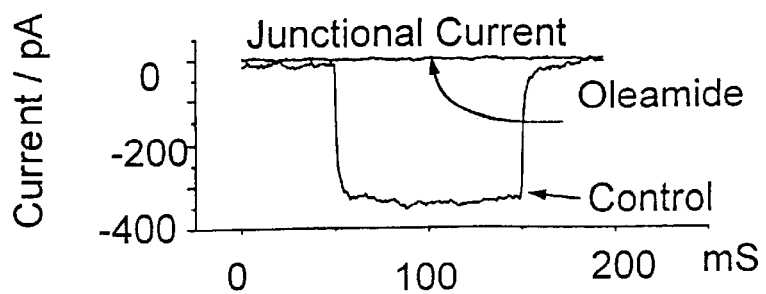

Gap junction mediated intercellular communication in cultured rat glial cells was evaluated by microinjection and scrape-loading (El-Fouly et al. (1987) Expl. Cell Res. 168, 422–430.) of the fluorescent dye, Lucifer yellow. While under control conditions microinjected glial cells demonstrated strong dye coupling as monitored by intercellular Lucifer yellow diffusion (FIGS. 10A–10C), pretreatment of these cells with 50 μM oleamide for 10 min completely blocked intercellular dye transfer (FIGS. 10D–10F). Likewise, glial cells scrape-loaded with Lucifer yellow showed significant dye transfer that was fully abrogated by pretreatment with oleamide (FIGS. 10G–10I) Dose response and time course studies of oleamide-induced inhibition of dye transfer were conducted (FIGS. 11J–11K, respectively). Lower doses of oleamide (20 μM) also significantly inhibited glial cell dye transfer, but longer preincubation times (4 h) were required. Oleamide's effects or gap junction permeability proved stable and completely reversible. Thus, whereas no restoration of dye-coupling was observed in glial cells that were continually exposed to oleamide for up to 24 h, once oleamide was removed by changing the culture media, junctional communication recovered to control levels within 1 h (see FIG. 10K, recovery).

As an additional measure of oleamide's effect on gap junction permeability, glial cell gap junctional conductance was examined in the presence of oleamide by using the double whole-cell recording technique (FIG. 12). Consistent with its effect on gap junction-mediated dye transfer, oleamide (50 μM) completely blocked junctional electrical coupling in glial cells.

Structure-Activity Relationship

Figure 13:
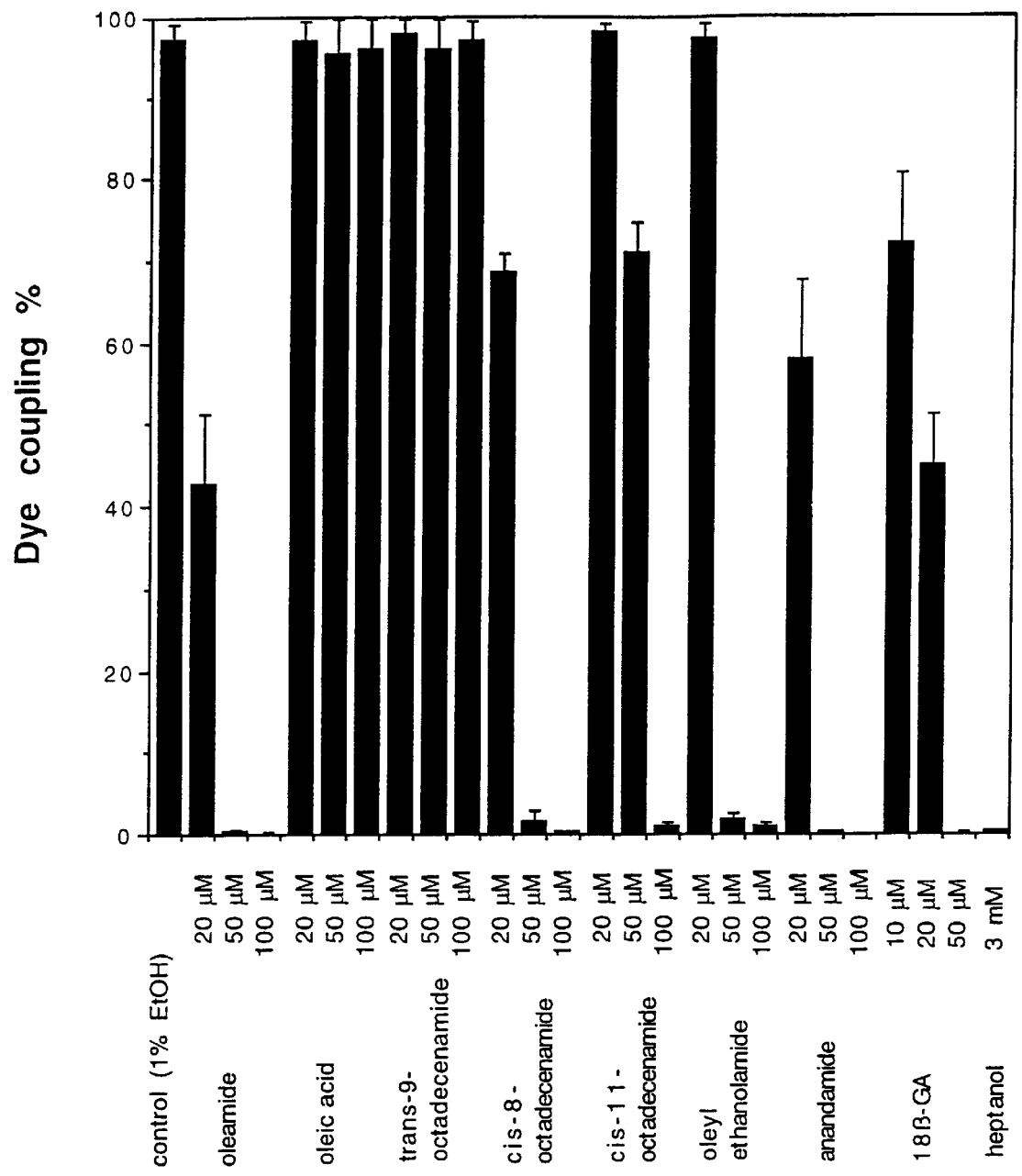
FIG. 13 illustrates structure-activity studies of oleamide-induced blockage of gap junction dye transfer were conducted to evaluate which chemical features of oleamide were required for its inhibitory effect. Oleic acid and trans-9-octadecenamide had no effect on dye transfer, while of the remaining cis-monounsaturated fatty acid amides, oleamide proved to be the most potent inhibitor. Following oleamide in order of potency were: cis-8-octadecenamide>oleyl ethanolamide>cis-11-octadecenamide. Oleamide was also compared to other gap junction inhibitors, anandamide, 18β-GA and heptanol.

To evaluate oleamide's structure-activity relationship, several chemical analogs were synthesized (Cravatt et al. (1996) *J. Am. Chem. Soc.* 118, 580–590) and tested for their ability to block gap junction permeability (FIG. 13). In contrast to oleamide, oleic acid and trans-9-octadecenamide showed no effect on glial cell dye coupling, even at higher doses. Interestingly, oleic acid has previously been demonstrated to inhibit gap junction communication in rat cardiac myocytes, which like rat glia, express the α1 connexin (Cx43), indicating that the response of the glial cells selectively to oleamide is likely a function of cell type rather than the primary structure of the α1 connexin. Other cis-monounsaturated fatty acid amides, in addition to oleamide, demonstrated varying degrees of inhibition. 50 μM Cis-11-octadecenamide only slightly affected junctional coupling, but at 100 μM levels, the compound completely blocked dye transfer. Oleyl ethanolamide and cis-8-octadecenamide were significant inhibitors of dye transfer at 50 μM levels, but proved less potent than oleamide at lower doses. Thus, the key chemical features of oleamide that impart upon th compound its inhibitory properties appear to be the amide functionality and the cis-double bond, with discernible preference exhibited for a primary amide moiety and location of the degree of unsaturation at the Δ9 position along the alkyl chain. Oleamide's effect on glial cells was also compared to the activity of other established inhibitors of gap junction communication. Both 18β-GA and anandamide blocked dye transfer at doses comparable to oleamide, while much higher concentrations of heptanol (3 mM) were required to inhibit junctional communication (FIG. 13).

Oleamide Effects on β1 Connexin-Transfected BHK Cells

Figure 14A:
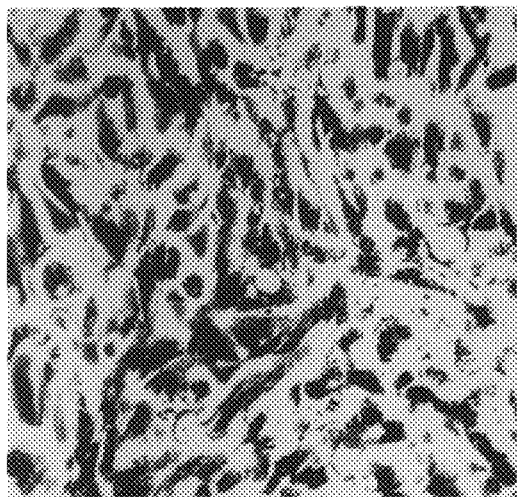
FIG. 14 illustrates oleamide effect on gap junction dye transfer between BHK/β1 cells. In the presence of zinc induction, BHK/β1 cells (A and C, phase) were microinjected with Lucifer yellow and showed efficient dye transfer to adjacent cells in the control condition (B) (with 0.1% ethanol in culture media) and no dye transfer between cells that were treated with oleamide (D) (50 µM oleamide for 10 min).
Figure 14B:
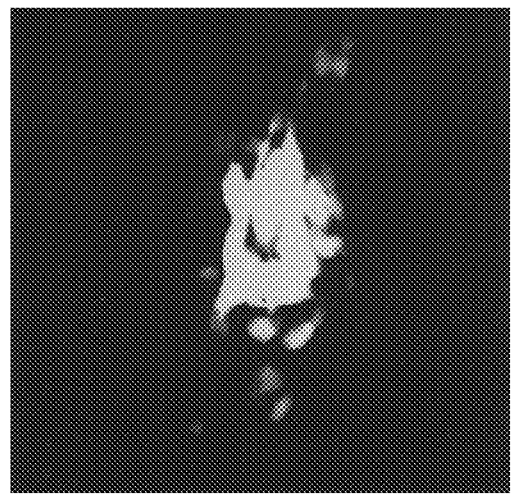
Figure 14C:
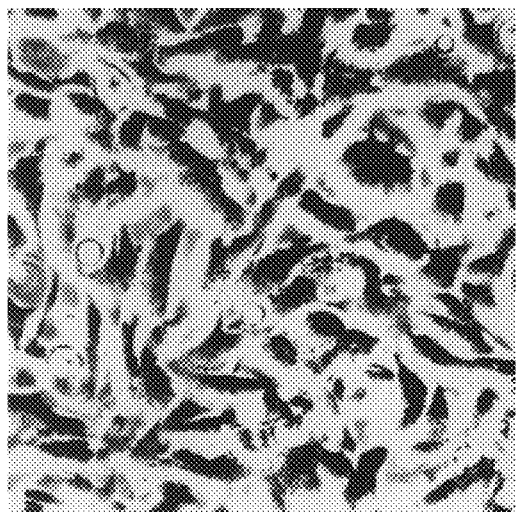
Figure 14D:
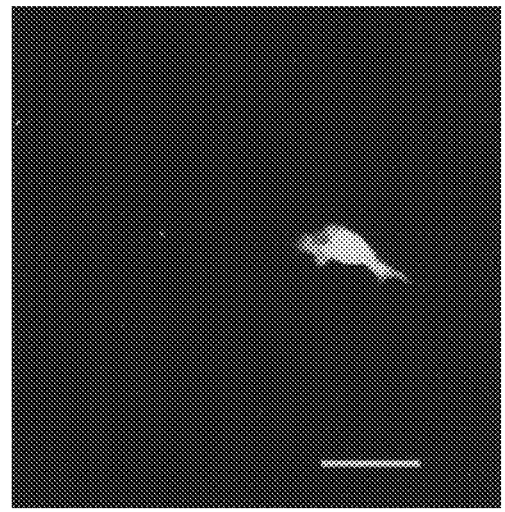
Figure 15E:
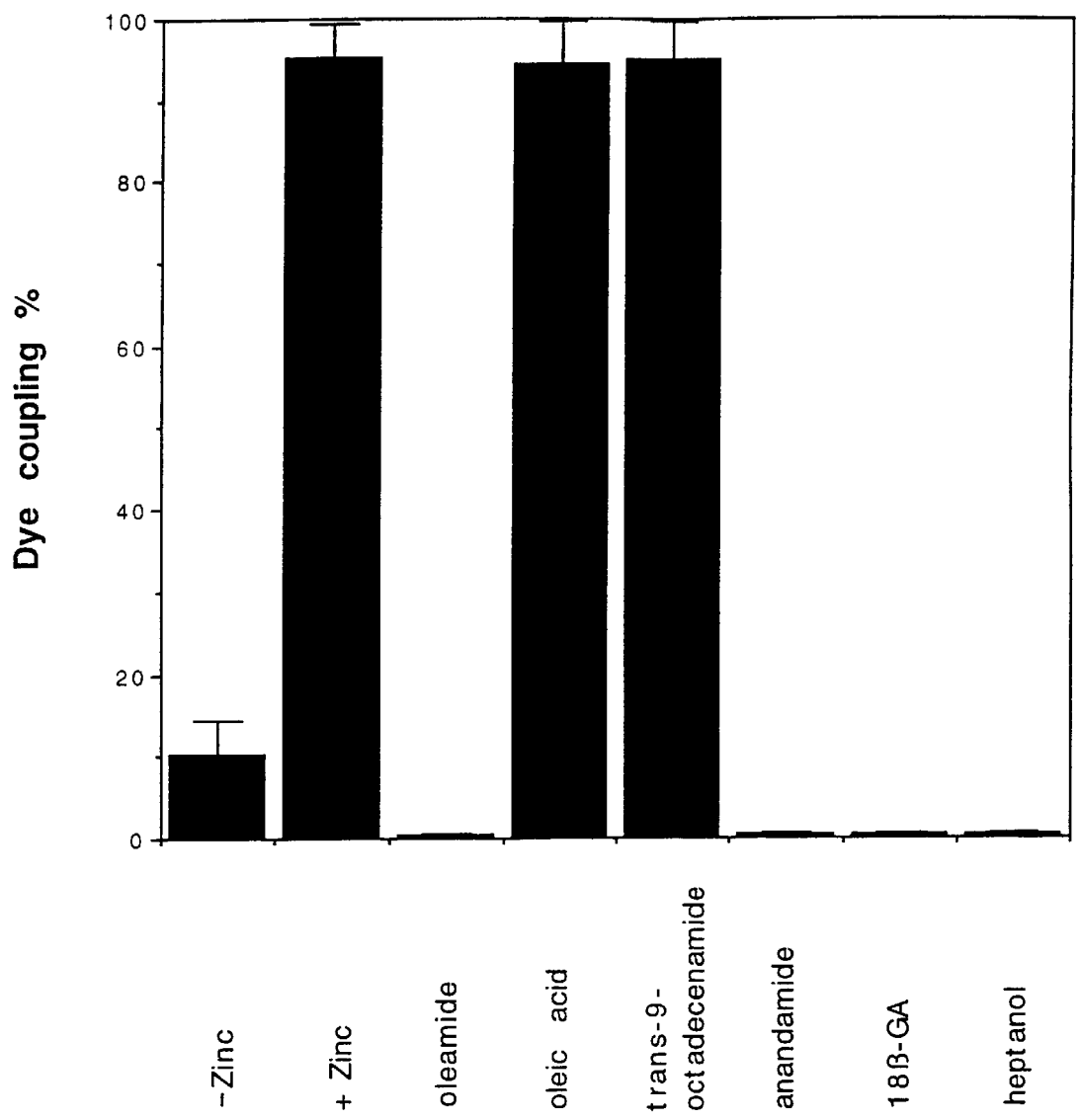
FIG. 15 illustrates: (E) Comparison of dye transfer rate between BHK/β1 cells under different treatment conditions. BHK/β1 cells without zinc induction had a low incidence (10.2+4.2%) of dye transfer. After adding zinc to the culture medium for 8–18 hr, dye transfer was significantly increased (95+4.5%). 50 μM oleamide completely blocked dye transfer (0.31+0.24%) in the zinc induced sample. Anandamide (50 μM), 18β-GA (50 μM), and heptanol (3 mM) showed similar inhibition, while oleic acid (50 μM) and trans-9-octadecenamide (50 μM) had no effect on dye transfer (E). All determinations were made following 4 hours of treatment. Scale bar=50 μM.

To evaluate whether oleamide's effect on α1 containing gap junctions was specific to the α1 junctional type, we determined dye transfer properties in BHK cells that were transfected with β1 connexin to produce β1 containing gap junctions. For this analysis, the same assay conditions were applied that were used for the rat glial cell measurements. 50 μM Oleamide was found to rapidly and completely block dye transfer (FIG. 14D) between BHK/β1 cells, while oleic acid and trans-9-octadecenamide showed no effect (FIG. 14E). Other inhibitory compounds, like anandamide, 18β-GA, and heptanol had inhibitory effects on dye transfer between the BHK/β1 cells that were very similar to those observed in the rat glial cells (compare FIG. 15E and FIG. 13).

Gap Junctional Intercellular Communication and the Calcium Wave

Figure 16A:
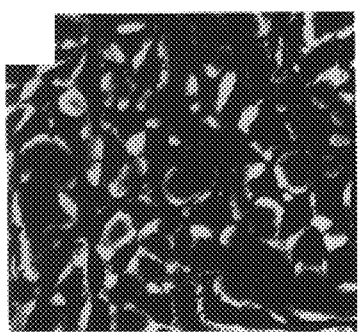
FIG. 16 illustrates effect of oleamide and 18β-GA on calcium wave propagation in rat glial cells. Rat glia (phase, A) were loaded with the calcium-indicator dye, Fluo-3, and changes in the intracellular free calcium concentration ([Ca2+]i) were documented as changes in the intensity of fluorescent dye both prior to (B) and after (C-F) mechanical stimulation. Fluorescence changes were monitored with an inverted fluorescence microscope. In the presence of 40 μM 18β-GA (incubated with glia for 10 minutes prior to mechanical stimulation), mechanical stimulation resulted in an increase in [Ca2+]i in the stimulated cell, but this [Ca2+]i change did not propagate to any other cells (C). In contrast, in rat glia treated with 50 μM oleamide (preincubation from 10 minutes to 4 hours) mechanical stimulation produced an increase in [Ca2+]i that was rapidly propagated to cells at long distances in an indistinguishable manner from control cell populations (D-F, time course of wave propagation; D, 2 sec; E, 4 sec; F, 8 sec). Scale bar=30 μm. For a quantitative comparison of calcium wave propagation in cells treated by different agents and control cell populations, see FIG. 9.
Figure 16B:
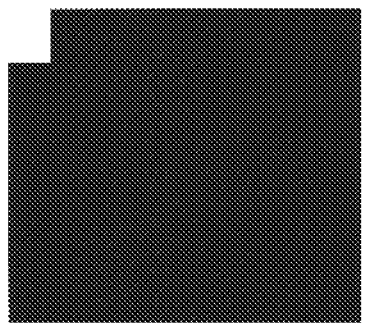
Figure 16C:
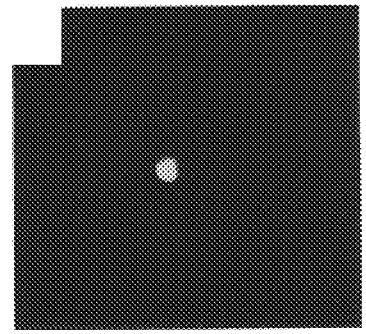
Figure 16D:
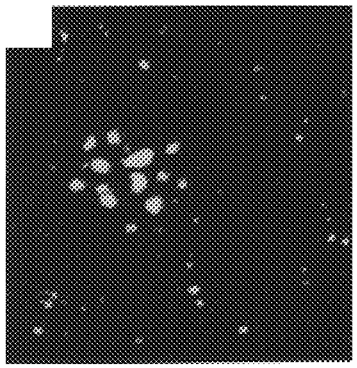
Figure 16E:
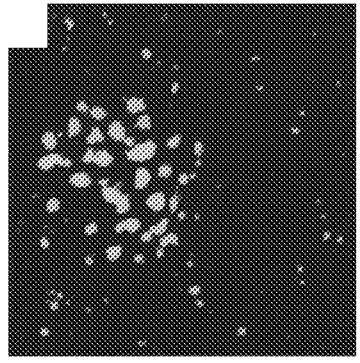
Figure 16F:
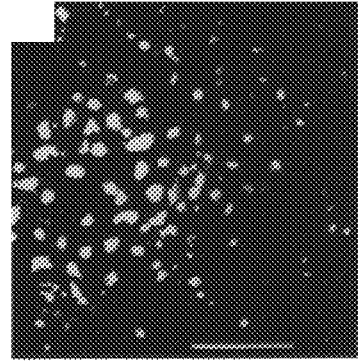

Since calcium waves in brain cell populations can propagate in a gap junction-dependent manner, we next evaluated oleamide's effect on calcium wave transmission among glial cells. Using the intracellular calcium indicator Fluo-3, to monitor changes in intracellular calcium levels within the glial cell population, we found that 50 μM oleamide had no impact on mechanically-induced calcium wave propagation (FIG. 16D–16F and FIG. 9). Intrigued by oleamide's contrasting effects on gap junction communication and calcium wave transmission, we compared oleamide's properties to other gap junction inhibitors 18β-GA (40 μM) and heptanol (3 mM) showed no discrimination in their inhibitory activity, completely blocking both dye transfer and calcium wave propagation in glial cells (FIG. 16C and FIG. 9). In contrast, we found that anandamide, an amidated lipid like oleamide, resembled oleamide in activity, selective inhibiting gap junction communication (dye transfer and electrical coupling) without affecting calcium wave transmission (FIG. 9).

In mammary gland cells, mast cells, and insulin-secreting cells calcium waves have been shown to propagate by a process dependent on extracellular release of ATP from the stimulated cell. To examine whether glial cells also transmitted ATP-dependent calcium waves, the glia were treated with the P2-purinergic receptor antagonist, suramin, and subsequently tested for calcium wave transmission. As shown in FIG. 9, suramin (200 μM) blocked glial calcium wave transmission without affecting gap junction communication in these cells. Co-treatment of the glia with suramin and oleamide produced the combined phenotype of blocked calcium wave transmission and blocked gap junction communication, further supporting the notion that the two pathways for these interglial interactions are distinct and separate.

Changes of α1 Connexin Phosphorylation

Figure 17:
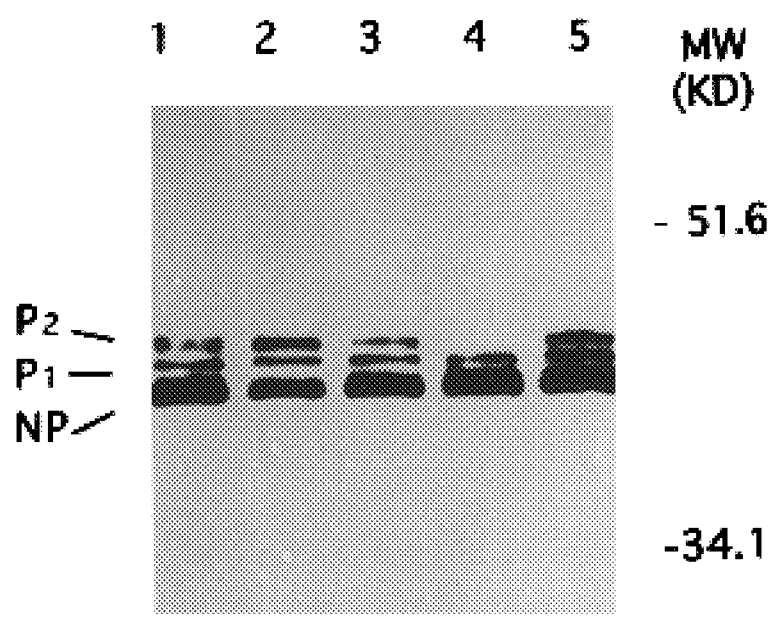
FIG. 17 illustrates western blot analysis of the α1 connexin protein from glia treated with oleamide and its inactive structural analogs. Lane 1 contains a sample of control cells treated with 0.1% ethanol for 4 hours. Lanes 2–4 contain samples of cells treated for 4 hours with 50 μM oleic acid, 50 μM trans-9-octadecenamide, and 50 μM oleamide, respectively. The loss of P2 α1 in glia treated with oleamide was reversible, as P2 was present at control levels after removal of oleamide from the culture dish and culturing the cells in normal culture media for 4 hours (lane 5). The nonphosphorylated (NP) and phosphorylated (P1 and P2) α1 connexin isoforms and molecular weight standards are indicated on the right of the blot.

In an effort towards defining the molecular mechanism of oleamide's action on gap junctions, we examined the phosphorylation profile of the α1 connexin in glial cells upon treatment with oleamide. The α1 connexin has previously been shown by Western blotting to exist in three distinguishable isoforms: nonphosphorylated, NP (~42 kD), and two phosphorylated isoforms, P1 (~44 kD), and P2 (~46 kD). Upon exposure to oleamide (50 μM), glial cells demonstrated a dramatic loss of the P2 isoform with no discernible change in the levels of P1 and NP (FIG. 17, lane 4). The effect of oleamide on the α1 phosphorylation profile proved reversible, as removal of oleamide from the glial cell culture media was associated with a restoration of P2 to control levels (FIG. 17, lane 5). No change in the α1 phosphorylation profile was detected in glial cells exposed to oleic acid or trans-9-octadecenamide (FIG. 17, lanes 2–3), two oleamide analogs which did not inhibit gap junction communication.

Discussion

The sleep-inducing lipid, oleamide, exhibits the special capacity to block gap junction communication in glial cells as monitored by dye transfer and electrical conductance without inhibiting intercellular calcium wave transmission in these same cells. Additionally, oleamide induces a dramatic change in the phosphorylation profile of the α1 connexin protein, the principle component of the glial cell gap junction channels. The loss of both gap junction permeability and α1 connexin P2 in the presence of oleamide is consistent with previous work indicating that the P2 connexin isoform is associated with the formation of functional gap junction plaques. However, the precise causal relationship between oleamide-induced gap junction blockage and the loss of the connexin phosphorylated P2 isoform remains uncertain, and this must be examined in more detail to determine if there is a specific association between the two events.

The observation that calcium waves can propagate in glial cells when gap junction communication pathways have been eliminated implies that calcium waves in these cells need not, as previously suggested, be exclusively dependent on gap junctional communication. The precise relationship between these observations and previously reported studies on gap junction associated calcium waves remains to be clarified. However, our observation that suramin, a P2-purinergic receptor antagonist, blocked calcium wave transmission in glial cells without affecting gap junction communication suggests that these cells may transmit intercellular calcium signals by an ATP-dependent mechanism akin to those previously reported for mammary gland cells), mast cells, and insulin-secreting cells Interestingly, the realization that intercellular calcium waver in glial cells can persist without functional gap junctions may help to explain the presence of calcium waves in certain tissues like the retina, where thus far, gap junctional pathways have not been definitively described among all cell types that participate in transmission of the wave).

In the course of studying oleamide's effect on gap junction communication, we also accumulated evidence that previously identified gap junction inhibitors, such as 18β-GA and heptanol, are not selective in their inhibitory activity on gap junction channels, but rather appear to act as more general nonspecific perturbants of the plasma membrane and its corresponding functions. Since medium chain alcohols and glycerrhetinic acid derivatives are often used as tools for specifically studying the gap junctions, we would suggest that, in the future, their biological effects be evaluated in the context of the entire cell. Otherwise, the role of gap junctions in complex cellular phenomena like calcium wave transmission may remain obscure.

Although it is not possible yet to determine the precise mechanism that oleamide uses to exert its effect on gap junction channels, the results from this initial analysis indicate that oleamide will block gap junction channels that contain different connexins [α1] connexin, β1 connexin, and a C-terminal truncated mutant of α1. Based on these observations, it is reasonable to consider the possibility that oleamide exerts its action on some generalized structural property of the connexin oligomers or channels in the lipid bilayer. Such a mechanism of action would not be dependent on the integrity of the carboxy terminal domain or other diverse primary sequence properties that exist between the members of the connexin multigene family. In this context, oleamide and related molecules such as anandamide, should prove to be very useful reagents, serving as more specific probes for determining the function of gap junction channels in vivo than the relatively non-specific reagents that have been previously applied, such as heptanol and glycerrhetinic acid. Furthermore, although oleamide can block gap junction channels that are comprised of different connexins, there appears to be a cell specific property in determining the effect of oleamide on gap junction channels. For example, in a preliminary analysis (Guan et al., unpublished observations), we have observed that the gap junctional communication property between mammalian myocardial cells is not as sensitive to the inhibitory action of oleamide as the gap junction channels are in other mammalian cell types, a result that is very consistent with a previous report on arachidonimide treatment of cultured rat myo cardial cells. Hence, such cell-specific responses to bioactive lipids, such as oleamide, may be extremely beneficial for protecting the myocardium from the effects of such molecules in vivo.

Finally, by blocking gap junction permeability in glial cells, oleamide may be expected to exert intricate modulatory effects on brain function and physiology, preserving certain glial, and perhaps also glial-neuronal, forms of cell-cell interaction, like calcium wave transmission, in the absence of the chemical and electrical forms of intercellular contact mediated by gap junctions. The precise mechanism by which oleamide exerts its profound effect on gap junction channels is unknown. The structure of the truncated α1 connexin channel is altered after treatment with oleamide. Finally, in addition to the potential direct interaction with the assembled gap junction or its associated proteins, a most intriguing possibility is that oleamide functions by perturbing the lipid environment of membrane proteins and organelles, thus representing a new class of biologically active lipids that act as fluidity transmitters.

Synthetic Protocals

General $^1$H and $^{13}$C nmr spectra were recorded either on a Bruker AM-250, a Bruker AMX-400 or a Bruker AMX-500 spectrometer. Residual protic solvent CHCl$_3$ ($\delta_H$=7.26 ppm, $\delta_C$=77.0), d$_4$-methanol ($\delta_H$=3.30 ppm, $\delta_C$=49.0) and D$_2$O ($\delta_H$=4.80 ppm, $\delta_C$ (of $\underline{C}$H$_3$CN)=1.7 ppm) or TMS ($\delta_H$=0.00 ppm) were used as internal reference. Coupling constants were measured in Hertz (Hz). HRMS were recorded using FAB method in a m-nitrobenzylalcohol (NBA) matrix doped with NaI or CsI. Infra-red spectra were recorded on a Perkin-Elmer FTIR 1620 spectrometer. Enantiomeric excess was determined by HPLC using a Daicel Chemical Industries CHIRALPAK AD column. Optical rotations were measured with an Optical Activity AA-1000 polarimeter. Melting points were taken on a Thomas Hoover capillary melting point apparatus and are uncorrected. Column chromatography was performed on Merck Kieselgel 60 (230–400 mesh). Analytical thin layer chromatography was performed using pre-coated glass-backed plates (Merck Kieselgel F$_{254}$) and visualized by cerium molybdophosphate or ninhydrin. Diethyl ether, tetrahydrofuran (THF) and toluene (PhCH$_3$) were distilled from sodium-benzophenone ketyl, dichloromethane (DCM) and acetonitrile from calcium hydride. Other solvents and reagents were purified by standard procedures if necessary. TLC was performed on precoated Kieselgel 60 F$_{254}$ plates (Merck). Column chromatography was carried out on Kieselgel 60 (70–230 mesh and 230–400 mesh) and MCI gel CHP-20P (Mitsubishi Chemical, Ind.).

Unless otherwise described, all starting reagents were purchased from Aldrich, Acros, or Sigma.

18:0 (Stearamide) as Illustrated in FIG. 2

Purchased from Aldrich and recrystallized once before use.

General Procedure For the Preparation of Fatty Amides

The fatty acid (1 equiv) was dissolved in dry CH$_2$Cl$_2$ (0.2 M) and cooled to 0° C. under a N$_2$ atmosphere. Oxalyl chloride (2M in CH$_2$Cl$_2$, 3 equiv) was added slowly. The solution was warmed to 25° C. and allowed to stir for 3 h in the dark. The solvent was removed in vacuo and the flask cooled to 0° C. Excess concentrated NH$_4$OH (for 15: ethanolamide was used) was added slowly and the crude product was purified by chromatography on SiO$_2$ using EtOAc/hexanes as an eluent. Fatty acids were purchased from Sigma unless otherwise indicated.

14:1$^9$(Myristoleamide) as Illustrated in FIG. 2

Synthesized exactly as found in the general procedure vida supra; all starting reagents were purchased from Aldrich, Acros, or Sigma and resulting white solid was purified by chromatography (50%–100% EtOAc/hexanes, gradient elution) to afford 94% desired product: mp 76–78° C.; $^1$H NMR (CD$_3$OD, 400 MHz) δ5.29–5.22 (m, 2H), 2.11 (t, 2H, J=7.6 Hz), 1.95 (m, 4H), 1.52 (p, 2H, J=7.3 Hz, 1.25 (m, 12H), 0.83 (m, 3H); $^{13}$C NMR (CD$_3$OD, 100 MHz) δ179.3, 130.82, 130.77, 36.6, 33.1, 30.8, 30.5, 30.3, 30.2, 28.1, 27.9, 26.9, 23.4, 14.4; IR (NaCl, film) υ$_{max}$ 3324, 2923, 2852, 2523, 2466, 2355, 1630, 1526, 1469, 1435, 1410, 1095, 956, 755, 723 cm$^{-1}$; HRFABMS m/z (M+H$^+$) 226.2164 (requires m/z 226.2171).

16:1$^9$(Palmitoleamide) as Illustrated in FIG. 2

Synthesized exactly as found in the general procedure vida supra; all starting reagents were purchased from Aldrich, Acros, or Sigma and resulting white solid was purified by chromatography (50% EtOAc/hexanes) to afford 96% desired product: mp 74–75° C.; $^1$H NMR (CD$_3$OD, 400 MHz) δ5.30–5.22 (m, 2H), 2.11 (t, 2H, J=7.6 Hz), 1.94 (m, 4H), 1.53 (p, 2H, J=7.1 Hz), 1.25 (m, 16H), 0.82 (t, 3H, J=6.8 Hz); $^{13}$C NMR (CD$_3$OD, 100 MHz) δ179.3, 130.9, 130.8, 36.5, 33.0, 30.8 (2), 30.4, 30.34 (2), 30.27, 30.1, 28.2, 26.8, 23.7, 14.5; IR (NaCl, film) υ$_{max}$ 3324, 3003, 2923, 2852, 2523, 2466, 2357, 1631, 1527, 1469, 1437, 1410, 1215, 758 cm$^{-1}$; HRFABMS m/z (M+Cs$^+$) 386.1448 (requires m/z 386.1460).

17:1$^8$ as Illustrated in FIG. 2

Synthesized exactly as found in the general procedure vida supra; all starting reagents were purchased from Aldrich, Acros, or Sigma and resulting white solid was purified by chromatography: white solid: mp 68–69° C.; $^1$H NMR (CDCl$_3$, 400 MHz) δ5.64 (br, 1H), 5.43 (br, 1H), 5.38–5.26 (m, 2H), 2.19 (t, 2H, J=7.6 Hz), 2.03–1.95 (m, 4H), 1.62 (m, 2H), 1.37–1.24 (m, 18H), 0.85 (t, 3H, J=6.9 Hz); $^{13}$C NMR (CDCl$_3$, 100 MHz) δ175.6, 130.2, 129.4, 35.9, 31.9, 29.7, 29.5, 29.4, 29.3, 28.8, 27.2, 27.0, 25.4, 22.7, 14.1; IR (film) υ$_{max}$ 3359, 3193, 2922, 2852, 1659, 1633, 1466, 1412, 1136 cm$^{-1}$; FABHRMS (NBA-CsI) m/z 400.1603 (C$_{17}$H$_{33}$NO+Cs$^+$ requires 400.1616).

8Z-heptadecenoic acid prepared as previously described (JACS, 1996, 118, 5938–5945).

18:1[6] (Petroselinamide) as Illustrated in FIG. 2

Synthesized exactly as found in the general procedure vida supra; all starting reagents were purchased from Aldrich, Acros, or Sigma and resulting white solid was purified by chromatography: white solid: mp 73–74° C.; $^1$H NMR (CDCl$_3$, 500 MHz) δ6.15 (br, 1H), 5.61 (br, 1H), 5.34–5.27 (m, 2H), 2.17 (t, 2H, J=7.5 Hz), 2.01 (q, 2H, J=7.0 Hz), 1.96 (q, 2H, J=7.0 Hz), 1.60 (p, 2H, J=7.8 Hz), 1.35 (p, 2H, J=7.8 Hz), 1.28–1.21 (m, 18H), 0.83 (t, 3H, J=7.0 Hz); $^{13}$C NMR (CDCl$_3$, 125 MHz) δ175.9, 130.4, 129.0, 35.8, 31.9, 29.7, 29.62, 29.59, 29.5, 29.3, 29.2, 27.2, 26.8, 25.1, 22.6, 14.1; IR (film) $\upsilon_{max}$ 3366, 3203, 3000, 2917, 2848, 1647, 1465, 1415, 734 cm$^{-1}$; FABHRMS (NBA-CsI) m/z 282.2810 (C$_{18}$H$_{35}$NO+H$^+$ requires 282.2797).

18:1[7] as Illustrated in FIG. 2

Synthesized exactly as found in the general procedure vida supra; all starting reagents were purchased from Aldrich, Acros, or Sigma and resulting white solid was purified by chromatography: white solid: mp 70–71° C. $^1$H NMR (CDCl$_3$, 400 MHz) δ6.26 (br, 1H), 5.67 (br, 1H), 5.34–5.24 (m, 2H), 2.16 (t, 2H, J=7.6 Hz), 2.00–1.92 (m, 4H), 1.58 (p, 2H, J=7.5 Hz), 1.31–1.21 (m, 20H), 0.83 (t, 3H, J=6.8 Hz); $^{13}$C NMR (CDCl$_3$, 100 MHz) δ176.1, 130.1, 129.3, 35.9, 31.8, 29.7, 29.6 (2), 29.5, 29.4, 29.3, 29.2, 28.8, 27.1, 27.0, 25.4, 22.6, 14.0; IR (film) $\upsilon_{max}$ 3392, 3179, 3013, 2920, 2848, 1647, 1468, 1416, 1312, 1115, 806, 719, 628 cm$^{-1}$; FABHRMS (NBA-NaI) m/z 282.2801 (C$_{18}$H$_{35}$NO+H$^+$ requires 282.2797).

18:1[8] as Illustrated in FIG. 2

Synthesized exactly as found in the general procedure vida supra; all starting reagents were purchased from Aldrich, Acros, or Sigma and resulting white solid was purified by chromatography or prepared as previously described exactly (JACS, 1996, 118, 580–590).

18:1[9] (Oleamide) as Illustrated in FIG. 2

Prepared as previously described exactly (JACS, 1996, 118, 580–590).

18:1[9trans] (Elaidamide) as Illustrated in FIG. 2

Prepared as previously described. (JACS, 1996, 118, 580–590).

18:1[11] (Vaccenamide) as Illustrated in FIG. 2

Prepared as previously described. (JACS, 1996, 118, 580–590).

18:1[12] as Illustrated in FIG. 2

Synthesized exactly as found in the general procedure vida supra; all starting reagents were purchased from Aldrich, Acros, or Sigma and resulting white solid was purified by chromatography: white solid: mp 77–78° C.; $^1$H NMR (CDCl$_3$, 500 MHz) δ6.11 (br, 1H), 5.62 (br, 1H), 5.34–5.26 (m, 2H), 2.16 (t, 2H, J=7.5 Hz), 1.97 (q, 4H, J=6.0 Hz), 1.58 (p, 2H, J=7.3 Hz), 1.32–1.22 (m, 20H), 0.84 (t, 3H, J=7.0 Hz); $^{13}$C NMR (CDCl$_3$, 125 MHz) δ176.1, 129.84, 129.78, 35.9, 31.5, 29.7, 29.51, 29.46, 29.42, 29.38, 29.3, 29.23, 29.18, 27.1, 25.5, 22.5, 14.0; IR (film) $\upsilon_{max}$ 3356, 3188, 2917, 2848, 1727, 1661, 1633, 1469, 1410, 1135, 700, 628 cm$^{-1}$; FABHRMS (NBA-CsI) m/z 282.2810 (C$_{18}$H$_{35}$NO+H$^+$ requires 282.2797)

18:1[13] as Illustrated in FIG. 2

Synthesized exactly as found the general procedure vida supra; all starting reagents were purchased from Aldrich, Acros, or Sigma and resulting white solid was purified by chromatography: white solid: mp 86–87° C.; $^1$H NMR (CDCl$_3$, 400 MHz) δ6.03 (br, 1H), 5.57 (br, 1H), 5.34–5.27 (m, 2H), 2.17 (t, 2H, J=7.6 Hz), 1.98 (m, 4H), 1.58 (p, 2H, J=7.2 Hz), 1.30–1.22 (m, 20H), 0.86 (t, 3H, J=7.0 Hz); $^{13}$C NMR (CDCl$_3$, 100 MHz) δ176.0, 129.82, 129.78, 35.9, 31.9, 29.7, 29.55 (2), 29.48, 29.4, 29.3, 29.24, 29.19, 27.2, 26.8, 25.5, 22.3, 13.9; IR (film) $\upsilon_{max}$ 3357, 3192, 3003, 2917, 2848, 1656, 1632, 1470, 1422, 1410, 1136, 721, 636 cm$^{-1}$; FABHRMS (NBA-NaI) m/z 304.2608 (C$_{18}$H$_{35}$NO+Na$^+$ requires 304.2616).

18:1[15] as Illustrated in FIG. 2

Synthesized exactly as found in the general procedure vida supra; all starting reagents were purchased from Aldrich, Acros, or Sigma and resulting white solid was purified by chromatography: white solid: mp 92–93° C.; $^1$H NMR (CDCl$_3$, 500 MHz) δ5.70 (br, 1H), 5.46 (br, 1H), 5.35–5.27 (m, 2H), 2.19 (t, 2H, J=7.5 Hz), 1.99 (h, 4H, J=6.8 Hz), 1.60 (p, 2H, J=7.3 Hz), 1.31–1.22 (m, 20H), 0.92 (t, 3H, J=7.5 Hz); $^{13}$C NMR (CDCl$_3$, 125 MHz) δ175.7, 131.5, 129.3, 35.9, 29.7, 29.60, 29.56, 29.5, 29.4, 29.31, 29.26, 29.2, 27.1, 25.5, 20.5, 14.4; IR (film) $\upsilon_{max}$ 3356, 3189, 2918, 2848, 1659, 1632, 1470, 1420, 1410, 1137 cm$^{-1}$; FAB-HRMS (NBA-CsI) m/z 282.2707 (C$_{18}$H$_{35}$NO+H$^+$ requires 282.2797).

19:1[10] as Illustrated in FIG. 2

Synthesized exactly as found in the general procedure vida supra; all starting reagents were purchased from Aldrich, Acros, or Sigma and resulting white solid was purified by chromatography: white solid: mp 71–72° C.; $^1$H NMR (CDCl$_3$, 400 MHz) δ5.95 (br, 1H), 5.53 (br, 1H), 5.35–5.26 (m, 2H), 2.17 (t, 2H, J=7.6 Hz), 1.97 (m, 4H), 1.59 (p, 2H, J=7.2 Hz), 1.25–1.23 (m, 22H), 0.84 (t, 3H, J=6.9 Hz); $^{13}$C NMR (CDCl$_3$, 100 MHz) δ176.0, 129.9, 129.7, 35.9, 31.9, 29.7, 29.5, 29.34, 29.27, 29.2, 27.2, 25.5, 22.6, 14.1; IR (film) $\upsilon_{max}$ 3362, 3194, 2920, 2850, 1651, 1633, 1469, 1422 cm$^{-1}$; FABHRMS (NBA-CsI) m/z 296.2961 (C$_{19}$H$_{37}$NO+H$^+$ requires 296.2953). 10Z-nonadecenoic acid prepared as previously described (JACS, 1996, 118, 5938–5945).

20:1[5] as Illustrated in FIG. 2

Synthesized exactly as found in the general procedure vida supra; all starting reagents were purchased from Aldrich, Acros, or Sigma and resulting white solid was purified by chromatography: (50%–100% EtOAc/hexanes, gradient elution) to afford 86% desired product; mp 82° C.; $^1$H NMR (CD$_3$OD, 400 MHz) δ5.35–5.23 (m, 2H), 2.11 (t, 2H, J=7.6 Hz), 2.02–1.93 (m, 4H), 1.56 (p, 2H, J=7.5 Hz), 1.28–1.15 (m, 24H), 0.81 (t, 3H, J=6.9 Hz); $^{13}$C NMR (CDCl$_3$, 100 MHz) δ175.5, 131.2, 128.4, 35.2, 31.9, 29.7, 29.7, 29.67, 29.63, 29.3, 27.3, 26.5, 25.4, 22.7, 14.1; IR (NaCl, film) $\upsilon_{max}$ 3371, 2917, 2849, 2535, 2361, 1632, 1511, 1471, 1423 cm$^{-1}$; HRFABMS m/z (M+H$^+$) 310.3100 (requires m/z 310.3110).

20:1[8] as Illustrated in FIG. 2

Synthesized exactly as found in the general procedure vida supra; all starting reagents were purchased from Aldrich, Acros, or Sigma and resulting white solid was purified by chromatography: white solid: mp 71–72° C.; $^1$H NMR (CDCl$_3$, 500 MHz) δ5.70 (br, 1H), 5.44 (br, 1H), 5.36–5.27 (m, 2H), 2.19 (t, 2H, J=7.5 Hz), 1.99–1.96 (m, 4H), 1.61 (p, 2H, J=7.0 Hz), 1.30–1.23 (m, 24H), 0.85 (t, 3H, J=7.0 Hz); $^{13}$C NMR (CDCl$_3$, 125 MHz) δ175.7, 130.1, 129.6, 35.9, 31.9, 29.73, 29.66, 29.62, 29.54, 29.33, 29.31, 29.1, 29.0, 27.2, 27.1, 25.5, 22.7, 14.1; IR (film) $\upsilon_{max}$ 3389, 3200, 3003, 2917, 2848, 1645, 1467, 1418, 722 cm$^{-1}$; FABHRMS (NBA-NaI) m/z 310.3125 (C$_{20}$H$_{39}$NO+H$^+$ requires 310.3110).

20:1[9] as Illustrated in FIG. 2

Synthesized exactly as found in the general procedure vida supra; all starting reagents were purchased from Aldrich, Acros, or Sigma and resulting white solid was purified by chromatography: The crude product was chromatographed (SiO$_2$, 1×10 cm, 50–100% EtOAc/hexanes, gradient elution) to afford 9 (21.4 mg, 61%) as a white solid: mp 72–73° C.; $^1$H NMR (CDCl$_3$, 400 MHz) δ5.56 (br, 1H), 5.41 (br, 1H), 5.36–5.27 (m, 2H), 2.19 (t, 2H, J=7.6 Hz), 1.99–1.96 (m, 4H), 1.61 (p, 2H, J=7.1 Hz), 1.28–1.23 (m, 28H), 0.85 (t, 3H, J=6.8 Hz); $^{13}$C NMR (CDCl$_3$, 100 MHz) δ175.6, 130.0, 129.7, 35.9, 31.9, 29.75, 29.67, 29.64, 29.55, 29.34, 29.31, 29.22, 29.19, 29.10, 27.2, 27.1, 25.5, 22.7, 14.1; IR (film) $v_{max}$ 3390, 3199, 2917, 2848, 1643, 1467, 722 cm$^{-1}$; FABHRMS (NBA-NaI) m/z 338.3416 (C$_{22}$H$_{43}$NO+H$^+$ requires 338.3423). Acid prepared in a manner analogous to 22:1$^9$.

20:1$^{11}$ as Illustrated in FIG. 2

Synthesized exactly as found in the general procedure vida supra; all starting reagents were purchased from Aldrich, Acros, or Sigma and resulting white solid was purified by chromatography: White solid was purified by chromatography (50%–66% EtOAc/hexanes, gradient elution) to afford 97% desired product; mp 81–82° C.; $^1$H NMR (CD$_3$OD, 400 MHz) 67 5.29δ5.21 (m, 2H), 2.10 (t, 2H, J=7.6 Hz), 1.93 (m, 4H), 1.51 (p, 2H, J=7.3 Hz), 1.22 (m, 24H), 0.83 (t, 3H, J=6.9 Hz); $^{13}$C NMR (CD$_3$OD, 100 MHz) 67 179.3, 130.8 (2), 36.6, 33.1, 30.88, 30.86, 30.6, 30.5, 30.4, 28.2, 28.1, 26.9, 23.8, 14.5; IR (NaCl, film) $v_{max}$ 3324, 2918, 2849, 2522, 2353, 1629, 1527, 1468, 1437, 1410, 955, 721 cm$^{-1}$; HRFABMS m/z (M+Cs$^+$) 442.2068 (requires m/z 442.2086).

20:1$^{13}$ as Illustrated in FIG. 2

Synthesized exactly as found in the general procedure vida supra; all starting reagents were purchased from Aldrich, Acros, or Sigma and resulting white solid was purified by chromatography: White solid was purified by chromatography (33% EtOAc/hexanes) to afford 89% desired product; mp 84–85° C.; $^1$H NMR (CD$_3$OD, 400 MHz) δ5.29–5.21 (m, 2H), 2.10 (t, 2H, J=7.6 Hz), 1.93 (m, 4H), 1.51 (p, 2H, J=7.2 Hz), 1.21 (m, 24H), 0.81 (t, 3H, J=6.9 Hz); $^{13}$C NMR (CD$_3$OD, 100 MHz) δ179.3, 130.9 (2), 36.6, 33.0, 30.9 (2), 30.8 (2), 30.7 (2), 30.5, 30.3 (2), 30.1, 28.2, 28.1, 26.9, 23.8, 14.5; IR (NaCl, film) $v_{max}$ 3324, 2917, 2849, 2523, 2347, 1630, 1526, 1470, 1430, 1410, 953, 721 cm$^{-1}$; HRFABMS m/z (M+H$^+$) 310.3099 (requires m/z 310.3110).

Figure 18:
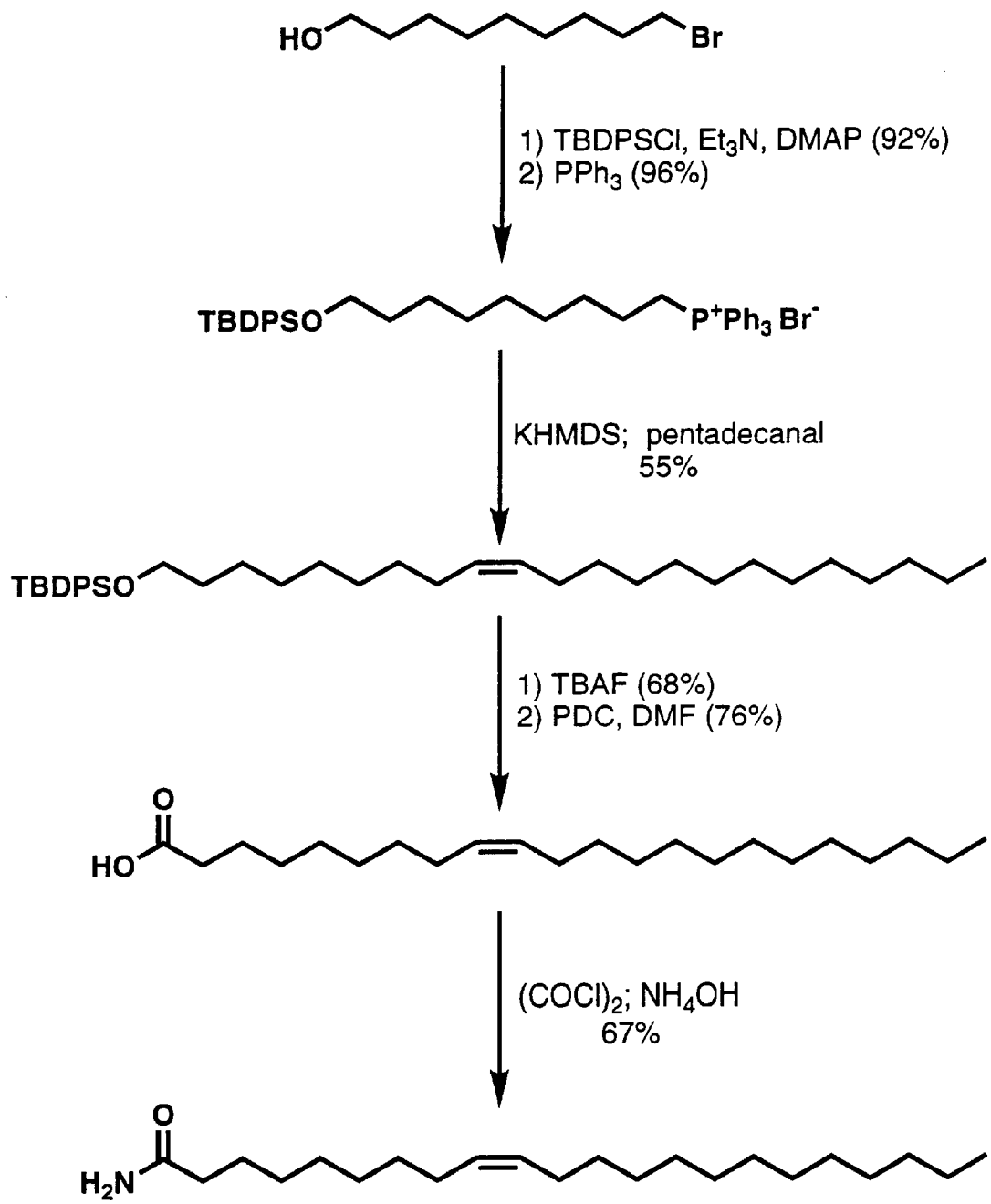
FIG. 18 illustrates a general synthesis for oleamide and analogs.

22:1$^9$ as Illustrated in FIG. 2 and Route Illustrated in FIG. 18

7-bromoheptanol was protected (TBDPSCl, Et$_3$N, DMAP) and treated with PPh$_3$ to generate a phosphonium salt (284.9 mg, 0.42 mmol, 1 eq) that was dissolved in anhydrous THF (2.6 mL) under Ar at −78° C. was treated dropwise with KHMDS (0.5M in toluene, 0.85 mL, 0.43 mmol, 1 eq). The orange solution was allowed to stir for 40 min at −78° C. before tridecanal (100 µL, 0.42 mmol, 1 eq) was added. The reaction was warmed to 25° C. and allowed to stir 1 h before saturated aqueous NH$_4$Cl (30 mL) was added. The aqueous layer was extracted with EtOAc (3×30 mL). The organic layers were dried (Na$_2$SO$_4$), filtered, and concentrated in vacuo. The crude product was chromatographed (SiO$_2$, 2×8 cm, 0–5% EtOAc/hexanes, gradient elution) to afford alkene (131.0 mg, 55%) as a clear oil; $^1$H NMR (CDCl$_3$, 500 MHz) δ7.69 (dd, 4H, J=8.0, 1.5 Hz), 7.44–7.37 (m, 6H), 5.40–5.34 (m, 2H), 3.67 (t, 2H, J=6.5 Hz), 2.03 (q, 4H, J=6.0 Hz), 1.58 (p, 2H, J=7.5 Hz), 1.35–1.28 (m, 30H), 1.07 (s, 9H), 0.90 (t, 3H, J=7.0 Hz); $^{13}$C NMR (CDCl$_3$, 125 MHz) δ135.6, 134.2, 129.90, 129.86, 129.5, 127.5, 64.0, 32.6, 31.9, 29.8, 29.70, 29.67, 29.6, 29.5, 29.4, 29.33, 29.26, 27.2, 26.9, 25.8, 22.7, 19.2, 14.1; IR (film) $v_{max}$ 2925, 2854, 1472, 1457, 1112, 823, 701, 608 cm$^{-1}$; FABHRMS (NBA-CsI) m/z 695.3649 (C$_{38}$H$_{62}$OSi+ Cs$^+$ requires 695.3624).

A solution of alkene (128.2 mg, 0.23 mmol, 1 eq) in THF (2.2 mL) under N$_2$ was treated with TBAF (1M in THF, 0.46 mL, 0.46 mmol, 2 eq) and stirred at 25° C. for 2.5 h. Water (30 mL) was added and the aqueous layers were extracted with EtOAc (3×30 mL). The organic layers were dried (Na$_2$SO$_4$), filtered, and concentrated in vacuo. The crude product was chromatographed (SiO$_2$, 2×5 cm, 5–33% EtOAc/hexanes, gradient elution) to afford alcohol (51.2 mg, 69%) as a white film; $^1$H NMR (CDCl$_3$, 400 MHz) δ5.36–5.29 (m, 2H), 3.62 (t, 2H, J=6.6 Hz), 2.02–1.97 (m, 4H), 1.54 (p, 2H, J=6.8 Hz), 1.28–1.24 (m, 30H), 0.86 (t, 3H, J=6.8 Hz); $^{13}$C NMR (CDCl$_3$, 100 MHz) δ129.9, 129.8, 63.1, 32.8, 31.9, 29.73, 29.67, 29.64, 29.6, 29.5, 29.39, 29.35, 29.31, 29.2, 27.2, 25.7, 22.7, 14.1; IR (film) $v_{max}$ 3328, 2923, 2852, 1457, 1055 cm$^{-1}$; FABHRMS (NBA-NaI) m/z 325.3475 (C$_{22}$H$_{44}$O+H$^+$ requires 325.3470).

A solution of alcohol (48.5 mg, 0.15 mmol, 1 eq) in anhydrous DMF (1 mL) under N$_2$ was treated with PDC (0.28 g, 0.74 mmol, 5 eq) and stirred at 25° C. for 3.5 h. The reaction mixture was filtered through celite and the filtrate was concentrated in vacuo. The crude product was chromatographed (SiO$_2$, 1×8 cm, 10–20% EtOAc/hexanes, gradient elution) to afford acid (36.2 mg, 72%) as a clear oil; $^1$H NMR (CDCl$_3$, 400 MHz) δ5.37–5.28 (m, 2H), 2.33 (t, 2H, J=7.5 Hz), 2.01–1.97 (m, 4H), 1.61 (p, 2H, J=7.2 Hz), 1.29–1.24 (m, 28H), 0.86 (t, 3H, J=6.8 Hz); $^{13}$C NMR (CDCl$_3$, 100 MHz) δ179.9, 130.0, 129.7, 34.0, 31.9, 29.8, 29.7, 29.6, 29.4, 29.3, 29.14, 29.06, 29.03, 27.2, 27.1, 24.7, 22.7, 14.1; IR (film) $v_{max}$ 2918, 2850, 1689, 1466, 1411, 1297, 918, 722, 687 cm$^{-1}$; FABHRMS (NBA-NaI) m/z 361.3091 (C$_{22}$H$_{42}$O$_2$+Na$^+$ requires 361.3083).

A solution of acid (34.9 mg, 0.103 mmol, 1 eq) in anhydrous CH$_2$Cl$_2$ (0.5 mL) under N$_2$ at 0° C. was treated with oxalyl chloride (2M in CH$_2$Cl$_2$, 0.13 mL, 0.26 mmol, 3 eq). The reaction mixture was warmed to 25° C. and stirred for 3 h before the solvent was removed in vacuo. The residue was cooled to 0° C. and treated with excess concentrated NH$_4$OH (1 mL). Water (30 mL) was added and the aqueous layer was extracted with EtOAc (3×30 mL). The organic layers were dried (Na$_2$SO$_4$), filtered, and concentrated in vacuo. The crude product was chromatographed (SiO$_2$, 1×10 cm, 50–100% EtOAc/hexanes, gradient elution) to afford 22:1$^9$ (21.4 mg, 61%) as a white solid: mp 72–73° C.; $^1$H NMR (CDCl$_3$, 400 MHz) δ5.56 (br, 1H), 5.41 (br, 1H), 5.36–5.27 (m, 2H), 2.19 (t, 2H, J=7.6 Hz), 1.99–1.96 (m, 4H), 1.61 (p, 2H, J=7.1 Hz), 1.28–1.23 (m, 28H), 0.85 (t, 3H, J=6.8 Hz); $^{13}$C NMR (CDCl$_3$, 100 MHz) δ175.6, 130.0, 129.7, 35.9, 31.9, 29.75, 29.67, 29.64, 29.55, 29.34, 29.31, 29.22, 29.19, 29.10, 27.2, 27.1, 25.5, 22.7, 14.1; IR (film) $v_{max}$ 3390, 3199, 2917, 2848, 1643, 1467, 722 cm$^{-1}$; FABHRMS (NBA-NaI) m/z 338.3416 (C$_{22}$H$_{43}$NO+H$^+$ requires 338.3423).

22:1$^{13}$ (Erucamide) as Illustrated in FIG. 2

Synthesized exactly as found in the general procedure vida supra; all starting reagents were purchased from Aldrich, Acros, or Sigma and resulting white solid was purified by chromatography: White solid was purified by chromatography (50% EtOAc/hexanes) to afford 96% desired product; mp 83–84° C.; $^1$H NMR (CDCl$_3$, 400 MHz) δ5.29–5.21 (m, 2H), 2.09 (t, 2H, J=7.6 Hz), 1.93 (m, 4H), 1.51 (p, 2H, J=7.3 Hz), 1.20 (m, 28H), 0.81 (t, 3H, J=6.9 Hz); $^{13}$C NMR (CDCl$_3$, 100 MHz) δ175.8, 129.88, 129.85, 36.0, 31.9, 29.7, 29.58, 29.53, 29.50, 29.46, 29.32, 29.29, 29.18, 27.2, 25.3, 22.7, 14.1; IR (NaCl, film) $v_{max}$ 3375, 2920, 2847, 2544, 1633, 1511, 1468, 1417, 932, 721 cm$^{-1}$; HRFABMS m/z (M+Cs$^+$) 470.2413 (requires m/z 470.2399).

24:1[9] as Illustrated in FIG. 2

Synthesized exactly as found in the general procedure vida supra; all starting reagents were purchased from Aldrich, Acros, or Sigma and resulting white solid was purified by chromatography: ($SiO_2$, 1×10 cm, 50–100% EtOAc/hexanes, gradient elution) to afford 13 (20.7 mg, 67%) as a white solid: mp 74–75° C.; $^1$H NMR ($CDCl_3$, 500 MHz) δ5.49 (br, 1H), 5.39 (br, 1H), 5.35–5.28 (m, 2H), 2.19 (t, 2H, J=7.8 Hz), 2.00–1.96 (m, 4H), 1.61 (p, 2H, J=7.0 Hz), 1.29–1.23 (m, 32H), 0.85 (t, 3H, J=7.0 Hz); $^{13}$C NMR ($CDCl_3$, 125 MHz) δ175.5, 130.0, 129.7, 35.9, 31.9, 29.8, 29.68, 29.65, 29.56, 29.3, 29.23, 29.19, 29.1, 27.21, 27.15, 25.5, 22.7, 14.1; IR (film) $υ_{max}$ 3389, 3184, 2917, 2848, 1044, 1467, 1416, 1119 cm$^{-1}$; FABHRMS (NBA-NaI) m/z 366.3740 ($C_{24}H_{47}NO+H^+$ requires 366.3736). Acid prepared in a manner analogous to 22:1[9].

24:1[15] (Nervonamide) as Illustrated in FIG. 2

Synthesized exactly as found in the general procedure vida supra; all starting reagents were purchased from Aldrich, Acros, or Sigma and resulting white solid was purified by chromatography: White solid was purified by chromatography (33%–66% EtOAc/hexanes, gradient elution) to afford 91% desired product; mp 87–88° C.; $^1$H NMR ($CDCl_3$, 400 MHz) δ5.36–5.28 (m, 2H), 2.19 (t, 2H, J=7.6 Hz), 1.98 (m, 4H), 1.60 (p, 2H, J=7.2 Hz), 1.36–1.23 (m, 32H), 0.85 (t, 3H, J=6.8 Hz); $^{13}$C NMR ($CDCl_3$, 100 MHz) δ175.7, 129.9 (2), 35.94, 35.91, 31.9, 29.8, 29.63, 29.56, 29.54, 29.50, 29.46, 29.33, 29.30, 29.22, 27.18, 25.5, 22.7, 14.1; IR (NaCl, film) $υ_{max}$ 3392, 2919, 2847, 2543, 2358, 1633, 1468, 1412, 720 cm$^{-1}$; HRFABMS m/z (M+H$^+$) 366.3727 (requires 366.3736).

18:2[9,12] (Linoleamide) as Illustrated in FIG. 2

Prepared as previously described. (JACS, 1996, 118, 580–590).

18:2[9,12-trans] (Linoelaidamide) as Illustrated in FIG. 2

Synthesized exactly as found in the general procedure vida supra; all starting reagents were purchased from Aldrich, Acros, or Sigma and resulting white solid was purified by chromatography: (50%i EtOAc/hexanes) to afford 88% desired product; mp 83–84° C.; $^1$H NMR ($CD_3OD$, 400 MHz) δ5.35–5.24 (m, 4H), 2.59 (m, 2H), 2.10 (t, 2H, J=7.6 Hz), 1.90 (m, 4H), 1.51 (p, 2H, J=7.2 Hz), 1.33–1.13 (m, 14H), 0.81 (t, 3H, J=7.0 Hz); $^{13}$C NMR ($CD_3OD$, 100 MHz) δ179.3, 131.99, 131.92, 130.0, 129.9, 36.6, 36.5, 33.6 (2), 32.5, 30.7, 30.4, 30.3 (2), 30.1, 26.9, 23.6, 14.5; IR (NaCl, film) $υ_{max}$ 3371, 2917, 2847, 2540, 2345, 1622, 1470, 1420, 964, 716 cm$^{-1}$; HRFABMS m/z (M+Cs$^+$) 412.1598 (requires m/z 412.1616).

20:2[11,14] as Illustrated in FIG. 2

Synthesized exactly as found in the general procedure vida supra; all starting reagents were purchased from Aldrich, Acros, or Sigma and resulting white solid was purified by chromatography: (50%–100% EtOAc/hexanes, gradient elution) to afford 92% desired product; mp 47–49° C.; $^1$H NMR ($CD_3OD$, 400 MHz) δ5.31–5.20 (m, 4H), 2.67 (t, 2H, J=6.2 Hz), 2.12 (t, 2H, J=7.6 Hz), 1.97 (q, 4H, J=6.8 Hz), 1.52 (p, 2H, J=7.3 Hz), 1.32–1.17 (m, 18H), 0.82 (t, 3H, J=6.9); $^{13}$C NMR ($CD_3OD$, 100 MHz) δ179.2, 130.9 (2), 129.1 (2), 36.5, 32.7, 30.8 (2), 30.7 (2), 30.5 (2), 30.41, 30.36, 28.2, 26.9, 26.6, 23.7, 14.5; IR (NaCl, film) $υ_{max}$ 3324, 3009, 2919, 2849, 2513, 2466, 2400, 1733, 1634, 1528, 1469, 1410, 1250, 1048, 758 cm$^{-1}$; LRFABMS m/z (M+H$^+$) 308.

18:3[9,12,15]: (α-Linolenamide) as Illustrated in FIG. 2

Synthesized exactly as found in the general procedure vida supra; all starting reagents were purchased from Aldrich, Acros, or Sigma and resulting yellow gel was purified by chromatography: (33%–100% EtOAc/hexanes, gradient elution) to afford 99% desired product. $^1$H NMR ($CD_3OD$, 400 MHz) δ5.33–5.18 (m, 6H), 2.76 (t, 4H, J=6.0 Hz), 2.11 (t, 2H, J=7.6 Hz), 2.00 (m, 4H), 1.52 (p, 2H, J=7.1 Hz), 1.26 (m, BH), 0.89 (t, 3H, J=7.5 Hz); $^{13}$C NMR ($CD_3OD$, 100 MHz) δ179.2, 132.7, 131.1, 129.2 (2), 128.8, 128.2, 36.5, 30.7, 30.4, 30.31, 30.26, 28.2, 26.9, 26.5, 26.4, 21.5, 14.7; IR (NaCl, film) $υ_{max}$ 3326, 3009, 2924, 2851, 2526, 2356, 1629, 1527, 1469, 1436, 1410, 955, 723 cm$^{-1}$; HRFABMS m/z (M+Cs$^+$) 410.1452 (requires m/z 410.1460).

20:3[8,11,14] as Illustrated in FIG. 2

Synthesized exactly as found in the general procedure vida supra; all starting reagents were purchased from Aldrich, Acros, or Sigma and resulting yellow gel was purified by chromatography: (50%–100% EtOAc/hexanes, gradient elution) to afford 78% desired product. $^1$H NMR ($CD_3OD$, 400 MHz) δ5.32–5.21 (m, 6H), 2.73 (m, 4H), 2.11 (t, 2H, J=7.6 Hz), 1.98 (m, 4H), 1.51 (p, 2H, J=7.2 Hz), 1.34–1.20 (m, 12H), 0.81 (t, 3H, J=6.9 Hz); $^{13}$C NMR ($CD_3OD$, 100 MHz) δ179.3, 131.1, 131.0, 129.22, 129.16, 128.9, 128.8, 36.5, 32.7 30.7, 30.5, 30.3, 30.1, 28.2 (2), 26.9, 26.6 (2), 23.7, 14.5; IR (NaCl, film) $υ_{max}$ 3328, 3009, 2925, 2852, 2525, 2468, 2402, 1634, 1527, 1466, 1411, 1330, 1202, 959 cm$^{-1}$; HRFABMS m/z (M+Cs$^+$) 438.1756 (requires m/z 438.1773).

20:3[11,14,17] as Illustrated in FIG. 2

Synthesized exactly as found in the general procedure vida supra; all starting reagents were purchased from Aldrich, Acros, or Sigma and resulting yellow gel was purified by chromatography: (50%–100% EtOAc/hexanes, gradient elution) to afford 84% desired product. $^1$H NMR ($CD_3OD$, 400 MHz) δ5.32–5.17 (m, 6H), 2.71 (t, 4H, J=5.9 Hz), 2.10 (t, 2H, J=7.6 Hz), 2.01–1.92 (m, 4H), 1.51 (p, 2H, J=7.3 Hz), 1.29–1.23 (m, 12H), 0.88 (t, 3H, J=7.6 Hz); $^{13}$C NMR ($CD_3OD$, 100 MHz) δ179.3, 132.7, 131.1, 129.21, 129.17, 128.8, 128.2, 36.5, 30.8, 30.64, 30.62, 30.5, 30.4, 30.3, 28.2, 26.9, 26.5, 26.4, 21.5, 14.7; IR (NaCl, film) $υ_{max}$ 3324, 3010, 2963, 2919, 2849, 2525, 2351, 1627, 1529, 1469, 1439, 1410, 956, 721 cm$^{-1}$; HRFABMS m/z (M+Cs$^+$) 438.1765 (requires m/z 438.1773).

20:4[5,8,11,14] as Illustrated in FIG. 2

Purchased from Sigma.

20:5[5,8,11,14,17] as Illustrated in FIG. 2

Synthesized exactly as found in the general procedure vida supra; all starting reagents were purchased from Aldrich, Acros, or Sigma and clear oil gel was purified by chromatography: $^1$H NMR ($CDCl_3$, 500 MHz) δ5.38–5.35 (m, 10H), 2.83–2.78 (m, 8H), 2.21 (t, 2H, J=7.5 Hz), 2.11 (q, 2H, J=6.5 Hz), 2.06 (p, 2H, J=7.5 Hz), 1.71 (p, 2H, J=7.5 Hz), 0.95 (t, 3H, J=7.5 Hz); $^{13}$C NMR ($CDCl_3$, 125 MHz) δ175.1, 132.1, 129.0, 128.9, 128.6, 128.3, 128.19, 128.16, 128.07, 127.8, 35.1, 26.5, 25.6, 25.5, 25.2, 20.6, 14.3; IR (film) $υ_{max}$ 3354, 3192, 3011, 2961, 1660, 1614, 1441, 1410, 1264 cm$^{-1}$; FABHRMS (NBA-NaI) m/z 302.2489 ($C_{20}H_{31}NO+H^+$ requires 302.2484).

22:6[4,7,10,13,16,19] as Illustrated in FIG. 2

Synthesized exactly as found in the general procedure vida supra; all starting reagents were purchased from Aldrich, Acros, or Sigma and clear oil gel was purified by chromatography: (50%–100% EtOAc/hexanes, gradient elution) to afford 55% desired product. $^1$H NMR ($CD_3OD$, 400 MHz) δ5.33–5.17 (m, 12H), 2.80–2.71 (m, 10H), 2.31 (m, 2H), 2.14 (t, 2H, J=7.4 Hz), 1.98 (p, 2H, J=7.4 Hz), 0.87 (t, 3H, J=7.6 Hz); $^{13}$C NMR ($CD_3OD$, 100 MHz) δ178.4, 132.8, 130.1, 129.4, 129.23, 129.19, 129.16, 129.09, 128.9, 128.2, 36.3, 26.54, 26.49, 26.42, 24.5, 21.5, 14.7; IR (NaCl, film) $\upsilon_{max}$ 3341, 3198, 3012, 2955, 1661, 1393, 1262, 923 cm$^{-1}$; HRFABMS m/z (M+Cs$^+$) 460.1640 (requires m/z 460.1616).

General Procedure For the Preparation of Oleic Amide Derivatives Varying About Carboxamide (Unless Otherwise Described) as Illustrated in FIG. 3

One equivalent of oleic acid was dissolved in dry CH$_2$Cl$_2$ (0.2 M) and cooled to 0° C. under a N$_2$ atmosphere. Oxalyl chloride (2M in CH$_2$Cl$_2$, 3 equiv) was added slowly. The solution was warmed to 25° C. and allowed to stir for 3 hours in the dark. The solvent was then removed in vacuo and the flask cooled to 0° C. Excess free amine (amines that were available as the hydrochloride salts were extracted into EtOAc from a 50% NaOH solution before use) or alcohols were added slowly. The crude product was purified by chromatography on SiO$_2$ using EtOAc/hexanes as an eluent.

Oleic Acid

Agent purchased from Aldrich.

MeNH as Illustrated in FIG. 3

Synthesized exactly as found in the general procedure for derivatives varying about carboxamide vida supra; all starting reagents were purchased from Aldrich, Acros, or Sigma: White solid was purified by chromatography (50% EtOAc/hexanes) to afford 95% desired product; mp 34–35° C.; $^1$H NMR (CD$_3$OD, 400 MHz) δ5.29–5.21 (m, 2H), 2.61 (s, 3H), 2.07 (t, 2H, J=7.6 Hz), 1.93 (m, 4H), 1.50 (p, 2H, J=7.0 Hz), 1.23–1.21 (m, 20H), 0.81 (t, 3H, J=6.9 Hz); $^{13}$C NMR (CD$_3$OD, 100 MHz) δ176.7, 130.9, 130.8, 37.0, 33.1, 30.87, 30.85, 30.7, 30.5, 30.4, 30.34, 30.27, 28.2, 27.0, 26.3, 23.8, 14.5; IR (NaCl, film) $\upsilon_{max}$ 3301, 3005, 2921, 2853, 2418, 1651, 1557, 1463, 1403, 1164, 723 cm$^{-1}$; HRFABMS m/z (M+H$^+$) 296.2940 (requires m/z 296.2953).

Me$_2$N as Illustrated in FIG. 3

Synthesized exactly as found in the general procedure for derivatives varying about carboxamide vida supra; all starting reagents were purchased from Aldrich, Acros, or Sigma: Pale yellow oil was purified by chromatography (33% EtOAc/hexanes) to afford 99% desired product. $^1$H NMR (CD$_3$OD, 400 MHz) δ5.32–5.24 (m ,2H), 2.99 (s, 3H), 2.86 (s, 3H), 2.29 (t, 2H, J=7.6 Hz), 1.97 (m, 4H), 1.53 (p, 2H, J=7.3 Hz), 1.28–1.24 (m, 20H), 0.85 (t, 3H, J=6.8 Hz); $^{13}$C NMR (CD$_3$OD, 100 MHz) δ175.4, 130.82 130.77, 37.8, 35.7, 34.2, 33.1, 30.90, 30.87, 30.7, 30.5, 30.4, 30.3, 28.2, 26.3, 23.8, 14.6; IR (NaCl, film) $\upsilon_{max}$ 2923, 2853, 1652, 1463, 1394, 1267, 1141, 723 cm$^{-1}$; HRFABMS m/z (M+H$^+$) 310.3101 (requires m/z 310.3110).

EtNH Derivative as Illustrated in FIG. 3

Synthesized exactly as found in the general procedure for derivatives varying about carboxamide vida supra; all starting reagents were purchased from Aldrich, Acros, or Sigma: White solid was purified by chromatography (33% EtOAc/hexanes) to afford 99% desired product; mp 34–35° C.; $^1$H NMR (CDCl$_3$, 400 MHz) δ5.53 (br, 1H), 5.35–5.26 (m, 2H), 3.28–3.21 (m, 2H), 2.11 (t, 2H, J=7.7 Hz), 2.01–1.92 (m, 4H), 1.58 (p, 2H, J=7.4 Hz), 1.30–1.23 (m, 20H), 1.09 (t, 3H, J=7.3 Hz), 0.83 (t, 3H, J=6.9 Hz); $^{13}$C NMR (CDCl$_3$, 100 MHz) δ173.0, 130.0, 129.7, 36.8, 34.2, 31.9, 29.73, 29.67, 29.5, 29.29 (2), 29.25 (2), 29.1, 27.2, 27.1, 25.8, 22.7, 14.9, 14.1; IR (NaCl, film) $\upsilon_{max}$ 3304, 3084, 2918, 2850, 1641, 1551, 1466, 938, 721 cm$^{-1}$; HRFABMS m/z (M+H$^+$) 310.3099 (requires m/z 310.3110).

Et$_2$N Derivative as Illustrated in FIG. 3

Synthesized exactly as found in the general procedure for derivatives varying about carboxamide vida supra; all starting reagents were purchased from Aldrich, Acros, or Sigma: Pale orange oil was purified by chromatography (20%–50% EtOAc/hexanes, gradient elution) to afford 99% desired product. $^1$H NMR (CD$_3$OD, 400 MHz) δ5.32–5.25 (m, 2H), 3.31 (p, 4H, J=7.2 Hz), 2.28 (t, 2H, J=7.6 Hz), 1.97 (m, 4H), 1.55 (p, 2H, J=7.3 Hz), 1.29–1.24 (m, 20H), 1.13 (t, 3H, J=7.1 Hz), 1.04 (t, 3H, J=7.1 Hz), 0.85 (t, 3H, J=6.9 Hz); $^{13}$C NMR (CD$_3$OD, 100 MHz) δ174.4, 130.81, 130.77, 43.4, 41.4, 33.9, 33.1, 30.91, 30.87, 30.7, 30.5, 30.4, 30.3, 28.3, 26.7, 23.8, 14.7, 14.6, 13.4; IR (NaCl, film) $\upsilon_{max}$ 2925, 2853, 1651, 1462, 1427, 1379, 1309, 1261, 1223, 1139, 1096, 944, 791, 722 cm$^{-1}$; HRFABMS m/z (M+H$^+$) 338.3430 (requires m/z 338.3423).

PrNH Derivative as Illustrated in FIG. 3

Synthesized exactly as found in the general procedure for derivatives varying about carboxamide vida supra; all starting reagents were purchased from Aldrich, Acros, or Sigma: white solid: mp 28–29° C.; $^1$H NMR (CDCl$_3$, 400 MHz) δ6.01 (br, 1H), 5.29–5.21 (m, 2H), 3.12 (q, 2H, J=6.8 Hz), 2.08 (t, 2H, J=7.6 Hz), 1.95–1.90 (m, 4H), 1.54 (p, 2H, J=7.4 Hz), 1.43 (s, 2H, J=7.2 Hz), 1.21–1.19 (m, 20H), 0.89–0.78 (m, 6H); $^{13}$C NMR (CDCl$_3$, 100 MHz) δ173.1, 129.8, 129.6, 41.0, 36.6, 31.7, 29.60, 29.56, 29.4, 29.2 (4), 29.0, 27.04, 27.01, 25.7, 22.7, 22.5, 13.9, 11.2; IR (film) $\upsilon_{max}$ 3298, 2924, 2854, 1648, 1552, 1464, 1378, 1253, 1153, 757 cm$^{-1}$; ESI (M+H$^+$) 324.

i-PrNH Derivative as Illustrated in FIG. 3

Synthesized exactly as found in the general procedure for derivatives varying about carboxamide vida supra; all starting reagents were purchased from Aldrich, Acros, or Sigma: white solid: mp 25° C.; $^1$H NMR (CDCl$_3$, 400 MHz) δ5.46–5.45 (br, 1H), 5.33–5.24 (m, 2H), 4.07–3.96 (m, 1H), 2.07 (t, 2H, J=7.6 Hz), 1.97–1.93 (m, 4H), 1.56 (p, 2H, J=7.1 Hz), 1.24–1.15 (m, 20H), 1.08 (d, 6H, J=6.6 Hz), 0.83 (t, 3H, J=6.8 Hz); $^{13}$C NMR (CDCl$_3$, 100 MHz) δ172.2, 129.9, 129.7, 41.0, 36.9, 31.8, 29.7, 29.6, 29.4, 29.23, 29.19, 29.1, 27.11, 27.08, 25.7, 22.7, 22.6, 14.0; IR (film) $\upsilon_{max}$ 3291, 2925, 2854, 1645, 1558, 1540, 1457, 1174, 1130, 722 cm$^{-1}$; FABHRMS (NBA-NaI) m/z 324.3259 (C$_{21}$H$_{41}$NO+H$^+$ requires 324.3266).

CH$_2$=CHCH$_2$NH Derivative as Illustrated in FIG. 3

Prepared as described in the literature (Synth. Comm. 1996, 26, 2341–2348).

i-PrNMe Derivative as Illustrated in FIG. 3

Synthesized exactly as found in the general procedure for derivatives varying about carboxamide vida supra using i-Propyl-N-methyl-amine; all starting reagents were purchased from Aldrich, Acros, or Sigma.

Cyclopropylamine Derivative as Illustrated in FIG. 3

Synthesized exactly as found in the general procedure for derivatives varying about carboxamide vida supra using the cyclopropyl amine; all starting reagents were purchased from Aldrich, Acros, or Sigma.

Ph(CH$_2$)$_3$NH Derivative as Illustrated in FIG. 3

Synthesized exactly as found in the general procedure for derivatives varying about carboxamide vida supra using the commercially available Ph(CH$_2$)$_3$NH amine; all starting reagents were purchased from Aldrich, Acros, or Sigma.

BuNH Derivative as Illustrated in FIG. 3

Synthesized exactly as found in the general procedure for derivatives varying about carboxamide vida supra; all starting reagents were purchased from Aldrich, Acros, or Sigma: white solid: mp 30–31° C.; $^1$H NMR (CDCl$_3$, 400 MHz) 67 6.13 (br, 1H), 5.29–5.20 (m, 2H), 3.14 (q, 2H, J=5.9 Hz), 2.07 (t, 2H, J=7.6 Hz), 1.92–1.89 (m, 4H), 1.53 (p, 2H, J=6.8 Hz), 1.43–1.18 (m, 24H), 0.85–0.77 (m, 6H); $^{13}$C NMR (CDCl$_3$, 100 MHz) 67 173.1, 129.8, 129.5, 39.0, 36.6, 31.7, 31.6, 29.59, 29.55, 29.4, 29.2, 29.0, 27.03, 27.00, 25.7, 22.6, 19.9, 13.9, 13.5; IR (film) $\upsilon_{max}$ 3301, 3084, 3001, 2954, 2918, 2849, 1639, 1559, 1466, 1231, 720 cm$^{-1}$; FABHRMS (NBA-NaI) m/z 338.3428 (C$_{23}$H$_{43}$NO+H$^+$ requires 338.3423).

Pyrrole Derivative as Illustrated in FIG. 3

Synthesized exactly as found in the general procedure for derivatives varying about carboxamide vida supra; all starting reagents were purchased from Aldrich, Acros, or Sigma: Pale yellow oil was purified by chromatography (33% EtOAc/hexanes) to afford desired product in quantitative yield. $^1$H NMR (CD$_3$OD, 400 MHz) δ5.29–5.21 (m, 2H), 3.39 (t, 2H, J=6.7 Hz), 3.31 (t, 2H, J=6.9 Hz), 2.22 (t, 2H, J=7.6 Hz), 1.94 (m, 4H), 1.88 (p, 2H, J=6.7 Hz), 1.78 (p, 2H, J=6.9 Hz), 1.52 (p, 2H, J=7.2 Hz), 1.25–1.20 (m, 20H), 0.81 (t, 3H, J=6.8 Hz); $^{13}$C NMR (CD$_3$OD, 100 MHz) δ173.9, 130.83, 130.79, 47.9, 46.8, 35.5, 33.1, 30.94, 30.90, 30.7, 30.54, 30.46, 30.3, 28.2, 27.0, 26.1, 25.4, 23.8, 14.7; IR (NaCl, film) $v_{max}$ 2924, 2853, 1651, 1428, 1342, 1226, 1194, 723 cm$^{-1}$; HRFABMS m/z (M+Cs$^+$) 468.2225 (requires m/z 468.2242).

PhNH Derivative as Illustrated in FIG. 3

Prepared as described in the literature (Synth. Comm. 1995, 25, 959–968).

NHOH Derivative as Illustrated in FIG. 3

Prepared as previously described (JACS, 1996, 118, 5938–5945).

MeONMe Derivative as Illustrated in FIG. 3

Synthesized exactly as found in the general procedure for derivatives varying about carboxamide vida supra; all starting reagents were purchased from Aldrich, Acros, or Sigma:: Pale yellow oil was purified by chromatography (33% EtOAc/hexanes) to afford desired product in quantitative yield. $^1$H NMR (CD$_3$OD, 400 MHz) δ5.34– 5.26 (m, 2H), 3.66 (s, 3H), 3.12 (s, 3H), 2.39 (t, 3H, J=7.0 Hz), 1.99 (m, 4H), 1.56 (p, 2H, J=6.8 Hz), 1.30–1.26 (m, 20H), 0.86 (t, 3H, J=6.1 Hz); $^{13}$C NMR (CD$_3$OD, 100 MHz) δ176.2, 130.9, 130.8, 61.8, 33.1, 32.7, 30.92, 30.88, 30.77, 30.54, 30.49, 30.45, 30.3, 28.2, 25.8,. 23.8, 14.6; IR (NaCl, film) $v_{max}$ 2923, 2853, 1673, 1463, 1413, 1383, 1177, 1116, 998, 722 cm$^{-1}$; HRFABMS m/z (M+H$^+$) 326.3072 (requires m/z 326.3059).

NH$_2$NH Derivative as Illustrated in FIG. 3

Prepared as previously described (JACS, 1996, 118, 5938–5945).

MeO (Methyl Oleate)Derivative as Illustrated in FIG. 3

Synthesized exactly as found in the general procedure for derivatives varying about carboxamide vida supra; all starting reagents were purchased from Aldrich, Acros, or Sigma: The crude mixture was purified by chromatography (SiO$_2$, 5×15 cm, 1% EtOAc/hexanes) to afford quantitative yield of a clear oil. $^1$H NMR spectra agrees with spectra in Sadtler Handbook of NMR data. Additional data: $^{13}$C NMR (CD$_3$OD, 100 MHz) δ176.0, 130.9, 130.8, 52.0, 34.8, 33.1, 30.9, 30.8, 30.6, 30.5, 30.4, 30.3, 30.20, 30.17, 28.14, 28.11, 26.1, 23.8, 14.5; IR (NaCl, film) $v_{max}$ 2924, 2854, 1743, 1653, 1558, 1540, 1506, 1457, 1260, 1093, 1018, 801 cm$^{-1}$;

EtO (Ethyl Oleate) Derivative as illustrated in FIG. 3

Synthesized exactly as found in the general procedure for derivatives varying about carboxamide vida supra; all starting reagents were purchased from Aldrich, Acros, or Sigma: clear oil. $^1$H NMR spectra agrees with spectra in Sadtler Handbook of NMR data. Additional data: $^{13}$C NMR (CD$_3$OD, 100 MHz) δ173.8, 129.9, 129,7, 60.1, 34.3, 31.9, 29.7, 29.6, 29.5, 29.3, 29.12, 29.08, 29.05, 27.2, 27.1, 24.9, 22.6, 14.2, 14.1; IR (NaCl, film) $v_{max}$ 2925, 2854, 1739, 1465, 1373, 1244, 1180, 1036, 723 cm$^{-1}$.

Me$_2$CHCH$_2$O Derivative as Illustrated in FIG. 3

Synthesized exactly as found in the general procedure for derivatives varying about carboxamide vida supra; all starting reagents were purchased from Aldrich, Acros, or Sigma: pale yellow oil. $^1$H NMR (CDCl$_3$, 400 MHz) δ5.35–5.27 (m, 2H), 3.82 (d, 2H, J=3.4 Hz), 2.27 (t, 2H, J=7.5 Hz), 1.98–1.95 (m, 4H), 1.89 (septet, 1H, J=6.7 Hz), 1.59 (quintet, 2H, J=6.9 Hz), 1.27–1.23 (m, 20H), 0.90 (d, 6H, J=3.4 Hz), 0.85 (t, 3H, J=6.6 Hz); $^{13}$C NMR (CDCl$_3$, 100 MHz) δ173.97, 129.92, 129.72, 70.36, 34.36, 31.89, 29.75, 29.67, 29.51, 29.31 (2), 29.15, 29.13, 29.09, 27.70, 27.19, 27.14, 25.02, 22.67, 19.07 (2), 14.10; IR (NaCl, film) $v_{max}$ 2925.2, 2853.9, 1739.7, 1466.2, 1378.6, 1172.6, 1012.6; FABMS m/z (M+H$^+$) 339.

H(Oleyl Aldehyde) as Illustrated in FIG. 3

Prepared as described in the literature (JOC 1978, 43,2480–2482).

CF$_3$as Illustrated in FIG. 3

Prepared as previously described (JACS, 1996, 118, 5938–5945).

ClCH$_2$ as Illustrated in FIG. 3

Prepared as previously described (JACS, 1996, 118, 5938–5945).

N$_2$CH as Illustrated in FIG. 3

Prepared as previously described (JACS, 1996, 118, 5938–5945).

Oleyl Alcohol as Illustrated in FIG. 3

Prepared as described in the literature (JOC 1978, 43,2480–2482).

Oleyl Acetate

Purchased from Sigma.

Oleyl Amine

Purchased from Pfaltz and Bauer.

Oleyl Aldehyde Dimethyl Acetal as Illustrated in FIG. 3

Prepared as described in the literature (J Med Chem, 1989, 32, 1319–1322).

CoA-SCO Derivative as Illustrated in FIG. 3

Purchased from Sigma.

HOCH$_2$CH$_2$NH Derivative as Illustrated in FIG. 4

Prepared as previously described. (JACS, 1996, 118, 580–590).

(HOCH$_2$CH$_2$)$_2$NH Derivative as Illustrated in FIG. 4

Purchased from Pfaltz and Bauer.

HOCH$_2$CH$_2$NH Derivative as Illustrated in FIG. 4

Synthesized exactly as found in the general procedure for derivatives varying about carboxamide vida supra; all starting reagents were purchased from Aldrich, Acros, or Sigma: white solid: mp 55–56° C.; $^1$H NMR (CDCl$_3$, 400 MHz) δ6.87 (t, 1H, J=5.8 Hz), 5.28– 5.19 (m, 2H), 4.25 (br, 1H), 3.52 (s, 2H), 3.27 (q, 2H, J=6.2 Hz), 2.09 (t, 2H, J=7.6 Hz), 1.91–1.88 (m, 4H), 1.58 (p, 4H, J=6.0 Hz), 1.51 (p, 2H, J=7.1 Hz), 1.20–1.17 (m, 20H), 0.78 (t, 3H, J=6.8 Hz); $^{13}$C NMR (CDCl$_3$, 100 MHz) δ174.6, 129.8, 129.4, 58.9, 36.4, 36.0, 31.9, 31.7, 29.5, 29.3, 29.1, 29.0, 27.00, 26.96, 25.7, 22.5, 13.9; IR (film) $v_{max}$ 3290, 2917, 2848, 1634, 1550, 1462, 1412, 1216, 1052, 762 cm$^{-1}$; FABHRMS (NBA-NaI) m/z 340.3226 (C$_{21}$H$_{41}$NO$_2$+H$^+$ requires 340.3216).

HOCH$_2$CH(OAc)CH$_2$O Derivative as Illustrated in FIG. 4

Purchased from Sigma.

HOCH$_2$CH$_2$NH Derivative as Illustrated in FIG. 4

Purchased from Sigma.

(HOCH$_2$CH$_2$)$_2$NH Derivative as Illustrated in FIG. 4

Synthesized exactly as found in the general procedure for derivatives varying about carboxamide vida supra; all starting reagents were purchased from Aldrich, Acros, or Sigma: orange oil; $^1$H NMR (CDCl$_3$, 500 MHz) δ7.68 (br, 1H), 7.50 (br, 1H), 5.38–5.29 (m, 8H), 3.78 (t, 2H, J=5.0 Hz), 3.73 (t, 2H, J=5.3 Hz), 3.50 (t, 2H, J=5.0 Hz), 3.45 (t, 2H, J=5.0 Hz), 2.81–2.77 (m, 6H), 2.36 (t, 2H, J=7.5 Hz), 2.09 (q, 2H, J=6.0 Hz), 2.02 (q, 2H, J=7.0 Hz), 1.67 (p, 2H, J=7.5 Hz), 1.34–1.22 (m, 6H), 0.85 (t, 3H, J=6.8 Hz); $^{13}$C NMR (CDCl$_3$, 125 MHz) δ175.3, 130.5, 129.2, 128.7, 128.5, 128.1 (2), 127.8, 127.4, 61.3, 60.7, 52.2, 50.5, 32.8, 31.4, 29.3, 27.2, 26.6, 25.6 (3), 25.0, 22.5, 14.0; IR (film) $v_{max}$ 3375, 3011, 2956, 2926, 2857, 1727, 1621, 1455, 1270, 1072 cm$^{-1}$; FABHRMS (NBA-CsI) m/z 524.2152 ($C_{24}H_{41}NO_3$+Cs$^+$ requires 524.2141).

Figure 19:
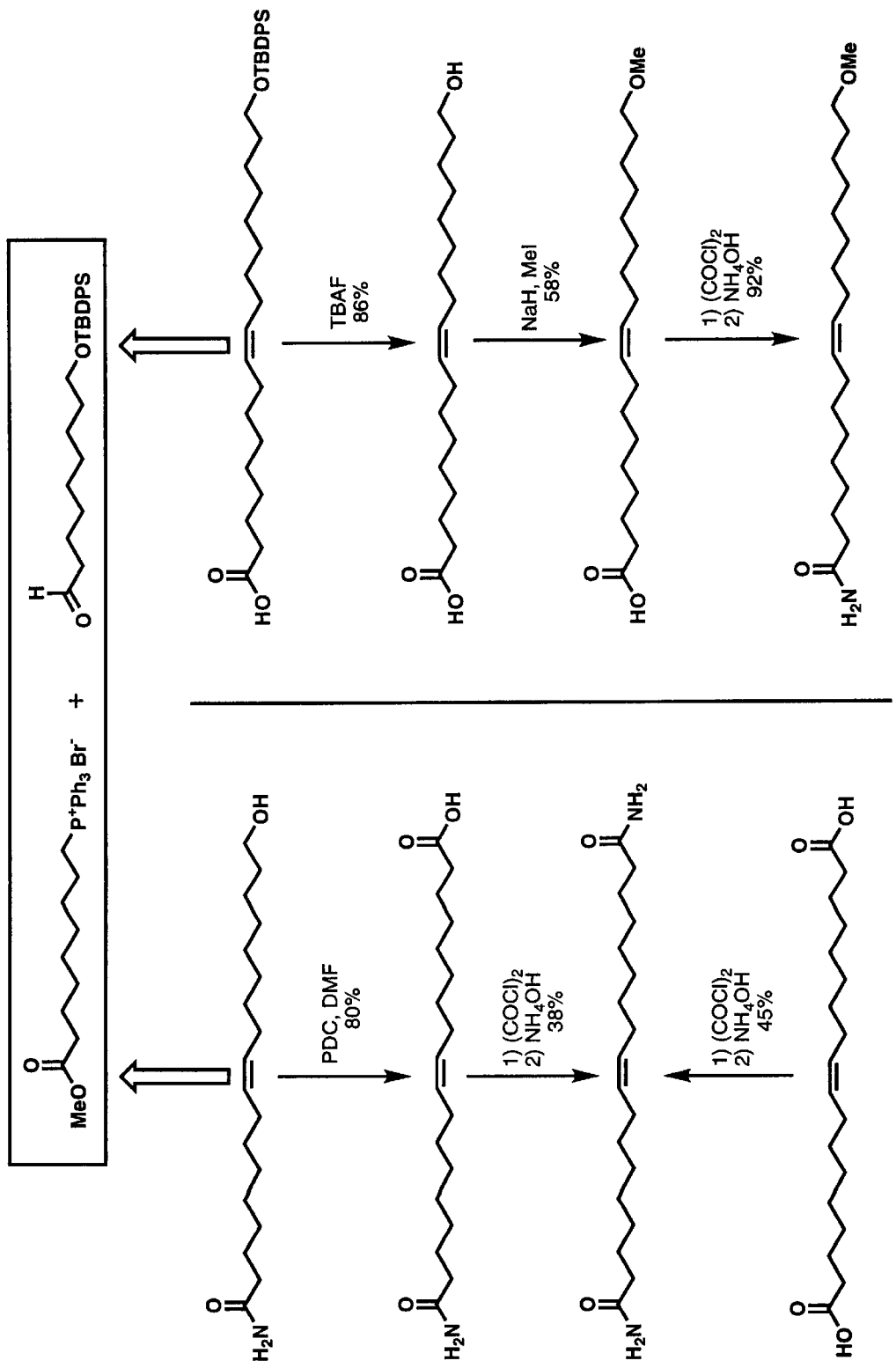
FIG. 19 illustrates various syntheses for analogs including a Wittig type approach for the synthesis of analogs (see scheme 5 for data for these compounds).

$CH_2OCH_3$ Derivative as Illustrated in FIG. 5 and Scheme Shown in FIG. 19 (Left Side)

A solution of 18-TBDPS-acid (prepared as described in JACS, 1996, 118, 580–590) (390.1 mg, 0.58 mmol, 1 eq) in THF (2 mL) under $N_2$ at 25° C. was treated with TBAF (1M in THF, 1.2 mL, 1.2 mmol, 2 eq) for 2 h. Water (30 mL) was added and the aqueous layer was extracted with EtOAc (3×30 mL). The organic layers were dried ($Na_2SO_4$), filtered, and concentrated in vacuo. The crude product was chromatographed ($SiO_2$, 2×8 cm, 20–100% EtOAc/hexanes, gradient elution) to afford 18-OH-acid (149.1 mg, 86%) as a white solid: 25° C.; $^1$H NMR (CDCl$_3$, 400 MHz) δ6.47 (br, 1H), 5.35–5.26 (m, 2H), 3.60 (t, 2H, J=6.7 Hz), 2.29 (t, 2H, J=7.5 Hz), 1.98–1.95 (m, 4H), 1.60–1.49 (m, 4H), 1.27 (s, 18H); $^{13}$C NMR (CDCl$_3$, 100 MHz) δ179.2, 129.9, 129.8, 62.8, 34.1, 32.5, 29.7, 29.6, 29.4, 29.3, 29.2, 29.1, 29.0 (2), 27.11, 27.07, 25.7, 24.7; IR (film) $v_{max}$ 3355, 2926, 2853, 1710, 1462, 1409, 1246, 1054, 722 cm$^{-1}$; FABHRMS (NBA-NaI) m/z 321.2415 ($C_{18}H_{34}O_3$+Na$^+$ requires 321.2406).

A solution of 18-OH-acid (67.7 mg, 0.23 mmol, 1 eq) in anhydrous THF (2.2 mL) under $N_2$ at 0° C. was treated with NaH (60%, 28.1 mg, 0.70 mmol, 3 eq) for 15 min. MeI (72 μL, 1.16 mmol, 5 eq) was added and the reaction was warmed to 25° C. and allowed to stir for 5 h. A second portion of MeI (140 μL, 2.25 mmol, 10 eq) was added and the reaction was stirred for an additional 14 h. Water (30 mL) was added and the aqueous layer was extracted with EtOAc (3×30 mL). The organic layers were dried ($Na_2SO_4$), filtered, and concentrated in vacuo. The crude product was chromatographed ($SiO_2$, 2×8 cm, 20–100% EtOAc/hexanes, gradient elution) to afford 18-methoxy-acid (41.0 mg, 58%) as a clear oil; $^1$H NMR (CDCl$_3$, 400 MHz) δ5.35–5.27 (m, 2H), 3.35 (t, 2H, J=6.7 Hz), 3.31 (s, 3H), 2.31 (t, 2H, J=7.5 Hz), 1.99–1.96 (m, 4H), 1.64–1.50 (m, 4H), 1.28–1.27 (m, 18H); $^{13}$C NMR (CDCl$_3$, 100 MHz) δ179.7, 129.9, 129.7, 73.0, 58.4, 34.0, 29.7, 29.6, 29.5, 29.4, 29.2, 29.1, 29.0, 27.2, 27.1, 26.1, 24.7; IR (film) $v_{max}$ 2926, 2854, 1710, 1458, 1119 cm$^{-1}$; FABHRMS (NBA-NaI) m/z 335.2568 ($C_{19}H_{36}O_3$+Na$^+$ requires 335.2562).

A solution of 18-methoxy-acid (37.7 mg, 0.12 mmol, 1 eq) in anhydrous $CH_2Cl_2$ (0.6 mL) under $N_2$ at 0° C. was treated with oxalyl chloride (2M in $CH_2Cl_2$, 0.18 mL, 0.36 mmol, 3 eq). The reaction mixture was warmed to 25° C. and stirred for 3 h before the solvent was removed in vacuo. The residue was cooled to 0° C. and treated with excess concentrated $NH_4OH$ (1 mL). Water (30 mL) was added and the aqueous layer was extracted with EtOAc (3×30 mL). The organic layers were dried ($Na_2SO_4$), filtered, and concentrated in vacuo. The crude product was chromatographed ($SiO_2$, 2×5 cm, 50–100% EtOAc/hexanes, gradient elution) to afford $CH_2OCH_3$ (34.6 mg, 92%) as a white solid: mp 59–60° C.; $^1$H NMR (CDCl$_3$, 400 MHz) δ5.71 (br, 1H), 5.52 (br, 1H), 5.35–5.27 (m, 2H), 3.33 (t, 2H, J=6.7 Hz), 3.29 (s, 3H), 2.18 (t, 2H, J=7.6 Hz), 1.98–1.96 (m, 4H), 1.61–1.49 (m, 4H), 1.27–1.26 (m, 18H); $^{13}$C NMR (CDCl$_3$, 100 MHz) δ175.8, 129.9, 129.8, 72.9, 58.5, 35.9, 29.7, 29.64, 29.60, 29.4, 29.20, 29.18, 29.07, 27.14, 27.12, 26.1, 25.5; IR (film) $v_{max}$ 3356, 3191, 2922, 2851, 2358, 1660, 1633, 1469, 1410, 1120 cm$^{-1}$; FABHRMS (NBA-NaI) m/z 334.2730 ($C_{19}H_{37}O_2$N 30 Na$^+$ requires 334.2722).

$CH_2OH$ Derivative as Illustrated in FIG. 5 is commercially available from Aldrich.

$CONH_2$ Derivative as Illustrated in FIG. 5 and Scheme Shown in FIG. 19 (Left Side)

A solution of $CO_2H$ (73.8 mg, 0.24 mmol, 1 eq) in anhydrous $CH_2Cl_2$ (1.2 mL) under $N_2$ at 0° C. was treated with oxalyl chloride (2M in $CH_2Cl_2$, 0.36 mL, 0.72 mmol, 3 eq). The reaction mixture was warmed to 25° C. and stirred for 3 h in the dark before the solvent was removed in vacuo. The residue was cooled to 0° C. and treated with excess concentrated $NH_4OH$ (3 mL). Water (30 mL) was added and the aqueous layer was extracted with EtOAc (3×30 mL) and CHCl$_3$ (3×30 mL). The organic layers were dried ($Na_2SO_4$), filtered, and concentrated in vacuo. The crude product was chromatographed ($SiO_2$, 2×15 cm, 0–10% MeOH/EtOAc, gradient elution) to afford $CONH_2$ (27.8 mg, 38%) as a white solid: mp 128–129° C.; $^1$H NMR (CDCl$_3$, 400 MHz) δ5.47 (br, 4H), 5.35–5.28 (m, 2H), 2.20 (t, 4H, J=7.6 Hz), 1.98 (q, 4H, J=5.6 Hz), 1.61 (p, 4H, J=7.3 Hz), 1.29 (s, 12H); $^{13}$C NMR (CDCl$_3$, 100 MHz) δ175.6 (2), 129.9 (2), 35.9 (2), 29.6 (2), 29.2 (4), 29.0 (2), 27.1 (2), 25.5 (2); IR (film) $v_{max}$ 3385, 3186, 2921, 2848, 1647, 1419 cm$^{-1}$; FABHRMS (NBA-NaI) m/z 311.2691 ($C_{18}H_{34}N_2O_2$+H$^+$ requires 311.2699).

$CO_2H$ Derivative as Illustrated in FIG. 5

A solution of 18-hydroxy-amide (prepared as described in JACS, 1996, 118, 580–590) (101.2 mg, 0.34 mmol, 1 eq) in anhydrous DMF (3.4 mL) under $N_2$ was treated with PDC (644.0 mg, 1.71 mmol, 5 eq) at 25° C. for 5 h. Water (30 mL) was added and the mixture was extracted with EtOAc (3×30 mL). The organic layers were dried ($Na_2SO_4$), filtered, and concentrated in vacuo. The crude product was chromatographed ($SiO_2$, 2.5×15 cm, 5–10% EtOAc/hexanes, gradient elution) to afford $CO_2H$ (85.0 mg, 80%) as a white solid: mp 74–76° C.; $^1$H NMR (CDCl$_3$, 400 MHz) δ6.71 (br, 1H), 5.74 (br, 1H), 5.34–5.27 (m, 2H), 2.29 (t, 2H, J=7.5 Hz), 2.19 (t, 2H, J=7.6 Hz), 1.97 (m, 4H), 1.59 (m, 4H), 1.27 (s, 16H); $^{13}$C NMR (CDCl$_3$, 100 MHz) δ178.6, 177.5, 129.9, 129.8, 35.9, 34.2, 29.6, 29.5, 29.2, 29.10, 29.08, 29.02 (2), 28.9, 27.1, 27.0, 25.5, 24.8; IR (film) $v_{max}$ 3389, 3191, 3008, 2917, 2848, 1704, 1645, 1466, 1417 cm$^{-1}$; FABHRMS (NBA-CsI) m/z 444.1524 ($C_{18}H_{33}NO_3$+Cs$^+$ requires 444.1515).

OH Derivative as Illustrated in FIG. 6

Oleic glycine ethyl ester (OEt) (725.5 mg, 1.97 mmol, 1 equiv) was dissolved in 6 mL of THF/MeOH/$H_2O$ (3:1:1). The solution was treated with LiOH.$H_2O$ (236.6 mg, 5.63 mmol, 2.9 equiv) and stirred at 25° C. for 15 minutes. The solution was diluted with 1N HCl (30 mL) and extracted with EtOAc (3×30 mL). The organic layers were dried over $Na_2SO_4$, filtered, and concentrated in vacuo to afford (611.2 mg, 91%) of OH as a white solid. $^1$H NMR (CDCl$_3$, 400 MHz) δ7.04 (br, 1H), 6.26 (t, 1H, J=4.8 Hz), 5.36–5.27 (m, 2H), 4.04 (d, 2H, J=5.2 Hz), 2.24 (t, 3H, J=7.7 Hz), 1.97 (m, 4H), 1.61 (p, 2H, J=7.2 Hz), 1.27–1.24 (m, 20H), 0.85 (t, 3H, J=6.8 Hz); $^{13}$C NMR (CDCl$_3$, 100 MHz) δ174.6, 172.7, 130.0, 129.7, 41.5, 36.3, 31.9, 29.74, 29.68, 29.5, 29.3 (2), 29.19, 29.15, 29.1, 27.20, 27.15, 25.5, 22.7, 14.1; IR (NaCl, film) $v_{max}$ 3429, 3304, 2918, 2849, 1699, 1645, 1552, 1469, 1410, 1239, 718, 677 cm$^{-1}$; HRFABMS m/z (M+H$^+$) 340.2861 (requires m/z 340.2852); mp 90–91° C.

$NH_2$ Derivative as Illustrated in FIG. 6

Oleic glycine (OH) (325.6 mg, 0.96 mmol, 1 equiv), dry $CH_2Cl_2$ (16 mL), and concentrated ammonium hydroxide (225 μL) were combined under a $N_2$ atmosphere and cooled to 0° C. EDCI (573.1 mg, 1.93 mmol, 1 equiv) and DMAP (24.4 mg, 0.20 mmol, 0.2 equiv) were added and the reaction was stirred at 25° C. for 2.5 h. The solvent was removed in vacuo and the crude product was purified by chromatography (SiO$_2$, 3×18 cm, 0–10% methanol/EtOAc, gradient elution) to afford 231.1 mg (71%) of NH$_2$ as a white solid. $^1$H NMR (CD$_3$OD, 400 MHz) δ8.03 (br, 1H), 5.28–5.20 (m, 2H), 3.72 (d, 2H, J=1.4 Hz), 2.16 (t, 2H, J=7.6 Hz), 1.92 (m, 4H), 1.52 (p, 2H, J=7.2 Hz), 1.23–1.19 (m, 20H), 0.80 (t, 3H, J=6.9 Hz); $^{13}$C NMR (CDCl$_3$, 100 MHz) δ173.8, 171.0, 130.0, 129.7, 42.8, 36.4, 31.9, 29.8, 29.7, 29.5, 29.3, 29.2, 29.1, 27.21, 27.16, 25.6, 22.7, 14.1; IR (NaCl, film) υ$_{max}$ 3385, 3307, 3195, 2918, 2849, 1661, 1643, 1549, 1468, 1415 cm$^{-1}$; HRFABMS m/z (M+H$^+$) 339.3020 (requires m/z 339.3012); mp 124–125° C.

OEt Derivative as Illustrated in FIG. 6

Oleic acid (100 μL, 0.32 mmol, 1 equiv), glycine ethyl ester hydrochloride (45.9 mg, 0.33 mmol, 1 equiv), dry triethylamine (66 μL, .47 mmol, 1.5 equiv) and dry methylene chloride (5 mL) were combined under a N$_2$ atmosphere and cooled to 0° C. EDCI (107.0 mg, 0.36 mmol, 1.1 equiv) and DMAP (8.1 mg, 0.07 mmol, 0.2 equiv) were added and the reaction was allowed to stir at 25° C. for 4 h. The solvent was removed in vacuo and the crude product was chromatographed (SiO$_2$, 2×15 cm, 20%–33% EtOAc/hexanes, gradient elution) to afford OEt as a white solid (109.5 mg, 94%). 1H NMR (CDCl$_3$, 400 MHz) δ5.95 (br, 1H), 5.36–5.27 (m, 2H), 4.19 (quartet, 2H, J=7.1 Hz), 4.00 (d, 2H, J=5.1 Hz), 2.21 (t, 2H, J=7.6 Hz), 1.99 (m, 4H), 1.62 (p, 2H, J=7.2 Hz), 1.28–1.24 (m, 23H), 0.85 (t, 3H, J=6.8 Hz); $^{13}$C NMR (CDCl$_3$, 100 MHz) δ173.2, 170.1, 130.0, 129.7, 61.5, 41.3, 36.4, 31.9, 29.73, 29.67, 29.5, 29.3, 29.2, 29.1, 27.2, 27.1, 25.5, 22.7, 14.1; IR (NaCl, film) υ$_{max}$ 3311, 2918, 2849, 1739, 1647, 1552, 1465, 1413, 1375, 1213, 1032, 700 cm$^{-1}$; HRFABMS m/z (M+H$^+$) 368.3175 (requires m/z 368.3165); mp 32–33° C.

OH/R$_1$=Me Derivative as Illustrated in FIG. 6

Purchased from Sigma.

OEt/R$_1$=Me Derivative as Illustrated in FIG. 6: (Both Isomers)

To a solution of oleoyl sarcosine (OH) (200.7 mg, 0.57 mmol, 1 eq) in anhydrous THF (6 mL) was added DCC (158.9 mg, 0.77 mmol, 1.4 eq) and absolute EtOH (50 μL, 0.85 mmol, 1.5 eq). The reaction mixture was stirred at 25° C. for 22 h. The white precipitate was filtered off and water (30 mL) was added to the eluent. The aqueous layer was extracted with EtOAc (3×30 mL). The organic layers were dried (Na$_2$SO$_4$), filtered, and concentrated in vacuo. The crude product was chromatographed (SiO$_2$, 3×15 cm, 10–50% EtOAc/hexanes, gradient elution) to afford clear oil OEt (150.8 mg, 70%) as a mixture of isomers; $^1$H NMR (CDCl$_3$, 400 MHz) δ5.30–5.27 (m, 2H), 4.19–4.09 (m, 2H), 4.05+3.97 (s, 2H), 3.01+2.91 (s, 3H), [2.31(t, J=7.5 Hz)+ 2.16 (t, J=7.4 Hz)][2H], 1.96–1.94 (m, 4H), 1.59 (p, 2H, J=6.6 Hz), 1.26–1.20 (m, 23H), 0.82 (t, 3H, J=6.0 Hz); $^{13}$C NMR (CDCl$_3$, 100 MHz) major isomer (minor isomer) δ173.7 (173.3), 169.3 (169.0), 129.8, 129.7, (127.9, 127.8), (61.4), 60.9, (51.6), 49.3, 36.4, (34.7), 33.0, (32.8, 32.5), 31.8, (31.4), 29.64, 29.60, 29.4, 29.23, 29.19, 29.0, 27.1, (24.9), 24.8, 22.6, 14.03, 13.99; IR (film) υ$_{max}$ 2924, 2853, 1750, 1655, 1465, 1400, 1373, 1197, 1113, 1035 cm$^{-1}$; FABHRMS (NBA-NaI) m/z 404.3128 (C$_{23}$H$_{43}$O$_3$N+Na$^+$ requires 404.3141).

2(9-Octadecynamide) Derivative as Illustrated in FIG. 7

Synthesized exactly as found in the general procedure prepared in a manner analogous to 6; all starting reagents were purchased from Aldrich, Acros, or Sigma: mp 91–92° C.; $^1$H NMR (CDCl$_3$, 400 MHz) δ6.14 (br, 1H), 5.62 (br, 1H), 2.15 (t, 2H, J=7.6 Hz), 2.07 (t, 4H, J=7.0 Hz), 1.57 (p, 2H, J=7.1 Hz), 1.41 (p, 4H, J=7.4 Hz), 1.35–1.21 (m, 16H), 0.82 (t, 3H, J=6.9 Hz); $^{13}$C NMR (CDCl$_3$, 100 MHz) δ176.0, 80.2, 80.0, 35.9, 31.8, 29.1, 29.04 (3), 28.98, 28.8 (2), 28.6, 25.4, 22.6, 18.7, 18.6, 14.0; IR (film) υ$_{max}$ 3409, 2928, 2850, 1647, 1471, 1419, 712 cm$^{-1}$; FABHRMS (NBA-CsI) m/z 412.1636 (C$_{18}$H$_{33}$NO+Cs$^+$ requires 412.1616).

3 Derivative as Illustrated in FIG. 7

Prepared as previously described. (JACS, 1996, 118, 580–590).

4 Derivative as Illustrated in FIG. 7

Prepared as described in the literature (JACS, 1959, 81, 4256).

5 Derivative as Illustrated in FIG. 7

Synthesized exactly as found in the general procedure prepared in a manner analogous to 6; all starting reagents were purchased from Aldrich, Acros, or Sigma: mp 47–48° C.; $^1$H NMR (CDCl$_3$, 400 MHz) δ7.13–7.07 (m, 4H), 5.53 (br, 1H), 5.41 (br, 1H), 2.57 (td, 4H, J=7.9, 1.5 Hz), 2.20 (t, 2H, J=7.6 Hz), 1.62 (p, 2H, J=7.1 Hz), 1.55 (p, 4H, J=7.8 Hz), 1.34–1.26 (m, 16H), 0.86 (t, 3H, J=6.8 Hz); $^{13}$C NMR (CDCl$_3$, 100 MHz) δ175.6, 140.5, 140.4, 129.1, 129.0, 125.70, 125.66, 35.9, 32.7, 32.6, 31.9, 31.3, 31.2, 29.8, 29.6, 29.5, 29.3 (2), 29.2, 25.5, 22.7, 14.1; IR (film) υ$_{max}$ 3392, 3194, 2924, 2853, 1647, 1464, 1415, 746 cm$^{-1}$; FABHRMS (NBA-NaI) m/z 354.2776 (C$_{22}$H$_{37}$NO requires 354.2773).

Figure 20:
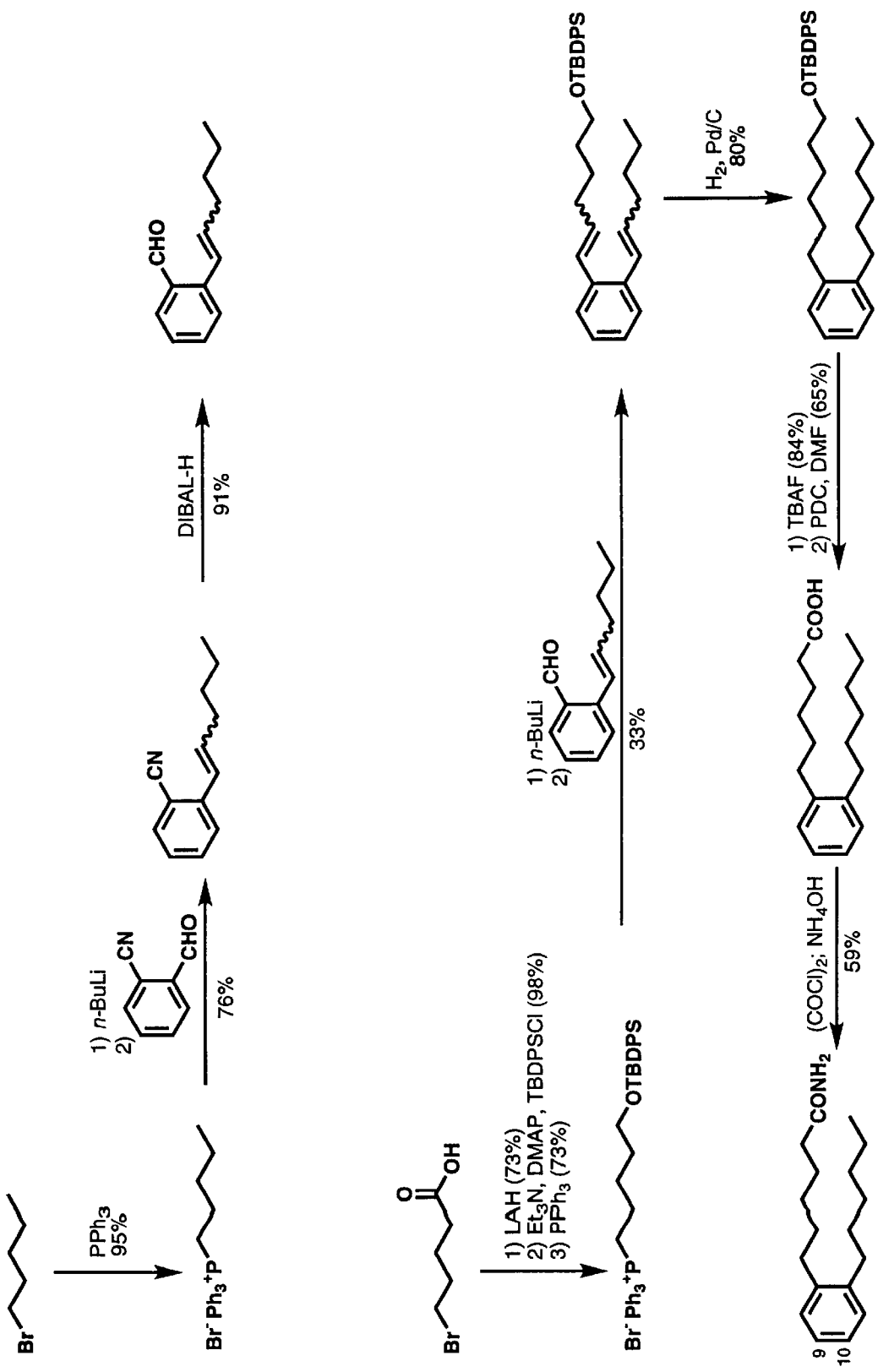
FIG. 20 illustrates a general synthesis of olefin derivatives (see scheme 7 for data for these compounds).

6 Derivative as Illustrated in FIG. 7 and Scheme Shown on FIG. 20

A solution of 1-bromopentane (1.0 mL, 8.1 mmol, 1 eq) and Ph$_3$P (2.32 g, 8.8 mmol, 1.1 eq) in anhydrous CH$_3$CN (6 mL) under N$_2$ was refluxed for 20 h. The reaction mixture was concentrated in vacuo and the crude product was chromatographed (SiO$_2$, 3×20 cm, 10% EtOAc/hexanes—50% iPrOH/EtOAc, gradient elution) to afford phosphonium salt (3.27 g, 98%) as a white foam; $^1$H NMR (CDCl$_3$, 400 MHz) δ7.84–7.73 (m, 9H), 7.69–7.65 (m, 6H), 3.78–3.71 (m, 2H), 1.58–1.57 (m, 4H), 1.25 (s, 2H, J=7.2 Hz), 0.78 (t, 3H, J=7.3 Hz); $^{13}$C NMR (CDCl$_3$, 100 MHz) δ134.9 (3, d, J=2 Hz), 133.6 (6, d, J=10 Hz), 130.4 (6, d, J=12 Hz), 118.3 (3, d, J=86 Hz), 32.3 (d, J=15 Hz), 22.9, 22.3, 22.2 (d, J=3 Hz), 13.6; IR (film) υ$_{max}$ 3405, 2921, 2864, 1438, 1112, 996, 749, 723, 690 cm$^{-1}$; ESI (M–Br$^+$) 333.

A solution of phosphonium salt (3.2 g, 7.74 mmol, 1.1 eq) in anhydrous THF (60 mL) under N$_2$ at –78° C. was treated with n-BuLi (2.0M, 7.0 mL, 14.0 mmol, 2.0 eq). The reaction mixture was warmed to 25° C. and allowed to stir for 10 min. The reaction was recooled to –78° C. and treated with a solution of 2-cyanobenzaldehyde (0.9119 g, 6.95 mmol, 1 eq) in anhydrous THF (15 mL). The reaction mixture was then warmed to 25° C. and stirred for 1 h before an aqueous solution of saturated NH$_4$Cl (100 mL) was added. The aqueous layer was extracted with EtOAc (3×100 mL) and the organic layers were dried (Na$_2$SO$_4$), filtered, and concentrated in vacuo. The crude product was chromatographed (SiO$_2$, 6×20 cm, 0–5% EtOAc/hexanes, gradient elution) to afford CN-alkene (0.9796 g, 76%) as a clear oil (mixture of E/Z isomers); $^1$H NMR (CDCl$_3$, 400 MHz) δ7.64–7.22 (m, 4H), [6.72 (d, J=15.7 Hz)+6.59 (d, J=11.6 Hz)][1H], [6.41 (dt, J=15.7, 7.0 Hz)+5.90 (dt, J=11.6, 7.5 Hz)][1H], [2.27 (qd, J=7.6, 1.4 Hz)+2.21 (qd, J=7.3, 1.7 Hz)][2H], 1.50–1.20 (m, 4H), [0.91 (t, J=7.2 Hz)+0.84 (t, J=7.2 Hz)][3H]; $^{13}$C NMR (CDCl$_3$, 100 MHz) δ141.3, 141.2, 137.4, 136.8, 132.8, 132.7, 132.6, 132.2, 129.4, 126.8, 125.8, 125.3, 125.0, 118.1, 118.0, 112.2, 110.4, 32.8, 31.6, 31.1, 28.4, 22.2, 13.9, 13.8; IR (film) υ$_{max}$ 2957, 2928, 2858, 2224, 1647, 1596, 1478, 1466, 1448, 966, 759 cm$^{-1}$; FABHRMS (NBA-NaI) m/z 186.1285 (C$_{13}$H$_{15}$N+H$^+$ requires 186.1283).

A solution of CN-alkene (0.9394 g, 5.1 mmol, 1 eq) in anhydrous toluene (10 mL) under $N_2$ at 0° C. was treated with DIBAL (1M, 5.6 mL, 5.6 mmol, 1.1 eq). The reaction mixture was stirred for 5 min before an aqueous saturated solution of $NH_4Cl$ (60 mL) was added. The mixture was stirred at 25° C. for 15 min before the aqueous layer was extracted with EtOAc (3×60 mL). The organic layers were dried ($Na_2SO_4$), filtered, and concentrated in vacuo. The crude product was chromatographed ($SiO_2$, 4×20 cm, 0–4% EtOAc/hexanes, gradient elution) to afford CHO-alkene (0.86 g, 91%) as a clear oil (mixture of E/Z isomers); $^1$H NMR ($CDCl_3$, 400 MHz) δ[10.26+10.22][s, 1H], [7.87 (dd, J=7.8, 1.4 Hz)+7.77 (dt, J=7.6, 0.9 Hz)][1H], 7.54–7.23 (m, 3H), [7.15 (dt, J=15.6, 1.5 Hz)+6.77 (d, J=11.5 Hz)][1H], [6.13 (dt, J=15.6, 6.9 Hz)+5.90 (dt, J=11.5, 7.5 Hz)][1H], [2.26 (qd, J=7.5, 1.5 Hz)+2.03 (qd, J=7.3, 1.6 Hz)][2H], 1.50–1.18 (m, 4H), [0.91 (t, J=7.3 Hz)+0.79 (t, J=7.3 Hz)] [3H]; $^{13}$C NMR ($CDCl_3$, 100 MHz) δ192.4, 141.0, 137.5, 136.2, 133.6, 133.5, 132.5, 130.5, 130.4, 128.4, 127.4, 127.1, 126.9, 125.6, 125.1, 33.0, 31.4, 31.2, 28.1, 22.21, 22.16, 13.9, 13.8; IR (film) $\upsilon_{max}$ 2957, 2928, 2871, 1695, 1597, 1566, 1480, 1466, 1451, 1389, 1289, 1196, 968, 762 $cm^{-1}$; FABHRMS (NBA-NaI) m/z 189.1280 ($C_{13}H_{16}O+H^+$ requires 189.1279).

A solution of 5-bromo-pentanol (0.9889 g, 5.9 mmol, 1 eq) in anhydrous $CH_2Cl_2$ (20 mL) under $N_2$ at 25° C. was treated with anhydrous $Et_3N$ (1.0 mL, 7.2 mmol, 1.2 eq), TBDPSCl (1.7 mL, 6.5 mmol, 1.1 eq) and DMAP (0.23 g, 1.9 mmol, 0.3 eq). The reaction mixture was stirred for 2 h before an aqueous solution of saturated $NH_4Cl$ (100 mL) was added. The aqueous layer was extracted with EtOAc (3×100 mL) and the organic layers were dried ($Na_2SO_4$), filtered, and concentrated in vacuo. The crude product was chromatographed ($Sio_2$, 5×20 cm, 0–20% EtOAc/hexanes, gradient elution) to afford TBDPSOH (2.35 g, 98%) as a clear oil; $^1$H NMR ($CDCl_3$, 400 MHz) δ7.66–7.60 (m, 4H) 7.44–7.33 (m, 6H), 3.64 (t, 2H, J=6.1 Hz), 3.37 (t, 2H, J=6.9 Hz), 1.82 (p, 2H, J=7.3 Hz), 1.59–1.45 (m, 4H), 1.03 (s, 9H); $^{13}$C NMR ($CDCl_3$, 100 MHz) δ135.6, 129.6, 127.6, 127.5, 63.5, 33.9, 32.5, 31.6, 26.8, 24.5, 19.2; IR (film) $\upsilon_{max}$ 3069, 2930, 2856, 2359, 1470, 1427, 1389, 1106, 822, 738, 700 $cm^{-1}$; FABHRMS (NBA-CsI) m/z 537.0235 ($C_{21}H_{29}OSiBr+Cs^+$ requires 537.0225).

A solution of TBDPSOH(2.35 g, 5.8 mmol, 1 eq) and $Ph_3P$ (1.67 g, 6.4 mmol, 1.1 eq) in anhydrous $CH_3CN$ (6 mL) under $N_2$ was refluxed for 22 h. The reaction mixture was concentrated in vacuo and the crude product was chromatographed ($SiO_2$, 5×20 cm, 20% EtOAc/hexanes—50% iPrOH/EtOAc, gradient elution) to afford TBDPSphosphonium salt (2.82 g, 73%) as a white foam; $^1$H NMR ($CDCl_3$, 400 MHz) δ7.84–7.72 (m, 9H), 7.67–7.62 (m, 6H), 7.58–7.55 (m, 4H), 7.38–7.29 (m, 6H), 3.84 (m, 2H), 3.57 (t, 2H, J=6.3 Hz), 1.75–1.51 (m, 6H), 0.95 (s, 9H); $^{13}$C NMR ($CDCl_3$, 100 MHz) δ135.4 (4), 134.9 (3, d, J=3 Hz), 133.8 (2), 133.7 (6, d, J=10 Hz), 130.4 (6, d, J=13 Hz), 129.5 (2), 127.6 (4), 118.3 (3, d, J=85 Hz), 63.4, 31.9, 26.8 (3), 25.3, 23.0, 22.4 (d, J=3 Hz), 19.1; IR (film) $\upsilon_{max}$ 3394, 2928, 2856, 2359, 1438, 1111, 996, 743, 703, 689 $cm^{-1}$; ESI (M-Br$^+$) 587.

A solution of TBDPSphosphonium salt (2.5783 g, 3.9 mmol, 1.1 eq) in anhydrous THF (25 mL) under $N_2$ at −78° C. was treated with n-BuLi (2.0M, 3.5 mL, 7.0 mmol, 2 eq). The reaction mixture was warmed to 25° C. and allowed to stir for 10 min. The reaction was recooled to −78° C. and treated with a solution of CHO-alkene (0.66 g, 3.5 mmol, 1 eq) in anhydrous THF (10 mL). The reaction mixture was then warmed to 25° C. and stirred for 1 h before an aqueous solution of saturated $NH_4Cl$ (60 mL) was added. The aqueous layer was extracted with EtOAc (3×60 mL) and the organic layers were dried ($Na_2SO_4$), filtered, and concentrated in vacuo. The crude product was chromatographed ($SiO_2$, 3×20 cm, 0–20% EtOAc/hexanes, gradient elution) to afford alkene-alkene (0.57 g, 33%) as a clear oil (mixture of E/Z isomers); $^1$H NMR ($CDCl_3$, 400 MHz) δ7.67–7.57 (m, 4H), 7.45–7.33 (m, 7H), 7.24–7.09 (m, 3H), 6.63–6.35 (m, 2H), 6.14–5.61 (m, 2H), 3.70–3.58 (m, 2H), 2.21–2.06 (m, 4H), 1.64–1.23 (m, 8H), 1.04–1.01 (m, 9H), 0.94–0.80 (m, 3H); $^{13}$C NMR ($CDCl_3$, 100 MHz) δ136.6, 136.5, 135.5, 134.1, 133.2, 133.0, 132.8, 129.5, 129.1, 129.0, 128.0, 127.8, 127.6, 126.8, 126.2, 125.3, 63.7, 33.0, 32.2, 32.1, 32.0, 28.19, 28.15, 26.8, 26.0, 25.9, 25.7, 22.3, 19.2, 13.9; IR (film) $\upsilon_{max}$ 2929, 2857, 1473, 1428, 1111, 823, 740, 701 $cm^{-1}$; FABHRMS (NBA-CsI) m/z 629.2226 ($C_{34}H_{44}OSi+Cs^+$ requires 629.2216).

Alkene-alkene(0.4311 g, 0.87 mmol, 1 eq) was combined with 10% Pd/C (0.33 g) under Ar. Absolute EtOH (8 mL) was added and the atmosphere was purged to $H_2$. The reaction was stirred at 25° C. for 24 h. The crude product was filtered through Celite to afford alkane (347.3 mg, 80%) as a clear oil; $^1$H NMR ($CDCl_3$, 400 MHz) δ7.84–7.78 (m, 4H), 7.56–7.44 (m, 6H), 7.27–7.21 (m, 4H), 3.80 (t, 2H, J=6.5 Hz), 2.73 (td, 4H, J=7.9, 2.4 Hz), 1.70 (m, 6H), 1.58–1.42 (m, 10H), 1.19 (s, 9H), 1.02 (t, 3H, J=7.0 Hz); $^{13}$C NMR ($CDCl_3$, 100 MHz) δ140.5, 140.4, 135.6, 134.1, 129.5, 129.1, 127.6, 125.7, 63.9, 32.7, 32.6, 32.5, 31.7, 31.3, 29.50, 29.46, 26.9, 25.7, 22.6, 19.2, 14.1; IR (film) $\upsilon_{max}$ 3070, 2928, 2856, 1956, 1888, 1823, 1589, 1471, 1427, 1389, 1361, 1188, 1111, 1007, 939, 910, 823, 740, 701, 614 $cm^{-1}$; FABHRMS (NBA-CsI) m/z 633.2525 ($C_{34}H_{48}OSi+Cs^+$ requires 633.2529).

A solution of alkane (325.7 mg, 0.65 mmol, 1 eq) in anhydrous THF (6 mL) under $N_2$ was treated with TBAF (1M in THF, 1.3 mL, 1.3 mmol, 2 eq) and stirred at 25° C. for 1.5 h. Water (30 mL) was added and the aqueous layer was extracted with EtOAc (3×30 mL). The organic layers were dried ($Na_2SO_4$), filtered, and concentrated in vacuo. The crude product was chromatographed ($SiO_2$, 2.5×15 cm, 10–33% EtOAc/hexanes, gradient elution) to afford alcohol (142.7 mg, 84%) as a clear oil; $^1$H NMR ($CDCl_3$, 400 MHz) δ7.18–7.11 (m, 4H), 3.64 (t, 2H, J=6.6 Hz), 2.66–2.61 (m, 4H), 1.64–1.57 (m, 6H), 1.45–1.32 (m, 10H), 0.94 (t, 3H, J=6.9 Hz); $^{13}$C NMR ($CDCl_3$, 100 MHz) δ140.4, 140.2, 129.02, 128.98, 125.7, 125.6, 62.7, 32.6 (2), 32.5, 31.7, 31.22, 31.20, 29.5, 29.4, 25.6, 22.6, 14.0; IR (film) $\upsilon_{max}$ 3340, 2928, 2856, 1489, 1463, 1055, 750 $cm^{-1}$; FABHRMS (NBA-NaI) m/z 262.2308 ($C_{18}H_{30}O+.^+$requires 262.2297).

A solution of alcohol (128.9 mg, 0.49 mmol, 1 eq) in anhydrous DMF (1 mL) under $N_2$ was treated with PDC (0.91 g, 2.4 mmol, 5 eq) at 25° C. for 8 h. Water (30 mL) was added and the aqueous layer was extracted with EtOAc (3×30 mL). The organic layers were dried ($Na_2SO_4$), filtered, and concentrated in vacuo. The crude product was chromatographed ($SiO_2$, 2.5×15 cm, 20–50% EtOAc/hexanes, gradient elution) to afford acid (88.1 mg, 65%) as a clear oil; $^1$H NMR ($CDCl_3$, 400 MHz) δ7.16–7.10 (m, 4H), 2.61 (q, 4H, J=7.2 Hz), 2.37 (t, 2H, J=7.5 Hz), 1.70 (p, 2H, J=7.7 Hz), 1.59 (septet, 4H, J=7.7 Hz), 1.48–1.30 (m, 8H), 0.90 (t, 3H, J=7.0 Hz); 13C NMR ($CDCl_3$, 100 MHz) δ180.3, 140.5, 140.0, 129.1, 129.0, 125.8, 125.7, 34.0, 32.7, 32.4, 31.7, 31.3, 30.9, 29.4, 29.1, 24.6, 22.6, 14.0; IR (film) $\upsilon_{max}$ 2928, 2858, 2359, 1709, 1489, 1462, 1412, 1287, 1242, 941, 751 $cm^{-1}$; FABHRMS (NBA-NaI) m/z 299.1976 ($C_{18}H_{28}O_2+Na^+$ requires 299.1987).

A solution of acid (62.3 mg, 0.23 mmol, 1 eq) in anhydrous $CH_2Cl_2$ (1.2 mL) under $N_2$ at 0° C. was treated with oxalyl chloride (2M in $CH_2Cl_2$, 0.34 mL, 0.68 mmol, 3 eq). The reaction mixture was warmed to 25° C. and stirred for 3 h before the solvent was removed in vacuo. The residue was cooled to 0° C. and treated with excess concentrated $NH_4OH$ (5 mL). Water (30 mL) was added and the aqueous layer was extracted with EtOAc (3×30 mL). The organic layers were dried ($Na_2SO_4$), filtered, and concentrated in vacuo. The crude product was chromatographed ($SiO_2$, 2.5×15 cm, 33–66% EtOAc/hexanes, gradient elution) to afford 6 (36.9 mg, 59%) as a white solid; mp 58–59° C.; $^1$H NMR ($CDCl_3$, 400 MHz) δ7.14–7.08 (m, 4H), 5.91 (br, 1H), 5.49 (br, 1H), 2.58 (q, 4H, J=6.4 Hz), 2.20 (t, 2H, J=7.6 Hz), 1.66 (hextet, 2H, J=7.7 Hz), 1.55 (hex, 4H, J=8.4 Hz), 1.45–1.28 (m, 8H), 0.88 (t, 3H, J=6.8 Hz); $^{13}$C NMR ($CDCl_3$, 100 MHz) δ175.7, 140.5, 140.0, 129.1, 129.0, 125.8, 125.7, 35.8, 32.6, 32.4, 31.7, 31.2, 30.9, 29.4, 29.2, 25.4, 22.6, 14.1; IR (film) $\upsilon_{max}$ 3366, 3195, 2925, 2855, 1664, 1629, 1491, 1465, 1412, 750 $cm^{-1}$; FABHRMS (NBA-NaI) nm/z 276.2329 ($C_{18}H_{29}ON+H^+$ requires 276.2327).

7 Derivative as Illustrated in FIG. 7

Synthesized exactly as found in the general procedure prepared in a manner analogous to 6; all starting reagents were purchased from Aldrich, Acros, or Sigma: white solid; mp 95–96° C.; $^1$H NMR ($CDCl_3$, 400 MHz) δ7.06 (s, 4H), 5.58 (br, 1H), 5.40 (br, 1H), 2.54 (t, 4H, J=7.8 Hz), 2.18 (t, 2H, J=7.6 Hz), 1.57 (m, 6H), 1.35–1.25 (m, 12H), 0.86 (t, 3H, J=6.9 Hz); $^{13}$C NMR ($CDCl_3$, 100 MHz) δ175.6, 140.2, 139.7, 128.22 (2), 128.19 (2), 35.9, 35.5, 35.4, 31.8, 31.6, 31.3, 29.3, 29.2, 29.0, 28.9, 25.4, 22.7, 14.1; IR (film) $\upsilon_{max}$ 3388, 3187, 2923, 2851, 1645, 1514, 1463, 1416, 1121, 810 $cm^{-1}$; FABHRMS (NBA-NaI) m/z 304.2651 ($C_{20}H_{33}ON+H^+$ requires 304.2640).

8 Derivative as Illustrated in FIG. 7 and Scheme Shown on FIG. 20

Synthesized exactly as found in the general procedure prepared in a manner analogous to 6; all starting reagents were purchased from Aldrich, Acros, or Sigma: white solid; mp 87–88° C.; $^1$H NMR ($CDCl_3$, 400 MHz) δ7.16 (t, 1H, J=7.7 Hz), 6.96 (t, 3H, J=6.6 Hz), 5.66 (br, 1H), 5.42 (br, 1H), 2.55 (t, 4H, J=7.8 Hz), 2.19 (t, 2H, J=6.0 Hz), 1.60 (septet, 6H, J=8.0 Hz), 1.37–1.28 (m, 10H), 0.86 (t, 3H, J=6.9 Hz); $^{13}$C NMR ($CDCl_3$, 100 MHz) δ175.8, 142.8, 142.5, 128.5, 128.0, 125.6, 125.5, 35.92, 35.85, 35.81, 31.7, 31.5, 31.3 29.02 (2), 29.00, 25.3, 22.5, 14.1; IR (film) $\upsilon_{max}$ 3352, 3191, 2925, 2854, 1660, 1630, 1466, 1409, 1341, 1311, 1253, 1202, 1138, 896, 777, 702 $cm^{-1}$; FABHRMS (NBA-NaI) m/z 312.2312 ($C_{19}H_{31}ON+Na^+$ requires 312.2303).

Figure 8:
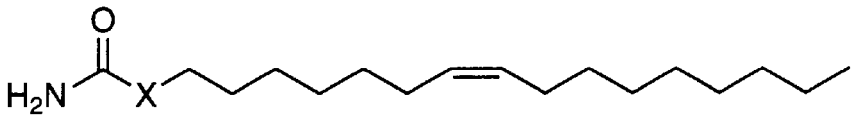
FIG. 8 illustrates linker modification substituted analogs with % inhibition of gap junction-mediated dye transfer wherein the indicated footnotes are represented as follows: (a) Inhibition of GAP junction-mediated dye transfer, see FIG. 2; (b) Not done; (c) Tested at 150 mM; (d) Reversible; see FIGS. 21 and 22 for synthetic routes for some of these compounds.
Figure 21:
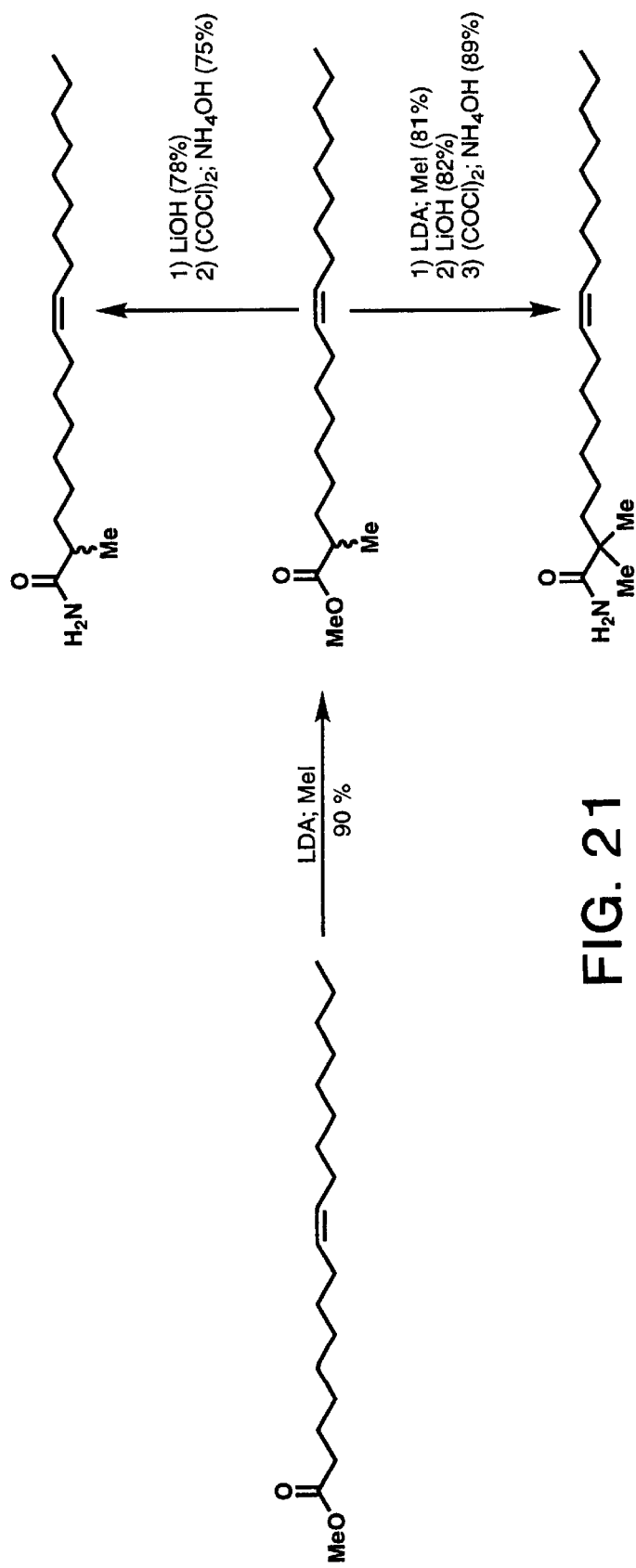
FIG. 21 illustrates the synthesis of various α-methyl derivatives (see scheme 8 for data for these compounds).

$CH(CH_3)$ Derivative as Illustrated in FIG. 8 and Scheme Shown on FIG. 21

A fresh solution of LDA was prepared at −78° C. under Ar from anhydrous diisopropylamine (0.47 mL, 3.35 mmol, 2.2 eq) and n-BuLi (2.2M in hexanes, 1.4 mL, 3.1 mmol, 2 eq) in anhydrous THF (6 mL). A solution of methyl oleate (0.4556 g, 1.54 mmol, 1 eq) in THF (1 mL) was added dropwise at −78° C. After 50 min of additional stirring, MeI (0.96 mL, 15.4 mmol, 10 eq) was added and the reaction mixture was allowed to warm to 25° C. and stir for 12 h. Saturated aqueous $NH_4Cl$ (30 mL) was added to the dark orange solution and the aqueous layer was extracted with EtOAc (3×30 mL). The organic layers were dried ($Na_2SO_4$), filtered, and concentrated in vacuo. The crude product was chromatographed ($SiO_2$, 2×15 cm, 0–5% EtOAc/hexanes, gradient elution) to afford α-Me-ester (0.4276 g, 90%) as a clear oil; $^1$H NMR ($CDCl_3$, 500 MHz) δ5.33–5.30 (m, 2H), 3.64 (s, 3H), 2.40 (s, 1H, J=7.0 Hz), 2.00–1.96 (m, 4H), 1.64–1.60 (m, 1H), 1.39–1.24 (m, 21H), 1.11 (d, 3H, J=7.0 Hz), 0.85 (t, 3H, J=6.8 Hz); $^{13}$C NMR ($CDCl_3$, 125 MHz) δ177.4, 130.0, 129.7, 51.4, 39.4, 33.8, 31.9, 29.8, 29.7, 29.5, 29.4, 29.3, 29.1, 27.2, 27.1, 22.7, 17.0, 14.1; IR (film) $\upsilon_{max}$ 2925, 2854, 1741, 1462, 1195, 1157, 723 $cm^{-1}$; FABHRMS (NBA-CsI) m/z 443.1938 ($C_{20}H_{38}O_2+Cs^+$ requires 443.1926).

A solution of α-Me-ester (150.5 mg, 0.48 mmol, 1 eq) in THF/MEOH/$H_2O$ (3:1:1; 5 mL) was treated with LiOH (67.1 mg, 1.6 mmol, 3.3 eq) and stirred at 25° C. for 15 h. A second portion of LiOH (66.1 mg, 1.58 mmol, 3.3 eq) was added and the reaction was stirred for an additional 7 h. Aqueous HCl (1N, 30 mL) was added and the aqueous layer was extracted with EtOAc (3×30 mL). The organic layers were dried ($Na_2SO_4$), filtered, and concentrated in vacuo. The crude product was chromatographed ($SiO_2$, 2×15 cm, 5–20% EtOAc/hexanes, gradient elution) to afford α-Me-acid (111.6 mg, 78%) as a clear oil; $^1$H NMR ($CDCl_3$, 400 MHz) δ5.37–5.29 (m, 2H), 2.43 (s, 1H, J=6.9 Hz), 1.99 (m, 4H), 1.66 (p, 1H, J=7.2 Hz), 1.43–1.25 (m, 21H), 1.15 (d, 3H, J=7.0 Hz), 0.86 (t, 3H, J=6.8 Hz); $^{13}$C NMR ($CDCl_3$, 125 MHz) δ183.5, 130.0, 129.7, 39.4, 33.5, 31.9, 29.8, 29.7, 29.5, 29.4, 29.3, 29.1, 27.2, 27.14, 27.10, 22.7, 16.8, 14.1; IR (film) $\upsilon_{max}$ 2925, 2854, 1708, 1466, 1291, 1239, 941, 723 $cm^{-1}$; FABHRMS (NBA-NaI) m/z 297.2797 ($C_{19}H_{36}O_2+H^+$ requires 297.2794).

A solution of α-Me-acid (94.4 mg, 0.32 mmol, 1 eq) in anhydrous $CH_2Cl_2$ (1.6 mL) under $N_2$ at 0° C. was treated with oxalyl chloride (2M in $CH_2Cl_2$, 0.48 mL, 0.96 mmol, 3 eq). The reaction mixture was warmed to 25° C. and stirred for 3 h before the solvent was removed in vacuo. The residue was cooled to 0° C. and treated with excess concentrated $NH_4OH$ (1 mL). Water (30 mL) was added and the aqueous layer was extracted with EtOAc (3×30 mL). The organic layers were dried ($Na_2SO_4$), filtered, and concentrated in vacuo. The crude product was chromatographed ($SiO_2$, 2×5 cm, 33–50% EtOAc/hexanes, gradient elution) to afford $CH(CH_3)$ (70.3 mg, 75%) as a white solid: mp 43–44° C.; $^1$H NMR ($CDCl_3$, 400 MHz) δ6.20 (br, 1H), 5.59 (br, 1H), 5.33–5.24 (m, 2H), 2.20 (s, 1H, J=6.8 Hz), 1.98–1.93 (m, 4H), 1.61–1.54 (m, 1H), 1.36–1.22 (m, 21H), 1.10 (d, 3H, J=6.9 Hz), 0.83 (t, 3H, J=6.9 Hz); $^{13}$C NMR ($CDCl_3$, 100 MHz) δ179.7, 129.9, 129.7, 40.8, 34.2, 31.8, 29.7, 29.6, 29.5, 29.2, 29.1, 27.3, 27.13, 27.08, 22.6, 17.7, 14.0; IR (film) $\upsilon_{max}$ 3360, 3186, 2922, 2852, 1654, 1628, 1466, 1414, 1376, 1140, 722, 697 $cm^{-1}$; FABHRMS (NBA) m/z 296.2959 ($C_{19}H_{37}NO+H^+$ requires 296.2953).

$C(CH_3)_2$ Derivative as Illustrated in FIG. 8 and Scheme Shown on FIG. 21

A fresh solution of LDA was prepared at −78° C. under Ar from anhydrous diisopropylamine (0.20 mL, 1.4 mmol, 2.2 eq) and n-BuLi (2.2M in hexanes, 0.6 mL, 1.3 mmol, 2 eq) in anhydrous THF (2.6 mL). A solution of α-Me-ester (0.2024 g, 0.65 mmol, 1 eq) in THF (0.4 mL) was added dropwise at −78° C. After 50 min of additional stirring, MeI (0.41 mL, 6.6 mmol, 10 eq) was added and the reaction mixture was allowed to warm to 25° C. and stir for 17 h. Saturated aqueous $NH_4Cl$ (30 mL) was added and the aqueous layer was extracted with EtOAc (3×30 mL). The organic layers were dried ($Na_2SO_4$), filtered, and concentrated in vacuo. The crude product was chromatographed ($SiO_2$, 2×8 cm, 0–5% EtOAc/hexanes, gradient elution) to afford α,α-diMe-ester (170.9 mg, 81%) as a clear oil; $^1$H NMR ($CDCl_3$, 400 MHz) δ5.34–5.25 (m, 2H), 3.61 (s, 3H), 1.99–1.94 (m, 4H), 1.48–1.44 (m, 2H), 1.27–1.23 (m, 20H), 1.11 (s, 6H), 0.84 (t, 3H, J=6.8 Hz); $^{13}$C NMR ($CDCl_3$, 100 MHz) δ178.5, 129.9, 129.7, 51.5, 42.2, 40.8, 31.9, 30.0, 29.7, 29.6, 29.5, 29.3, 29.1, 27.14, 27.11, 25.1, 24.9, 22.6, 14.0; IR (film) $\upsilon_{max}$ 2926, 2854, 1736, 1464, 1192, 1152 cm$^{-1}$; FABHRMS (NBA-NaI) m/z 325.3101 (C$_{21}$H$_{40}$O$_2$+H$^+$ requires 325.3107).

A solution of α,α-diMe-ester (157.6 mg, 0.49 mmol, 1 eq) in THF/MEOH/H$_2$O (3:1:1; 5 mL) was treated with LiOH (408.5 mg, 9.74 mmol, 20 eq) and stirred at 25° C. for 19 h. A second portion of LiOH (408.7 mg, 9.74 mmol, 20 eq) was added and the reaction was stirred for an additional 26 h. A third portion of LiOH (392.0 mg, 9.34 mmol, 19 eq) was added and the reaction was stirred for 47 h at 25° C. and 23 h at 70° C. Aqueous HCl (1N, 30 mL) was added and the aqueous layer was extracted with EtOAc (3×30 mL). The organic layers were dried (Na$_2$SO$_4$), filtered, and concentrated in vacuo. The crude product was chromatographed (SiO$_2$, 2×8 cm, 5–50% EtOAc/hexanes, gradient elution) to afford α,α-diMe-acid (123.4 mg, 82%) as a clear oil; $^1$H NMR (CDCl$_3$, 400 MHz) δ5.37–5.28 (m, 2H), 2.00–1.97 (m, 4H), 1.51– 1.49 (m, 2H), 1.32–1.25 (m, 20H), 1.17 (s, 6H), 0.86 (t, 3H, J=6.8 Hz); $^{13}$C NMR (CDCl$_3$, 100 MHz) δ185.3, 130.0, 129.8, 42.1, 40.5, 31.9, 30.0, 29.8, 29.7, 29.5, 29.3, 29.1, 27.20, 27.16, 24.9, 24.8, 22.7, 14.1; IR (film) $\upsilon_{max}$ 2925, 2854, 1701, 1467, 1277, 1200, 938 cm$^{-1}$; FAB-HRMS (NBA-NaI) m/z 333.2778 (C$_{20}$H$_{38}$O$_2$+Na$^+$ requires 333.2770).

A solution of α,α-diMe-acid (101.5 mg, 0.33 mmol, 1 eq) in anhydrous CH$_2$Cl$_2$ (1.6 mL) under N$_2$ at 0° C. was treated with oxalyl chloride (2M in CH$_2$Cl$_2$, 0.49 mL, 0.98 mmol, 3 eq). The reaction mixture was warmed to 25° C. and stirred for 3 h before the solvent was removed in vacuo. The residue was cooled to 0° C. and treated with excess concentrated NH$_4$OH (1 mL). Water (30 mL) was added and the aqueous layer was extracted with EtOAc (3×30 mL). The organic layers were dried (Na$_2$SO$_4$), filtered, and concentrated in vacuo. The crude product was chromatographed (SiO$_2$, 2×5 cm, 33–50% EtOAc/hexanes, gradient elution) to afford C(CH$_3$)$_2$ (90.5 mg, 89%) as a white solid: mp 61–62° C.; $^1$H NMR (CDCl$_3$, 400 MHz) δ6.10 (br, 1H), 5.61 (br, 1H), 5.34–5.26 (m, 2H), 1.97–1.94 (m, 4H), 1.47–1.42 (m, 2H), 1.30–1.23 (m, 20H), 1.13 (s, 6H), 0.84 (t, 3H, J=6.8 Hz); $^{13}$C NMR (CDCl$_3$, 100 MHz) δ181.0, 129.9, 129.7, 41.9, 41.3, 31.8, 30.0, 29.70, 29.67, 29.5, 29.3, 29.1, 27.2, 27.1, 25.4, 24.7, 22.7, 14.1; IR (film) ~$_{max}$ 3396, 3213, 3002, 2923, 2851, 1650, 1620, 1466, 1401, 1364, 1109 cm$^{-1}$; FAB-HRMS (NBA-CsI) m/z 310.3115 (C$_{20}$H$_{39}$NO+H$^+$ requires 310.3110).

"O" Derivative as Illustrated in FIG. 8 and Scheme Shown on FIG. 21

Commercially available from Aldrich.

"NH" Derivative as Illustrated in FIG. 8 and Scheme Shown on FIG. 21

Commercially available from Aldrich.

Figure 22:
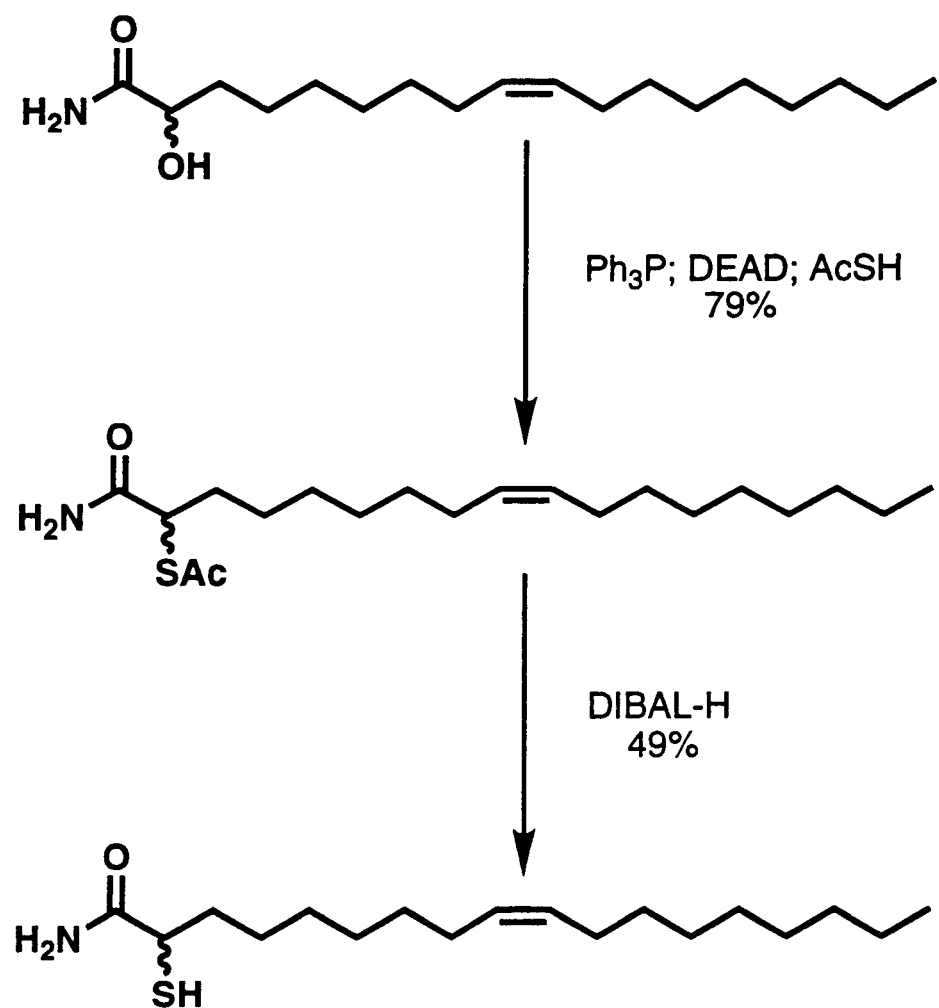
FIG. 22 illustrates the synthesis of various α-sulfhydryl derivatives (see scheme 8 for data for these compounds).

CH(SH) Derivative as Illustrated in FIG. 8 and Scheme Shown in FIG. 22

A solution of CH(SAc) (72.3 mg, 0.20 mmol, 1 eq) in anhydrous CH$_2$Cl$_2$ (4 mL) under N$_2$ at −78° C. was treated with DIBAL (1M in toluene, 0.61 mL, 0.61 mmol, 3 eq). The reaction mixture was allowed to stir for 1.5 h before a second portion of DIBAL (1M in toluene, 0.61 mL, 0.61 mmol, 3 eq) was added. After 30 min, the reaction was warmed to 25° C. before MeOH (2 mL) and aqueous HCl (5%, 30 mL) were added. The reaction mixture was allowed to stir for 15 min. The aqueous layers were extracted with CH$_2$Cl$_2$ (3×30 mL). The organic layers were dried (Na$_2$SO$_4$), filtered, and concentrated in vacuo. The crude product was chromatographed (SiO$_2$, 1×8 cm, 20–50% EtOAc/hexanes, gradient elution) to afford CH(SH) (31.5 mg, 49%) as a clear oil; $^1$H NMR (CDCl$_3$, 400 MHz) δ6.22 (br, 1H), 5.46 (br, 1H), 5.37–5.28 (m, 2H), 3.28 (q, 1H, J=6.5 Hz), 2.00–1.91 (m, 4H), 1.74–1.64 (m, 1H), 1.29–1.24 (m, 21H), 0.86 (t, 3H, J=6.8 Hz); $^{13}$C NMR (CDCl$_3$, 100 MHz) δ175.0, 130.1, 129.7, 43.0, 35.5, 32.0, 29.8, 29.6, 29.5, 29.3, 29.0, 27.2, 27.1, 22.7, 14.1; IR (film) $\upsilon_{max}$ 3363, 3186, 2923, 2853, 2362, 1662, 1458 cm$^{-1}$; FABHRMS (NBA-NaI) m/z 336.2341 (C$_{18}$H$_{35}$ONS+Na$^+$ requires 336.2337).

CH(SAc): Derivative as Illustrated in FIG. 8 and Scheme Shown in FIG. 22

A solution of Ph$_3$P (182.2 mg, 0.69 mmol, 2 eq) in anhydrous THF (3.5 mL) under N$_2$ at 0° C. was treated with DEAD (110 μL, 0.70 mmol, 2 eq) and allowed to stir for 30 min. Thiolacetic acid (50 μL, 0.70 mmol, 2 eq) was added followed by 2-hydroxy-9Z-octadecenamide (CH(OH); 103.0 mg, 0.35 mmol, 1 eq) in THF (2.2 mL). The reaction mixture was stirred at 0° C. for 2 h before the addition of saturated aqueous NaHCO$_3$ (30 mL). The aqueous layers were extracted with EtOAc (3×30 mL). The organic layers were dried (Na$_2$SO$_4$), filtered, and concentrated in vacuo. The crude product was chromatographed (SiO$_2$, 2×10 cm, 10–50% EtOAc/hexanes, gradient elution) to afford CH(SAc) (96.7 mg, 79%) as a clear oil; $^1$H NMR (CDCl$_3$, 400 MHz) δ6.12 (br, 1H), 5.63 (br, 1H), 5.35–5.26 (m, 2H), 3.91 (t, 1H, J=7.6 Hz), 2.35 (s, 3H), 2.02–1.90 (m, 5H), 1.67–1.58 (m, 1H), 1.42–1.24 (m, 20H), 0.85 (t, 3H, J=6.9 Hz); $^{13}$C NMR (CDCl$_3$, 100 MHz) δ196.6, 173.4, 130.0, 129.6, 45.6, 31.9, 30.3, 29.9, 29.7, 29.6, 29.5, 29.3, 29.1, 29.0, 27.2, 27.1, 22.7, 14.1; IR (film) $\upsilon_{max}$ 3448, 3352, 3186, 2923, 2853, 1682, 1457, 1396, 1353, 1259, 1116, 954 cm$^{-1}$; FABHRMS (NBA-NaI) m/z 378.2433 (C$_{20}$H$_{37}$O$_2$NS+Na$^+$ requires 378.2443).

CH(OH) Derivative as Illustrated in FIG. 8

Prepared as previously described (JACS, 1996, 118, 5938–5945).

CHCl Derivative as Illustrated in FIG. 8

Prepared as previously described (JACS, 1996, 118, 5938–5945).

C(=O) Derivative as Illustrated in FIG. 8

Prepared as previously described (JACS, 1996, 118, 5938–5945).

C(=O)CH$_2$ Derivative as Illustrated in FIG. 8

Prepared as previously described (JACS, 1996, 118, 5938–5945)

Synthesis of 1-Bromo-10Z-nonadecen-2-One as Shown in FIG. 3

1-Diazo-10Z-nonadecen-2-one (15, 92 mg, 0.30 mmol, 1 equiv; synthesis described herein) was treated with a solution of EtOAc saturated with HBr (1.5 mL). The reaction mixture was stirred at 25° C. for 25 min. The solvent was removed by a stream of N$_2$ and the crude product was chromatographed (SiO2, 2 to 8 cm, 0–5% EtOAc-hexanes gradient elution) to afford 41 (99 mg, 92%) as clear oil: $^1$H NMR (CDCl3, 400 MHz) d 5.37–5.28 (m, 2H), 3.86 (s, 2H), 2.62 (t, 2H, J=7.4 Hz), 2.02–1.96 (m, 4H), 1.59 (m, 2H), 1.28–1.24 (m, 20H), 0.86 (t, 3H, J=6.9 Hz); 13C NMR (CDCl3, 100 MHz) d 202.0, 130.0, 129.7, 39.8, 34.3, 31.9, 29.7, 29.6, 29.5, 29.3(2), 29.2, 29.04, 28.99, 27.2, 27.1, 23.8, 22.7, 14.1; IR (film) nmax 2924, 2853, 1718, 1560, 1262, 1103, 1026 cm −1; FABHRMS (NBA-NaI) m/z 381.1760 (C19H35BrO+Na$^+$ requires 381.1769).

Syntehsis of 9Z-Docosen-1-ol as Illustrated in FIG. 3

9-Bromononanol was protected (TBDPSCl, 1.1 equiv, Et$_3$N, 1.2 equiv, DMAP, 0.3 equiv, 25° C., 2.5 h) and treated with PPh$_3$ (1.3 equiv, CH$_3$CN, 85° C., 12 h) to generate a phosphonium salt (285 mg, 0.42 mmol, 1 equiv) that was dissolved in anhydrous THF (2.6 mL) under Ar at −78° C.

The solution was treated dropwise with KHMDS (0.5 M in toluene, 0.85 mL, 0.43 mmol, 1 equiv) and was stirred for 40 min at −78° C. before tridecanal (100 mL, 0.42 mmol, 1 equiv) was added. The reaction was warmed to 25° C. and allowed to stir 1 h before saturated aqueous NH4Cl (30 mL) was added. The aqueous layer was extracted with EtOAc (3 to 30 mL). The combined organic layers were dried (Na2SO4), filtered, and concentrated under reduced pressure. The crude product was chromatographed. Next, a solution of the above product (128 mg, 0.23 mmol, 1 equiv) in THF (2.2 mL) under $N_2$ was treated with Bu4NF (1 M in THF, 0.46 mL, 0.46 mmol, 2 equiv) and stirred at 25° C. for 2.5 h. Water (30 mL) was added and the aqueous layer was extracted with EtOAc (3 to 30 mL). The combined organic layers were dried (Na2SO4), filtered, and concentrated under reduced pressure. The crude product was chromatographed (SiO2, 2 to 5 cm, 5–33% EtOAc-hexane gradient elution) to afford 72 (51 mg, 69%) as a white film: 1H NMR (CDCl3, 400 MHz) d 5.36–5.29 (m, 2H), 3.62 (t, 2H, J=6.6 Hz), 2.02–1.97 (m, 4H), 1.54 (m, 2H), 1.28–1.24 (m, 30H), 0.86 (t, 3H, J=6.8 Hz); 13C NMR (CDCl3, 100 MHz) d 129.9, 129.8, 63.1, 32.8, 31.9, 29.73 (2), 29.67 (2), 29.64 (3), 29.6, 29.5, 29.39, 29.35, 29.31, 29.2, 27.2, 25.7, 22.7, 14.1; IR (film) nmax 3328, 2923, 2852, 1457, 1055 cm −1; FABHRMS (NBA-NaI) m/z 325.3475 (C22H44O+H+ requires 325.3470).

Synthesis of 4-[(6R*,1R*)-6-Butoxyethyl-3-cyclohexenyl-1-methoxy]butyramide (Trans Isomer to Compound #5, FIG. 7)—Note, This Compound is Not Shown in FIG. 7, But is Claimed)

Butyraldehyde (2.0 mL, 22.2 mmol, 3 equiv) and pyridinium p-toluenesulfonate (191 mg, 0.76 mmol, 0.1 equiv) were added to a solution of commercially available [1(R*)6(R*)-hydroxymethyl-3-cyclohexenyl] (1.07 g, 7.5 mmol, 1 equiv; Aldrich) in anhydrous benzene (25 mL) under N2 atmosphere. The reaction was heated to reflux with a Dean-Stark trap for 1.5 h. Saturated aqueous NaHCO3 (60 mL) was added and the aqueous layer was extracted with EtOAc (3 to 60 mL). The combined organic layers were dried (Na2SO4), filtered, and concentrated under reduced pressure. The crude product was chromatographed (SiO2, 3 to 15 cm, 0–10% EtOAc-hexane gradient elution) to afford 147 (1.12 g, 76%) as a clear oil (diastereomer with lower Rf): 1H NMR (CDCl3, 400 MHz) d 5.59 (s, 2H), 4.70 (t, 1H, J=5.6 Hz), 3.78 (d, J=6.2 Hz, 1H), 3.75 (d, J=6.1 Hz, 1H), 3.55 (d, J=2.7 Hz, 1H), 3.52 (d, J=2.4 Hz, 1H), 2.15–2.02 (m, 6H), 1.54–1.48 (m, 2H), 1.34 (m, 2H), 0.89 (t, 3H, J=7.3 Hz); 13C NMR (CDCl3, 100 MHz) d 125.2(2), 102.1, 68.4 (2), 37.0 (2), 36.7, 26.1 (2), 18.0, 13.9; IR (film) nmax 3024, 2959, 2931, 2873, 1732, 1462, 1378, 1271, 1143, 991, 825 cm−1; FABHRMS opens up acetal. Next, A solution of the above material (98 mg, 0.50 mmol, 1 equiv) in anhydrous CH2Cl2 (5 mL) under N2 atmosphere at 0° C. was treated with DIBAL (1 M in toluene, 2.5 mL, 2.5 mmol, 5 equiv) for 15 min. The reaction was warmed to 25° C. for 3.5 h. The reaction mixture was recooled to 0° C. before the addition of CH3OH (2 mL) and 1 N aqueous HCl (30 mL). After 15 min, the aqueous layer was extracted with EtOAc (3 to 30 mL). The combined organic layers were dried (Na2SO4), filtered, and concentrated under reduced pressure. The crude product was chromatographed (SiO2, 2 to 8 cm, 10–20% EtOAc-hexane gradient elution) to afford 148 (86.7 mg, 88%) as a clear oil: 1H NMR (CDCl3, 400 MHz) d 5.60–5.54 (m, 2H), 3.61–3.28 (m, 7H), 2.16–1.92 (m, 6H), 1.53 (m, 2H), 1.34 (hex, 2H, J=7.6 Hz), 0.88 (t, 3H, J=7.4 Hz); 13C NMR (CDCl3, 100 MHz) d 125.7, 125.3, 72.3, 71.2, 64.4, 38.2, 35.1, 31.5, 28.0, 26.2, 19.3, 13.8; IR (film) nmax 3395, 3022, 2957, 2571, 1463, 1439, 1378, 1112 1037, 622 cm−1; FABHRMS (NBA-NaI) m/z 199.1694 (C12H22O2+H+ requires 199.1698). Next, A solution of the above compound (91 mg, 0.46 mmol, 1 equiv) in anhydrous DMF (2.5 mL) under N2 atmosphere at 0° C. was treated with NaH (39 mg, 0.99 mmol, 2 equiv). The reaction was allowed to stir at 25° C. for 15 min and then was recooled to 0° C. 4-Bromobutyronitrile (230 mL, 2.3 mmol, 5 equiv) was added dropwise and the reaction mixture was heated to 90° C. for 24 h and 140° C. for 17 h. Water (30 mL) was added and the aqueous layer was extracted with EtOAc (3¥30 mL). The combined organic layers were dried (Na2SO4), filtered, and concentrated under reduced pressure. The crude product was chromatographed (SiO2, 2¥10 cm, 2–20% EtOAc-hexane gradient elution) to afford 149 (25 mg, 20%) as a clear oil: 1H NMR (CDCl3, 400 MHz) d 5.60 (s, 2H), 3.52–3.25 (m, 8H), 2.44 (t, 2H, J=7.1 Hz), 2.15–2.08 (m, 4H), 1.91–1.84 (m, 4H), 1.52 (m, 2H), 1.35 (m, 2H), 0.89 (t, 3H, J=7.4 Hz); 13C NMR (CDCl3, 100 MHz) d 125.7, 125.4, 119.6, 72.0, 71.6, 70.9, 68.2, 34.7, 34.6, 31.8, 27.0, 26.8, 25.8, 19.4, 14.1, 13.9; IR (film) nmax 3020, 2930, 2866, 1726, 1463, 1438, 1377, 1113, 662 cm−1; FABHRMS (NBA-NaI) m/z 266.2125 (C16H27NO2+H+ requires 266.2120). Also isolated was 150 (28 mg, 27%) as a clear oil: 1H NMR (CDCl3, 400 MHz) d 8.05 (s, 1H), 5.65–5.57 (m, 2H), [4.22 and 4.20][d, 1H, J=5.8 Hz], [4.10 (d, J=8.6 Hz) and 4.08 (d, J=9.0 Hz)][1H], 3.43–3.28 (m, 4H), 2.27–2.09 (m, 4H), 1.96–1.86 (m, 2H), 1.52 (m, 2H), 1.34 (m, 2H), 0.89 (t, 3H, J=7.3 Hz); 13C NMR (CDCl3, 100 MHz) d 161.2, 125.8, 124.9, 71.5, 71.0, 64.9, 34.5, 33.8, 31.8, 26.8, 26.5, 19.3, 13.9; IR (film) nmax 3024, 2958, 2928, 2862, 1727, 1466, 1439, 1378, 1167, 1113, 663 cm−1; FABHRMS (NBA-NaI) m/z 227.1655 (C13H22O3+H+ requires 227.1647). A solution of the above compound (320 mg, 1.61 mmol, 1 equiv) in anhydrous DMF (8 mL) under N2 atmosphere at 0° C. was treated with NaH (77 mg, 1.93 mmol, 1.2 equiv)for 15 min. A solution of 151 (0.95 g, 2.31 mmol, 1.4 equiv) in DMF (3 mL) was added dropwise and the reaction mixture was allowed to stir at 25° C. for 17 h. Bu4NI (0.60 g, 1 equiv) was added and the reaction was stirred 7 h, and heated to 60° C. for 19 h. Water (30 mL) was added and the aqueous layer was extracted with EtOAc (3 to 30 mL). The combined organic layers were dried (Na2SO4), filtered, and concentrated under reduced pressure. The crude product was chromatographed (SiO2, 2 to 10 cm, 0–20% EtOAc-hexane gradient elution) to afford the product (123 mg, 15%) as a clear oil Next, a solution of the above compound (111 mg, 0.22 mmol, 1 equiv) in anhydrous THF (2 mL) under N2 atmosphere at 25° C. was treated with Bu4NF (1 M in THF, 0.44 mL, 0.44 mmol, 2 equiv) for 3 h. Water (30 mL) was added and the aqueous layer was extracted with EtOAc (3¥30 mL). The combined organic layers were dried (Na2SO4), filtered, and concentrated under reduced pressure. The crude product was chromatographed Next, A solution of the above compound (33 mg, 0.12 mmol, 1 equiv) in anhydrous DMF (0.6 mL) under N2 atmosphere was treated with PDC (0.23 g, 0.61 mmol, 5 equiv). The reaction was stirred at 25° C. for 4.5 h, filtered through Celite, and concentrated under reduced pressure. Next, A solution of the above compound (41 mg, 0.14 mmol, 1 equiv) in anhydrous CH2Cl2 (0.8 mL) under N2 at 0° C. was treated with oxalyl chloride (2 M in CH2Cl2, 0.21 mL, 0.42 mmol, 3 equiv). The reaction mixture was warmed to 25° C. and stirred for 3 h in the dark before the solvent was removed under reduced pressure. The residue was cooled to 0° C., diluted with EtOAc, and treated with excess NH4OH (1 mL). Water (30 mL) was added and extracted with EtOAc (3×30 mL). The combined organic layers were dried (Na2SO4), filtered, and concentrated under reduced pressure. The crude product was chromatographed (SiO2, 1×10 cm, 50–100% EtOAc-hexane gradient elution) to afford product (21 mg, 52%) as a clear oil. Next a solution of the above cyclohexene compound (21 mg, 0.074 mmol, 1 equiv) was combined with 10% Pd/C (11 mg) under Ar atmosphere. Absolute EtOH (1 mL) was added and the atmosphere was replaced with H2. The reaction was stirred at 25° C. for 21 h. A second portion of 10% Pd/C (20 mg) was added and the reaction was stirred an additional 16 h. The crude mixture was filtered through Celite and the solvent removed under reduced pressure to afford product (19 mg, 89%) as a clear oil;

Finally, 4-[(6R*,1R*)-6-Butoxymethyl-3-cyclohexenyl-1-methoxy]butyramide was synthesized using a solution of the above compound; 31 mg, 0.12 mmol, 1 equiv) and powdered KOH (62 mg, 1.1 mmol, 9 equiv) in t-butanol (0.12 mL) was heated to 100° C. for 30 min. The crude reaction was cooled to 25° C., diluted with brine (2 mL), and extracted with EtOAc (5 to 2 mL). The combined organic layers were dried (Na2SO4), filtered, and concentrated under reduced pressure. The crude product was chromatographed (SiO2, 1 to 6 cm, 50–80% EtOAc-hexane gradient elution) to afford final product (25 mg, 76%) as a clear oil: 1H NMR (CDCl3, 400 MHz) d 5.79 (br, 1H), 5.60 (s, 2H), 5.31 (br, 1H), 3.46–3.25 (m, 8H), 2.32 (t, 2H, J=7.2 Hz), 2.16–2.06 (m, 4H), 1.93–1.85 (m, 4H), 1.55–1.48 (m, 2H), 1.38–1.28 (m, 2H), 0.89 (t, 3H, J=7.3 Hz); 13C NMR (CDCl3, 100 MHz) d 175.4, 125.7, 125.5, 71.8, 71.4, 70.9, 69.8, 34.7, 34.5, 32.8, 31.8, 27.1, 26.8, 25.4, 19.4, 13.9; IR (film) nmax 3341, 3203, 3022, 2929, 2860, 1667, 1435, 1404, 1377, 1110, 661 cm−1; FABHRMS (NBA-NaI) m/z 284.2235 (C16H29NO3+H+ requires 284.2226).

Synthesis of 4-[(1R*,2R*)-6-Butoxymethyl-3-cyclohexyl-1-methoxy]butyramide (Trans Isomer to Compound #5, FIG. 7)—Note, This Compound is Not Shown in FIG. 7, But is Claimed Cyclohexene (19 mg, 0.068 mmol, 1 equiv; vida supra) was combined with 10% Pd/C (21 mg) under Ar atmosphere. Absolute EtOH (1 mL) was added and the atmosphere was replaced with H2. The reaction was stirred at 25° C. for 24 h. The crude mixture was filtered through Celite and the solvent removed under reduced pressure to afford 164 (18 mg, 91%) as a clear oil: 1H NMR (CDCl3, 400 MHz) d 5.83 (br, 1H), 5.34 (br, 1H), 3.44–3.25 (m, 8H), 2.32 (t, 2H, J=7.1 Hz), 1.95–1.85 (m, 4H), 1.55–1.29 (m, 12H), 0.89 (t, 3H, J=7.4 Hz); 13C NMR (CDCl3, 100 MHz) d 175.4, 71.7, 71.3, 70.8, 69.8, 37.5, 37.2, 32.8, 31.8, 26.9, 26.6, 25.5, 23.7, 23.5, 19.4, 13.9; IR (film) nmax 3351, 3194, 2916, 2855, 1667, 1614, 1446, 1377, 1261, 1104, 667 cm−1; FABHRMS (NBA-NaI) m/z 308.2194 (C16H31NO3+Na+ requires 308.2202).

Synthesis of Methanesulfonic Acid 7Z-Hexadecenyl Ester, Claimed But Not Shown, This Compound is Similar to Compounds as Illustrated in FIG. 3

A solution of 7Z-hexadecenol (42 mg, 0.18 mmol, 1 equiv) and anhydrous Et3N (55 mL, 0.39 mmol, 2.2 equiv) in anhydrous CH2Cl2 (0.8 mL) under N2 atmosphere was treated with MsCl (30 mL, 0.39 mmol, 2.2 equiv). The reaction was stirred at 25° C. for 4 h before the addition of water (2 mL). The aqueous layer was extracted with EtOAc (5 to 2 mL) and the combined organic layers were dried (Na2SO4), filtered, and concentrated under reduced pressure. The crude product was chromatographed (SiO2, 2 to 8 cm, 10–20% EtOAc-hexane gradient elution) to afford 175 (56 mg, 100%) as a clear oil: 1H NMR (CDCl3, 400 MHz) d 5.37–5.27 (m, 2H), 4.19 (t, 2H, J=6.6 Hz), 2.97 (s, 3H), 1.99 (m, 4H), 1.72 (m, 2H), 1.41–1.24 (m, 18H), 0.85 (t, 3H, J=6.8 Hz); 13C NMR (CDCl3, 100 MHz) d 130.2, 129.3, 70.1, 37.3, 31.8, 29.7, 29.5 (2), 29.3 (2), 29.1, 28.6, 27.2, 26.9, 25.3, 22.6, 14.1; IR (film) nmax 2924, 2854, 1463, 1356, 1176, 954, 816, 719 cm−1; FABHRMS (NBA-NaI) m/z 341.2135 (C17H34O3S+Na+ requires 341.2126).

Synthesis of 1-Azido-7Z-hexadecene, Claimed But Not Shown, This Compound is Similar to Compounds as Illustrated in FIG. 3

A solution of methanesulfonic Acid 7Z-Hexadecenyl Ester (49 mg, 0.15 mmol, 1 equiv; vida supra) in anhydrous DMF (1.0 mL) under N2 atmosphere was treated with NaN3 (21 mg, 0.32 mmol, 2.2 equiv). The reaction was stirred at 25° C. for 23 h before the addition of water (2 mL). The aqueous layer was extracted with EtOAc (5×2 mL) and the combined organic layers were dried (Na2SO4), filtered, and concentrated under reduced pressure. The crude product was chromatographed (SiO2, 2 to 5 cm, 0–2% EtOAc-hexane gradient elution) to afford 176 (37 mg, 90%) as a clear oil: 1H NMR (CDCl3, 400 MHz) d 5.38–5.28 (m, 2H), 3.24 (t, 2H, J=7.0 Hz), 2.00 (m, 4H), 1.58 (m, 2H), 1.39–1.25 (m, 18H), 0.86 (t, 3H, J=6.8 Hz); 13C NMR (CDCl3, 100 MHz) d 130.2, 129.5, 51.5, 31.9, 29.7, 29.6, 29.5, 29.3 (2), 28.80, 28.76, 27.2, 27.0, 26.6, 22.7, 14.1; IR (film) nmax 2925, 2854, 2094, 1460, 1260 cm−1; ESMS (NBA-NaI) m/z 288 (M+Na+).

Synthesis of 7Z-Hexadecenamine, Claimed But Not Shown, This Compound is Similar to Compounds as Illustrated in FIG. 3

A solution of azide (57 mg, 0.22 mmol, 1 equiv; vida supra) in anhydrous Et2O (1.0 mL) under N2 atmosphere was cooled to 0° C. and treated with LiAlH4 (19 mg, 0.50 mmol, 2.3 equiv). The reaction was allowed to stir at 25° C. for 20 min. The mixture was then recooled to 0° C. and saturated aqueous Na2SO4 was added until all excess LiAlH4 was quenched. Solid Na2SO4 was added, the mixture was filtered, and the solvent removed under reduced pressure to afford 177 (44 mg, 86%) as a clear oil: 1H NMR (CDCl3, 400 MHz) d 5.36–5.28 (m, 2H), 2.67 (br, 2H), 2.00–1.96 (m, 4H), 1.45–1.24 (m, 20H), 0.85 (t, 3H, J=6.7 Hz); 13C NMR (CDCl3, 100 MHz) d 130.0, 129.7, 42.2, 31.9, 29.8, 29.7 (2), 29.5, 29.3 (2), 29.1, 27.2, 27.1, 26.8, 22.7, 14.1; IR (film) nmax 2923, 2853, 1570, 1464, 1312, 818, 724 cm−1; FABHRMS (NBA-NaI) m/z 240.2698 (C16H33N+H+ requires 240.2691).

Materials

The fatty acid primary amides (FIG. 2) were prepared by treating the acid chlorides, generated from the corresponding carboxylic acid and oxalyl chloride, with aqueous NH4OH according the procedures in Cravatt et al. (1996) *J. Am. Chem. Soc.* 118, 580–590; Patterson et al. (1996) *J. Am. Chem. Soc.* 118, 5938–5945). Many of the fatty acids were commercially available (Sigma, Aldrich, Fluka), and the remainder were synthesized as detailed vida infra. Most agents in FIG. 3 were prepared by condensing oleoyl chloride with the appropriate amine or alcohol following procedures in Cravatt et al. (1996) *J. Am. Chem. Soc.* 118, 580–590; Patterson et al. (1996) *J. Am. Chem. Soc.* 118, 5938–5945; Roe et al. *J. Am. Chem. Soc.* 71, 2215–2218; Roe et al. (1952) *J. Am. Chem. Soc.* 74, 3442–3443. The remaining agents in FIG. 3 are commercially available (Sigma, Pfaltz & Bauer) or are prepared vida infra. The ethanolamides (FIG. 4) were similarly prepared or purchased (Pfaltz & Bauer). The synthesis of the 18-hydroxyoleamide was described in Cravatt et al. (1996) *J. Am. Chem. Soc.* 118, 580–590 and standard transformations following protocols detailed therein were used to prepare the remaining agents in FIG. 5. N-Oleoyl glycine (FIG. 6) was prepared by coupling glycine ethyl ester to oleic acid with EDCI (Cravatt et al. (1996) *J. Am. Chem. Soc.* 118, 580–590; Patterson et al. (1996) *J. Am. Chem. Soc.* 118, 5938–5945) followed by sequential transformation to the carboxylic acid (LiOH) and glycinamide (EDCI, NH4OH). N-Oleoyl sarcosine was purchased (Pfaltz and Bauer) and converted to its ethyl ester by coupling with EtOH (DCC). The agents in FIG. 7 were prepared as described in Cravatt et al. (1996) *J. Am. Chem. Soc.* 118, 580–590; Simmons et al. (1959) *J. Am. Chem. Soc.* 81, 4256–4264) or by a series of Wittig couplings to the appropriately substituted o, m, or p-cyanobenzaldehyde. Substitutions at the α-carbon (FIG. 8) were installed by treating the enolate of oleic acid or methyl oleate (generated by LDA) with an appropriate electrophile as previously detailed in Patterson et al. (1996) *J. Am. Chem. Soc.* 118, 5938–5945). The primary carbamate and urethanes were prepared from the corresponding alcohols or amines (HCl, NaOCN).

Cell Culture

Rat glial cells (Suter et al., 1987) obtained from Dr. Trosko's laboratory were cultured in standard plastic tissue cultureware in Richter's Improved Minimal Essential Medium (Irvine Scientific, Santa Ana, Calif.), supplemented with 10% fetal calf serum and 50 $\mu$g/ml gentamicin sulfate, and incubated in a humidified atmosphere of 95% air/5% CO2 at 37° C. The cells were passaged by trypsinization and used at passages 4–8. BHK (baby hamster kidney) cells that were stably transfected with a β1 connexin cDNA (Kumar et al., 1995) were cultured in DMEM medium supplemented with 5% fetal calf serum and 50 $\mu$g/ml gentamicin sulfate, and incubated in a humidified atmosphere of 95% air/5% CO2 at 37° C. In order to induce β1 connexin expression in the BHK cells, 100 $\mu$M zinc acetate was added to culture medium for 8–18 hours when the cell culture was about 90% confluent.

Gap Junction Dye Coupling Assays

Gap junctional communication in glial cell and BHK/β1 cell cultures was assayed by microinjection of 5% Lucifer yellow CH dye in 0.1 M LiCl solution, and quantitated by determining the number of directly adjacent, neighboring cells that received dye (dye-coupling). Micropipettes were loaded with the dye solution by backfilling. Cells were visualized using a Nikon Diaphot inverted phase contrast/ epifluorescent microscope, and impaled with dye-filled micropipettes using an Eppendorf microinjector (model 5246). Five minutes after dye-injection, the transfer of dye to directly adjacent cells was determined using epifluorescent illumination. For each treatment condition, ten cells were microinjected in each of three dishes, the total number of dye-coupled neighboring cells was calculated and compared to determine the % dye-coupling. For scrape loading measurements, Lucifer yellow CH (0.05% dye in PBS) was loaded intracellularly by cutting or scraping cells in the monolayer with a sharp knife. The dye solution was left in the dish for 90 seconds, then the solution was discarded, and the dish subsequently washed with PBS. The cells were examined for dye transfer with an inverted epifluorescence microscope, and the degree of communication was assessed by determining the extent of Lucifer yellow transfer into contiguous cells.

Gap Junction Electrical Coupling Assay

Junctional conductance was measured using double whole cell patch recording performed on pairs of rat glial cells as described (Miller et al., (1992) J Mem. Biol. 128, 91–102) with a pipette solution of (in nM): Kaspartate 160, EGTA 10, $CaCl_2$ 2, HEPES 10 (pH 7.2), ATP 4. The external solution contained (in mM): NaCl 160, KCl 4.5, CaCl2 2, MgCl2 1, HEPES 10, pH 7.4. Both cells were held at −40 mV and pulses to −20 mV were alternately applied to each cell. Holding currents were subtracted in the records shown. Cells that were examined were generally in contact with other cells. The electrical conductance was calculated as the junctional current divided by 20 mV. All dye-coupling and conductance studies were performed at room temperature.

Calcium Wave Images

Rat glial cells were loaded with 5 $\mu$M Fluo-3/AM (Calbiochem) in Hank's balanced salt solution containing 25 mM HEPES buffer (HBSS/HEPES) for 1 hour, at which point the loading buffer was exchanged for new HBSS/ HEPES buffer. The cell cultures were then left at room temperature for at least 30 minutes. Mechanical stimulation of a single cell was performed as follows: a glass micropipette (tip diameter of approximately 0.5 $\mu$m) was micromanipulated downward on to a single cell causing a transient deformation of the cell membrane. The calcium image was then examined with an inverted fluorescence microscope, and photographed with a digital fluorescence microscope (excitation=506 nm, emmision=526 nm). The degree of calcium wave propagation was quantitated by counting at different time points the number of transmitting cells in one linear direction away from the stimulated cell. Junctional dye transfer rates were simultaneously examined by microinjection of Lucifer yellow CH in the same dishes; the methods for dye transfer assay was described in assay procedures, gap junction dye coupling assays. For calcium wave and dye transfer studies, the drug was preincubated with the glial cells for 10 minutes, and the drug was left in the experimental solution throughout the examination. All measurements were performed at room temperature.

Immunoblotting

Plasma membrane fractions containing gap junctions were obtained after hypotonic alkali extraction of the glial cells. The extracted protein was dissolved in 20 SDS and the total protein was determined using the Bio-Rad DC Protein Assay kit (Bio-Rad Corp.). 10 $\mu$g of protein was electrophoresed by 10% SDS-PAGE, and subsequently blotted electrophoretically on to Immobilon-P membranes (Millipore Corp.). Gap junction protein was detected using anti-α1 connexin polyclonal rabbit antibodies, and the HRP/ Chemiluminescence detection kit (Amersham Corp.) following the manufacturer's instructions.

What is claimed is:

1. A method for inhibiting gap junction mediated chemical and electrical transmission in glial cells by contact with an oleamide agonist represented by the structure:

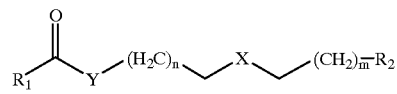

wherein:

X is a diradical selected from the group represented by the following structures:

[diradical structures shown]

wherein Z is a radical selected from the group consisting of: —CH$_2$ and O;

Y is a diradical selected from the group consisting of: —CH$_2$—, —CH(CH$_3$)—, —C(CH$_3$)$_2$—, —O—, —NH—, —CH(SH)—, —CHSAc)—, —CH(OH)—, —CHCl—, —C(=O)—, —C(=O)CH$_2$—, —CH$_2$NHC(=O)—, and —CH$_2$N(CH$_3$)C(=O)—;

R$_1$ is a radical selected from the group consisting of: hydrogen, —NH$_2$, OH, MeNH—, Me$_2$N—, EtNH—, Et$_2$N—, CH$_2$=CHCH$_2$NH—, n-propyl-NH—, i-propyl-NH—, cyclopropyl-NH—, i-propyl-NMe-, butyl-NH—, pyrrolidine-, phenyl-NH—, phenyl(CH$_2$)$_3$NH—, HONH—, MeONMe-, NH$_2$NH—, CH$_3$O—, CH$_3$CH$_2$O—, CH$_3$(CH$_2$)$_2$O—, Me$_2$CHCH$_2$O—, H—, CF$_3$—, BrCH$_2$—, ClCH$_2$—, N$_2$CH—, HOCH$_2$CH$_2$NH—, (HOCH$_2$CH$_2$)$_2$N—, HOCH$_2$CH$_2$CH$_2$NH— and HOCH$_2$CH(OAc)CH$_2$O—;

R$_2$ is a radical selected from the group consisting of: —CH$_3$, —(CH$_2$)$_2$CH$_3$, —(CH$_2$)$_4$CH$_3$, —(CH$_2$)$_6$CH$_3$, —CH$_2$OCH$_3$, —CH$_2$OH, —CNOH$_2$ and —CO$_2$H;

n is an integer from 0 to 15; m is an integer from 0 to 15 with the requirement that the sum of n+m is an integer from 11 to 15;

with the following provisos:
  if Y is CH$_2$, n is 4, m is 7, and R$_2$ is CH$_3$, then R$_1$ cannot be a radical selected from the group consisting of —CF$_3$ and hydrogen;
  if Y is CH$_2$, n is 5, m is 7, and R$_2$ is CH$_3$, then R$_1$ cannot be a radical selected from the group consisting of —CF$_3$, —CH$_2$Cl, —NHOH, —C(O)NH$_2$, —CN$_2$, and —C(O)OEt;
  if Y is CHCl, n is 4, m is 7, and R$_2$ is CH$_3$, then R$_1$ cannot be NH$_2$;
  if Y is CH(OH), n is 4, m is 7, and R$_2$ is CH$_3$, then R$_1$ cannot be NH$_2$;
  if Y is C(=O), n is 4, m is 7, and R$_2$ is CH$_3$, then R$_1$ cannot be NH$_2$ and CH$_3$CH$_2$O—;
  if Y is CH$_2$, 4≦n≦9, 4≦n≦7, and R$_2$ is CH$_3$, then R$_1$ cannot be NH$_2$ and OH.

2. A compound having oleamide agonist activity for inhibiting gap junction-mediated chemical and electrical transmission in glial cells represented by the structure:

[structure: R$_1$—C(=O)—Y—(H$_2$C)$_n$—X—(CH$_2$)$_m$—R$_2$]

wherein:

X is a diradical selected from the group represented by the following structures:

[diradical structures shown]

wherein Z is a radical selected from the group consisting of: —CH$_2$ and O;

Y is a diradical selected from the group consisting of: —CH$_2$—, —CH(CH$_3$)—, —C(CH$_3$)$_2$—, —O—, —NH—, —CH(SH)—, —CHSAc)—, —CH(OH)—, —CHCl—, —C(=O)—, —C(=O)CH$_2$—, —CH$_2$NHC(=O)—, and —CH$_2$N(CH$_3$)C(=O)—;

R$_1$ is a radical selected from the group consisting of: hydrogen, —NH$_2$, OH, MeNH—, Me$_2$N—, EtNH—, Et$_2$N—, CH$_2$=CHCH$_2$NH—, n-propyl-NH—, i-propyl-NH—, cyclopropyl-NH—, i-propyl-NMe-, butyl-NH—, pyrrolidine-, phenyl-NH—, phenyl(CH$_2$)$_3$NH—, HONH—, MeONMe-, NH$_2$NH—, CH$_3$O—, CH$_3$CH$_2$O—, CH$_3$(CH$_2$)$_2$O—, Me$_2$CHCH$_2$O—, H—, CF$_3$—, BrCH$_2$—, ClCH$_2$—, N$_2$CH—, HOCH$_2$CH$_2$NH—, (HOCH$_2$CH$_2$)$_2$N—, HOCH$_2$CH$_2$CH$_2$NH— and HOCH$_2$CH(OAc)CH$_2$O—;

R$_2$ is a radical selected from the group consisting of: —CH$_3$, —(CH$_2$)$_2$CH$_3$, —(CH$_2$)$_4$CH$_3$, —(CH$_2$)$_6$CH$_3$, —CH$_2$OCH$_3$, —CH$_2$OH, —CONH$_2$ and —CO$_2$H;

n is an integer from 0 to 15; m is an integer from 0 to 15 with the requirement that the sum of n+m is an integer from 11 to 15;

with the following provisos:
  if Y is CH$_2$, n is 4, m is 7, and R$_2$ is CH$_3$, then R$_1$ cannot be a radical selected from the group consisting of —CF$_3$ and hydrogen;
  if Y is CH$_2$, n is 5, m is 7, and R$_2$ is CH$_3$, then R$_1$ cannot be a radical selected from the group consisting of —CF$_3$, —CH$_2$Cl, —NHOH, —C(O)NH$_2$, —CN$_2$, and —C(O)OEt;
  if Y is CHCl, n is 4, m is 7, and R$_2$ is CH$_3$, then R$_1$ cannot be NH$_2$;
  if Y is CH(OH), n is 4, m is 7, and R$_2$ is CH$_3$, then R$_1$ cannot be NH$_2$;
  if Y is C(=O), n is 4, m is 7, and R$_2$ is CH$_3$, then R$_1$ cannot be NH$_2$ and CH$_3$CH$_2$O—;
  if Y is CH$_2$, 4≦n≦9, 4≦n≦7, and R$_2$ is CH$_3$, then R$_1$ cannot be NH$_2$ and OH.

* * * * *